US011857535B2

(12) United States Patent
Walker

(10) Patent No.: US 11,857,535 B2
(45) Date of Patent: Jan. 2, 2024

(54) METHODS OF TREATING MUTANT LYMPHOMAS

(71) Applicant: Kymera Therapeutics, Inc., Watertown, MA (US)

(72) Inventor: Duncan Walker, Watertown, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/444,015

(22) Filed: Jul. 29, 2021

(65) Prior Publication Data

US 2022/0054453 A1 Feb. 24, 2022

Related U.S. Application Data

(60) Provisional application No. 63/202,242, filed on Jun. 2, 2021, provisional application No. 63/109,854, filed on Nov. 4, 2020, provisional application No. 63/058,891, filed on Jul. 30, 2020.

(51) Int. Cl.
*A61K 31/40* (2006.01)
*A61K 31/404* (2006.01)
*A61P 35/00* (2006.01)

(52) U.S. Cl.
CPC .......... *A61K 31/404* (2013.01); *A61P 35/00* (2018.01)

(58) Field of Classification Search
CPC .................................. A61K 31/404
See application file for complete search history.

(56) References Cited

U.S. PATENT DOCUMENTS

| | | | |
|---|---|---|---|
| 7,390,799 | B2 | 6/2008 | Bruncko et al. |
| 7,501,496 | B1 | 3/2009 | Endl et al. |
| 10,874,743 | B2 | 12/2020 | Mainolfi et al. |
| 11,065,231 | B2 | 7/2021 | Crew et al. |
| 11,117,889 | B1 | 9/2021 | Mainolfi et al. |
| 2005/0014802 | A1 | 1/2005 | Attardo et al. |
| 2007/0098719 | A1 | 5/2007 | Smith et al. |
| 2009/0055944 | A1 | 2/2009 | Korman et al. |
| 2009/0136494 | A1 | 5/2009 | Ponath et al. |
| 2010/0150892 | A1 | 6/2010 | Han |
| 2010/0197686 | A1 | 8/2010 | Xing et al. |
| 2010/0203056 | A1 | 8/2010 | Irving et al. |
| 2010/0233183 | A1 | 9/2010 | Triebel et al. |
| 2011/0008331 | A1 | 1/2011 | Triebel |
| 2011/0053941 | A1 | 3/2011 | Mautino et al. |
| 2011/0136796 | A1 | 6/2011 | Mautino et al. |
| 2011/0165156 | A1 | 7/2011 | Dimoudis et al. |
| 2011/0274683 | A1 | 11/2011 | Wong et al. |
| 2012/0189639 | A1 | 7/2012 | Schebye et al. |
| 2012/0277217 | A1 | 11/2012 | Mautino et al. |
| 2012/0329997 | A1 | 12/2012 | Fertig et al. |
| 2013/0005949 | A1 | 1/2013 | Fertig et al. |
| 2013/0149236 | A1 | 6/2013 | Johnson et al. |
| 2014/0066625 | A1 | 3/2014 | Mautino et al. |
| 2014/0079699 | A1 | 3/2014 | Wong et al. |
| 2014/0079706 | A1 | 3/2014 | Cannarile et al. |
| 2014/0093511 | A1 | 4/2014 | Lonberg et al. |
| 2014/0336363 | A1 | 11/2014 | Fertig et al. |
| 2014/0341917 | A1 | 11/2014 | Nastri et al. |
| 2019/0151295 | A1 | 5/2019 | Crew et al. |
| 2019/0192668 | A1 | 6/2019 | Mainolfi et al. |
| 2021/0228562 | A1 | 7/2021 | Weiss |
| 2021/0323952 | A1 | 10/2021 | Mainolfi et al. |

FOREIGN PATENT DOCUMENTS

| | | |
|---|---|---|
| WO | 2004106328 A1 | 12/2004 |
| WO | 2006029879 A2 | 3/2006 |
| WO | 2006105021 A2 | 10/2006 |
| WO | 2007005874 A2 | 1/2007 |
| WO | 2008118802 A1 | 10/2008 |
| WO | 2008132601 A1 | 11/2008 |
| WO | 2009009116 A2 | 1/2009 |
| WO | 2009044273 A3 | 4/2009 |
| WO | 2009073620 A2 | 6/2009 |
| WO | 2009132238 A3 | 10/2009 |
| WO | 2010019570 A2 | 2/2010 |
| WO | 2010077634 A1 | 7/2010 |
| WO | 2011028683 A1 | 3/2011 |
| WO | 2011056652 A1 | 5/2011 |
| WO | 2011070024 A1 | 6/2011 |
| WO | 2011107553 A1 | 9/2011 |
| WO | 2011109400 A2 | 9/2011 |
| WO | 2011131407 A1 | 10/2011 |
| WO | 2011140249 A2 | 11/2011 |
| WO | 2012032433 A1 | 3/2012 |
| WO | 2012142237 A1 | 10/2012 |
| WO | 2012145493 A1 | 10/2012 |
| WO | 2013079174 A1 | 6/2013 |
| WO | 2013087699 A1 | 6/2013 |
| WO | 2013119716 A1 | 8/2013 |
| WO | 2013132044 A1 | 9/2013 |
| WO | 2013169264 A1 | 11/2013 |
| WO | 2014008218 A1 | 1/2014 |

(Continued)

OTHER PUBLICATIONS

Adams et al., "Big opportunity for small molecules in immuno-oncology," Nat. Rev. Drug. Discov. 2015;14(9):603-22.
Berge, et al., "Pharmaceutical salts," J Pharm Sci. 1977; 66(1):1-19.
Chang et al., "What is the functional role of the thalidomide binding protein cereblon?" Int J Biochem Mol Biol. 2011;2(3):287-94.
Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," J Med Chem. 2015;58(1):96-110.
Dunne et al., "IRAK1 and IRAK4 Promote Phosphorylation, Ubiquitation, and Degradation of MyD88 Adaptor-like (Mal)," J Biol Chem. 2010;285(24):18276-82.
Hagner et al., "CC-122, a pleiotropic pathway modifier, mimics an interferon response and has antitumor activity in DLBCL," Blood. 2015;126(6):779-89.

(Continued)

*Primary Examiner* — Shawquia Jackson
(74) *Attorney, Agent, or Firm* — Dechert LLP; Andrea L. C. Reid; Todd K. Macklin

(57) ABSTRACT

The present invention relates to methods of treating MYD88-mutant B-cell lymphomas using IRAK4 degrader.

30 Claims, 11 Drawing Sheets

(56) References Cited

FOREIGN PATENT DOCUMENTS

| | | | |
|---|---|---|---|
| WO | 2014036357 A1 | 3/2014 |
| WO | 2019099926 A1 | 5/2019 |
| WO | 2019133531 A1 | 7/2019 |
| WO | 2019160915 A1 | 8/2019 |
| WO | 2020010227 A1 | 1/2020 |
| WO | 2020092907 A1 | 5/2020 |
| WO | 2020113233 A1 | 6/2020 |
| WO | 2020264499 A1 | 12/2020 |
| WO | 2021127190 A1 | 6/2021 |

OTHER PUBLICATIONS

Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.

Ito et al., "Identification of a primary target of thalidomide teratogenicity," Science. 2010;327(5971):1345-50.

Kargbo, "Protac Degradation of IRAK4 for the Treatment of Cancer," ACS Med. Chem. Lett., 2019, 10(10):1370-1371.

Kelly et al., "Selective interleukin-1 receptor-associated kinase 4 inhibitors for the treatment of autoimmune disorders and lymphoid malignancy," J Exp Med. 2015;212(13):2189-201.

Krönke et al., "Lenalidomide causes selective degradation of IKZF1 and IKZF3 in multiple myeloma cells" Science. 2014;343(6168):301-305.

Küppers, "IRAK inhibition to shut down TLR signaling in autoimmunity and MyD88-dependent lymphomas," J Exp Med. 2015;212(13):2184.

Li et al., "IRAK-4: A novel member of the IRAK family with the properties of an IRAK-kinase," Proc Natl Acad Sci USA. 2002;99(8):5567-72.

Li et al., "Targeting interleukin-1 receptor-associated kinase for human hepatocellular carcinoma," J Exp Clin Cancer Res. 2016;35(1):140.

Lin et al., "Helical assembly in the MyD88-IRAK4-IRAK2 complex in Tlr /IL-1R signalling," Nature. 2010:465 (7300):885-90.

Lu et al., "The myeloma drug lenalidomide promotes the cereblon-dependent destruction of Ikaros proteins," Science. 2014;343(6168):305-309.

Ngo et al., "Oncogenically active MYD88 mutations in human lymphoma," Nature. 2011;470(7332):115-9.

Nunes et al., "Targeting IRAK4 for Degradation with PROTACTSs," ACS Med Chem Lett. 2019;10(7):1081-1085.

Okazaki et al., "A rheostat for immune responses: the unique properties of PD-1 and their advantages for clinical application," Nat. Immunol. 2013; 14(12): 1212-1218.

PCT International Search Report and Written Opinion from PCT/US2018/067304, dated Apr. 30, 2019.

PCT International Search Report and Written Opinion from PCT/US2019/064070, dated Apr. 6, 2020.

PCT International Search Report and Written Opinion from PCT/US2020/040125 dated Nov. 13, 2020.

PCT International Search Report and Written Opinion from PCT/US2020/065628 dated May 28, 2021.

Picard et al., "Clinical features and outcome of patients with IRAK-4 and MyD88 deficiency," Medicine (Baltimore). 2010;89(6):403-425.

Ramirez et al., "Defining causative factors contributing in the activation of hedgehog signaling in diffuse large B-cell lymphoma," Leuk Res. 2012;36(10):1267-73.

Ross et al., "Bispecific T cell engager (BITE® ) antibody constructs can mediate bystander tumor cell killing," PLoS One. 2017; 12(8): e0183390.

Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphome," J Med Chem. 2017;60(24):10071-10091.

Toogood, "Small molecule immuno-oncology therapeutic agents," Bioorg. Med. Chem. Lett. 2018;28(3):319-329.

Winter et al., "Selective Target Protein Degradation via Phthalimide Conjugation," Science. 2015;348(6241):1376-1381.

Xu et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.

Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53rd ASH Annual Meeting, San Diego, California, Dec. 10-13, 2011.

Yang et al., "Exploiting synthetic lethality for the therapy of ABC diffuse large B cell lymphoma," Cancer Cell. 2012;21(6):723-37.

Zou et al., "PD-L1 (B7-H1) and PD-1 pathway blockade for cancer therapy: Mechanisms, response biomarkers, and combinations," Sci. Transl. Med. 016;8(328):328rv4.

PCT International Search Report and Written Opinion from PCT/U.S. Pat. No. 2021071048, dated Nov. 5, 2021.

METHODS OF TREATING MUTANT LYMPHOMAS

CROSS-REFERENCE TO RELATED APPLICATIONS

This application claims the benefit of U.S. Provisional Appl. No. 63/202,242, filed on Jun. 2, 2021, U.S. Provisional Appl. No. 63/109,854, filed on Nov. 4, 2020, and U.S. Provisional Appl. No. 63/058,891, filed on Jul. 30, 2020, the content of each of which is herein incorporated by reference.

TECHNICAL FIELD OF THE INVENTION

The present invention relates to methods of treating MYD88-mutant B-cell lymphomas using IRAK4 degraders.

BACKGROUND OF THE INVENTION

IRAKIMiD degraders are subset of IRAK4 degraders with a unique profile that combines the activity of IRAK4 degradation and immunomodulatory imide drugs, or IMiDs, for the treatment of MYD88-mutant B-cell lymphomas. Oncogenic mutations of MYD88, most commonly $MYD88^{L265P}$, are common in several subsets of B-cell lymphomas. In particular, MYD88 is estimated to be mutated in approximately 30-40% of ABC-DLBCL cases, 30-70% of primary CNS lymphoma cases, 45-75% of primary extranodal lymphomas cases, and more than 90% of Waldenström macroglobulinemia cases. The presence of MYD88 mutations is often associated with poorer response to chemotherapy and reduced overall survival compared to other genetic subtypes, supporting the need for more effective therapies targeting MYD88-mutated lymphoma.

Treatment of B-cell lymphomas typically involves front-line chemotherapy with a rituximab backbone. While effective in many other patients, front-line chemotherapy has significantly poorer survival rates in ABC-DLBCL. In additional lines of therapy, several novel targeted therapies have been approved recently, including polatuzumab, bendamustine, and chimeric antigen receptor T-cells. While these agents have some notable activity, many patients fail to respond to second line therapy or relapse from these therapies, with no adequate treatment options. Several targeted therapies that impact the NFkB pathway, such as the Bruton's tyrosine kinase inhibitor ibrutinib, or the IMiD lenalidomide, have shown modest single agent activity, with poor durability of response in MYD88-mutated lymphomas.

In oncology, IRAK4 is an obligate protein in MYD88 signaling for which activated mutation is well characterized to drive oncogenesis and IMiDs are a class of drugs that degrade zinc-finger transcription factors, such as Ikaros and Aiolos, resulting in the restoration of Type 1 IFN signaling pathway which is also relevant in lymphoma. By combining the activity of the IMiDs with the IRAK4 degradation in a single agent addresses both the IL-1/TLR and the Type 1 IFN pathways synergistically while also demonstrating broad activity against MYD88-mutant B-cell lymphomas.

A need exists to develop dosing and schedules for IRAKIMiD degraders, which synergistically combine the activity of both IRAK4 and IMiD substrate degradation to exploit complimentary pathway signaling, to improve upon the efficacy of IRAK4 kinase inhibitors and other therapies and provide single-agent activity in MYD88-mutant B-cell lymphoma.

SUMMARY OF THE INVENTION

It has been found that certain IRAK4 degraders are suitable for enteral and parental administration in a patient for treating a MYD88-mutated B-cell lymphoma. Accordingly, in one aspect, the present invention provides a method of treating a MYD88-mutant B-cell lymphoma in a patient in need thereof, comprising administering a therapeutically effective amount of Compound A or a pharmaceutically acceptable salt thereof to the patient, wherein Compound A is N-(2-(((1r,4r)-4-((6-(2-((-2(2,6-dioxopiperidin-3-yl)-1,3-dioxoisoindolin-4-yl) amino)ethyl)-2-azaspiro[3.3]heptan-2-yl) methyl)cyclohexyl)-5-(2-hydroxypropan-2-yl)benzo[d]thiazol-6-yl)-6-(trifluoromethyl)picolinamide In one aspect, Compound A or a pharmaceutically acceptable salt thereof is administered at a dose of up to 300 mg, up to 400 mg, up to 900 mg, or up to 1600 mg to the patient. In other aspects, Compound A or a pharmaceutically acceptable salt thereof is administered at a dose of from about 300 mg to about 900 mg or from about 100 mg to about 300 mg. In some instances, Compound A or a pharmaceutically acceptable salt thereof is administered at a dose of from about 30 mg/m$^2$ to about 90 mg/m$^2$ or from about 10 mg/m$^2$ to about 40 mg/m$^2$.

In one aspect, Compound A or a pharmaceutically acceptable salt thereof is administered orally to the patient. The oral administration of Compound A to the patient can include Compound A in solutions, suspensions, emulsions, tablets, pills, capsules, powders, or sustained-release formulations. In other aspect, Compound A or a pharmaceutically acceptable salt thereof is administered intravenously to the patient. The intravenous administration of Compound A to the patient can include Compound A in sterile injectable solutions.

In one aspect, Compound A or a pharmaceutically acceptable salt thereof is administered to the patient once weekly (QW) or twice weekly (BIW). For biweekly dosing, the administration of Compound A or a pharmaceutically acceptable salt thereof can be on day 1 and day 2 of the week or on day 1 and day 4 of the week. In some embodiments, Compound A or a pharmaceutically acceptable salt thereof is administered to the patient once or twice weekly in week 1 and week 2 in a 3 week administration cycle. In some embodiments, Compound A or a pharmaceutically acceptable salt thereof is administered to the patient once or twice weekly in week 1 and week 2 in a 4 week administration cycle. In some embodiments, Compound A or a pharmaceutically acceptable salt thereof is administered to the patient once or twice weekly in week 1 and week 2 in a 4 week administration cycle. In some embodiments, Compound A or a pharmaceutically acceptable salt thereof is administered to the patient once or twice weekly in week 1 and week 3 in a 4 week administration cycle. In some embodiments, Compound A or a pharmaceutically acceptable salt thereof is administered to the patient once or twice weekly in weeks 1-3 in a 4 week administration cycle.

Also provided herein, is a pharmaceutical composition comprising Compound A or a pharmaceutically acceptable salt thereof, and one or more pharmaceutically acceptable excipient or carrier. In some aspects, the one or more pharmaceutically acceptable excipient or carrier includes one or more diluents, preservatives, binders, lubricants, disintegrators, swelling agents, fillers, or stabilizers. In other aspects, the one or more pharmaceutically acceptable excipient or carrier includes one or more buffers, surfactants, dispersants, emulsifiers, or viscosity modifying agents.

In further aspects, the MYD88-mutant B-cell lymphoma is selected from ABC DLBCL, primary CNS lymphomas, primary extranodal lymphomas, Waldenström macroglobulinemia, Hodgkin's lymphoma, primary cutaneous T-cell lymphoma and chronic lymphocytic leukemia. In some embodiments, the patient receiving Compound A or a pharmaceutically acceptable salt thereof to treat a MYD88-mutant B-cell lymphoma has received at least one prior therapy. In some embodiments, the patient is a human.

These and other aspects of this disclosure will be apparent upon reference to the following detailed description. To this end, various references are set forth herein which describe in more detail certain background information and procedures and are each hereby incorporated by reference in their entirety.

DETAILED DESCRIPTION OF CERTAIN EMBODIMENTS

Figure 1:
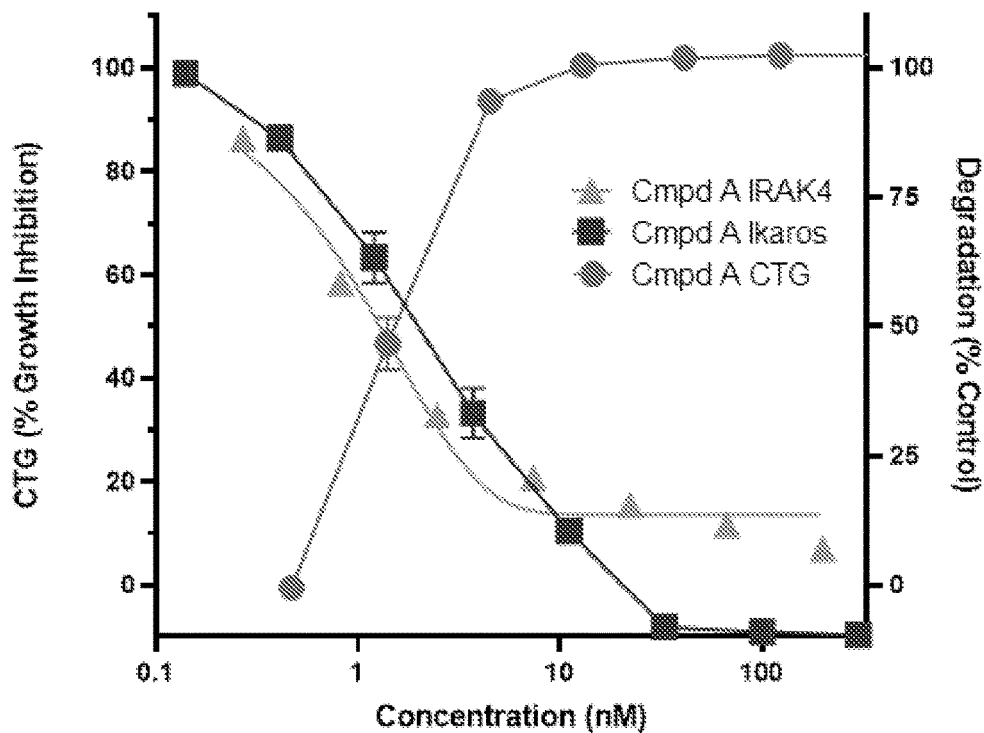
FIG. 1 shows that Compound A is an approximately equipotent degrader of IRAK4 and Ikaros with approximately 70% degradation of both IRAK4 and Ikaros associated with CTG $IC_{90}$. Short exposure of Compound A (72 hrs) shows cell killing in vitro, differentiated from IMiDs.
Figure 1:
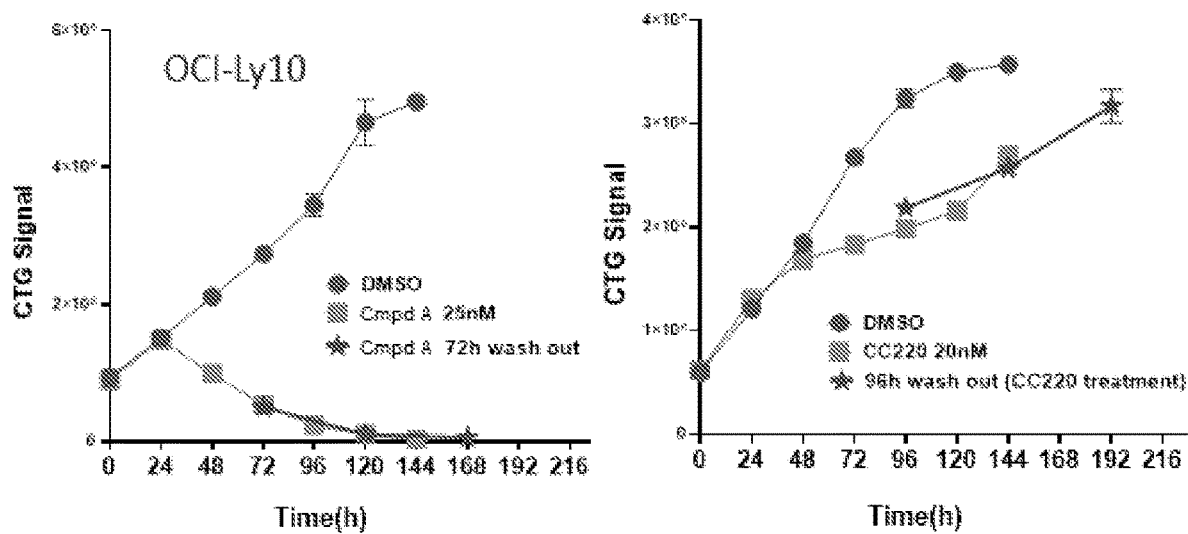

1. General Description of Certain Embodiments of the Invention

The IRAK4 degraders provided herein are heterobifunctional small molecule therapeutic targeting CRBN E3 ligase and IRAK4 to mediate the selective degradation of IRAK4 protein as well as IMiD targets, including Ikaros and Aiolos.

In MYD88-mutant B-cell lymphoma, degradation of the Myddosome component IRAK4, in combination with IMiD-mediated degradation of Ikaros and Aiolos and the resulting downregulation of IRF4 and activation of an interferon-like response, will synergize to induce cell death and antitumor responses. In certain embodiments, provided herein is a treatment of adult patients with MYD88-mutant B cell lymphoma who have received at least one prior therapy. The IRAK4 degraders of the current invention are provided by oral and intravenous administration at the doses and schedules described herein.

In the following disclosure, certain specific details are set forth in order to provide a thorough understanding of various embodiments. However, one skilled in the art will understand that the methods and uses described herein may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

2. Definitions

As used in the specification and appended claims, unless specified to the contrary, the following terms and abbreviations have the following meanings.

As used herein, the term "about" refers to within 20% of a given value. In some embodiments, the term "about" refers to within 20%, 19%, 18%, 17%, 16%, 15%, 14%, 13%, 12%, 11%, 10%, 9%, 8%, 7%, 6%, 5%, 4%, 3%, 2%, or 1% of a given value.

As used herein, the term "Compound A" refers to N-(2-((1r,4r)-4-((6-(2-((2-(2,6-dioxopiperidin-3-yl)-1,3-dioxoisoindolin-4-yl) amino)ethyl)-2-azaspiro[3.3]heptan-2-yl)methyl)cyclohexyl)-5-(2-hydroxypropan-2-yl)benzo[d]thiazol-6-yl)-6-(trifluoromethyl)picolinamide having the formula:

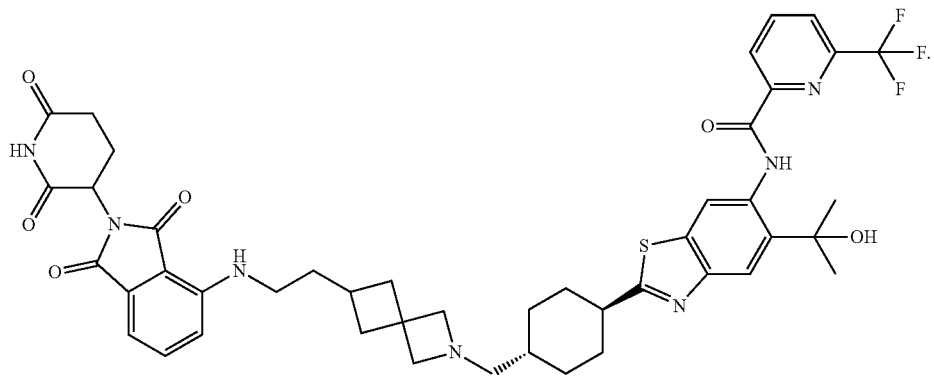

In some embodiments, Compound A or a pharmaceutically acceptable salt thereof, is in amorphous form. In some embodiments, Compound A or a pharmaceutically acceptable salt thereof, is in crystalline form.

As used herein, the term "Compound (R)-A" refers to N-(2-((1r,4r)-4-((6-(2-((2-((R)-2,6-dioxopiperidin-3-yl)-1,3-dioxoisoindolin-4-yl) amino)ethyl)-2-azaspiro[3.3]heptan-2-yl) methyl)cyclohexyl)-5-(2-hydroxypropan-2-yl)benzo[d]thiazol-6-yl)-6-(trifluoromethyl)picolinamide having the formula:

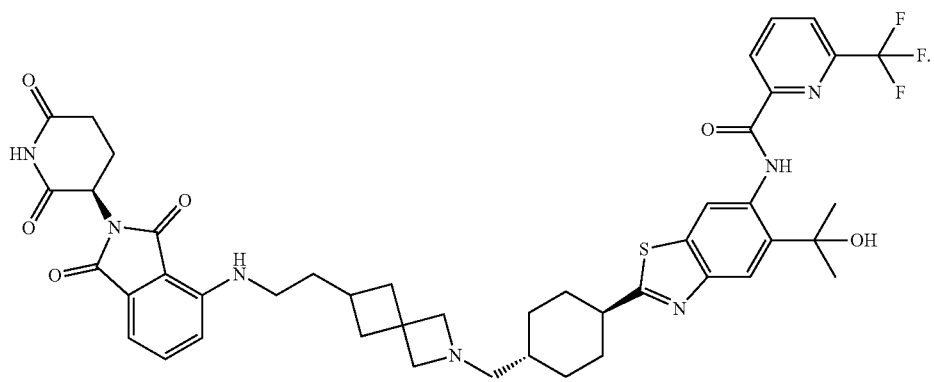 [SMILES: CC(C)(O)c1cc2nc([C@H]3CC[C@H](CN4CC5(CC(CCNc6cccc7c6C(=O)N([C@@H]6CCC(=O)NC6=O)C7=O)C5)C4)CC3)sc2cc1NC(=O)c1cccc(C(F)(F)F)n1]

In some embodiments, Compound (R)-A or a pharmaceutically acceptable salt thereof, is in amorphous form. In some embodiments, Compound (R)-A or a pharmaceutically acceptable salt thereof, is in crystalline form.

As used herein, the term "Compound (S)-A" refers to N-(2-((1r,4r)-4-((6-(2-((2-((S)-2,6-dioxopiperidin-3-yl)-1,3-dioxoisoindolin-4-yl) amino)ethyl)-2-azaspiro[3.3]heptan-2-yl) methyl)cyclohexyl)-5-(2-hydroxypropan-2-yl)benzo[d]thiazol-6-yl)-6-(trifluoromethyl)picolinamide having the formula:

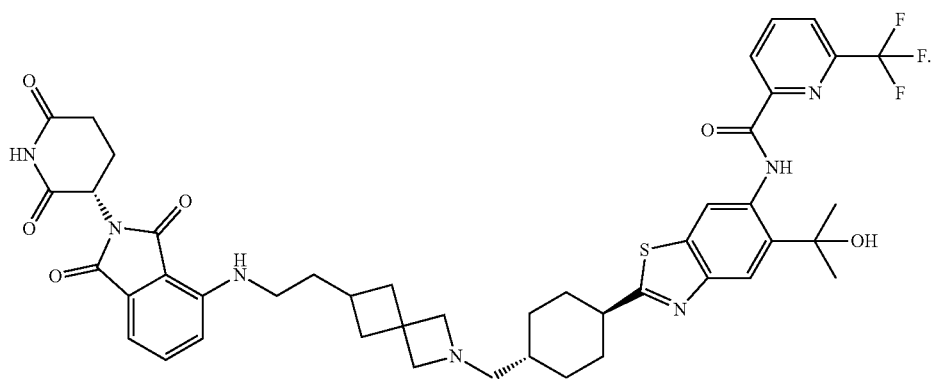 [SMILES: CC(C)(O)c1cc2nc([C@H]3CC[C@H](CN4CC5(CC(CCNc6cccc7c6C(=O)N([C@H]6CCC(=O)NC6=O)C7=O)C5)C4)CC3)sc2cc1NC(=O)c1cccc(C(F)(F)F)n1]

In some embodiments, Compound (S)-A or a pharmaceutically acceptable salt thereof, is in amorphous form. In some embodiments, Compound (S)-A or a pharmaceutically acceptable salt thereof, is in crystalline form.

As used herein, the term "Compound B" refers to a compound of formula

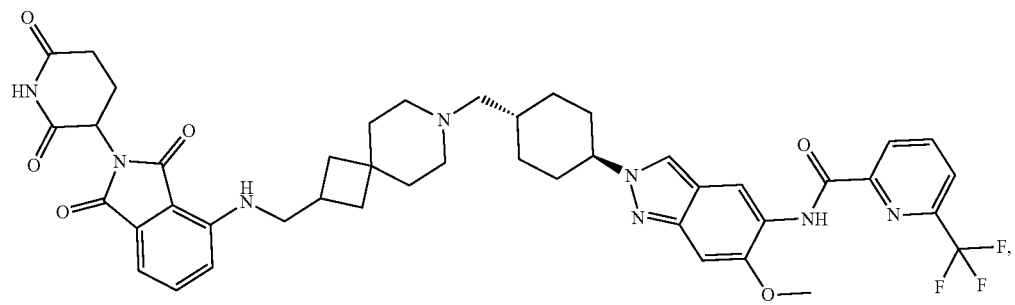 [SMILES: COc1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1cccc(C(F)(F)F)n1]

or a pharmaceutically acceptable salt thereof.

As used herein, the term "inhibitor" is defined as a compound that binds to and/or inhibits an IRAK kinase with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

As used herein, the term "IRAK4 degrader" refers to an agent that degrades IRAK4 and other IMiD targets. Various IRAK4 degraders have been described previously, for example, in WO 2019/133531 and WO 2020/010227, the contents of each of which are incorporated herein by reference in their entireties. In certain embodiments, an IRAK4 degrader has an $DC_{50}$ of less than about 50 µM, less than about 1 µM, less than about 500 nM, less than about 100 nM, less than about 10 nM, or less than about 1 nM.

The term "patient," as used herein, means an animal, preferably a mammal, and most preferably a human.

As used herein, the term "mg/kg" or "mpk" refers to the milligram of medication (for example, Compound A) per kilogram of the body weight of the subject taking the medication. As provided by the FDA guidance, a dose in mg/kg in an animal can be converted to a dose in mg/m², and to a corresponding Human Equivalent Dose (HED), by multiplying, or dividing, the corresponding factor as shown in the following table:

| Species | To Convert Animal Dose in mg/kg to Dose in mg/m², Multiply by $k_m$ | To Convert Animal Dose in mg/kg to HED[a] in mg/kg, Either: | |
|---|---|---|---|
| | | Divide Animal Dose By | Multiply Animal Dose By |
| Human | 37 | — | — |
| Child (20 kg)[b] | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys[c] | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

[a]Assumes 60 kg human. For species not listed or for weights outside the standard ranges, HED can be calculated from the following formula: HED = animal dose in mg/kg × (animal weight in kg/human weight in kg)$^{0.33}$.
[b]This $k_m$ value is provided for reference only since healthy children will rarely be volunteers for phase 1 trials.
[c]For example, cynomolgus, rhesus, and stumptail.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention The term "pharmaceutically acceptable excipient or carrier" refers to a non-toxic excipient or carrier that does not destroy the pharmacological activity of the compound with which it is formulated. Pharmaceutically acceptable excipient or carrier that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "therapeutically effective amount" as used herein refers to an amount of IRAK4 degrader that is sufficient to treat the stated disease, disorder, or condition or have the desired stated effect on the disease, disorder, or condition or one or more mechanisms underlying the disease, disorder, or condition in a subject. In certain embodiments, when Compound A is administered for the treatment of a MYD88-mutant B cell lymphoma, therapeutically effective amount refers an amount of Compound A which, upon administration to a subject, treats or ameliorates the lymphoma in the subject, or exhibits a detectable therapeutic effect in the subject that results in partial to complete tumor regression.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

3. Description of Exemplary Embodiments

According to one aspect, the invention provides a method for treating a MYD88-mutant B-cell lymphoma in a patient in need thereof, comprising administering a therapeutically effective amount of an IRAK4 degrader (e.g., Compound A), or a pharmaceutically acceptable salt thereof. In some embodiments, the method comprises administering up to 1600 mg of an IRAK4 degrader (e.g., Compound A), or a pharmaceutically acceptable salt thereof in a single or divided dose.

Pharmaceutically Acceptable Compositions

According to one embodiment, the invention provides a composition comprising an IRAK4 degrader of this invention (e.g., Compound A) or a pharmaceutically acceptable derivative thereof and a pharmaceutically acceptable excipient or carrier. The amount of IRAK4 degrader in compositions of this invention is such that it is effective to measurably degrade and/or inhibit IRAK4 protein kinase, or a mutant thereof, in a patient. In certain embodiments, a composition of this invention is formulated for administration to a patient in need of such composition. In some embodiments, a composition of this invention is formulated for oral administration to a patient. In some embodiments, a composition of this invention is formulated for intravenous administration to a patient.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular IRAK4 degrader in the composition.

Compositions

The dosage forms disclosed herein include pharmaceutically acceptable salts of an IRAK4 degraders (e.g., Compound A). In some embodiments, the dosage forms can be formulated for enteral or parenteral administration. The IRAK4 degrader can be combined with one or more pharmaceutically acceptable carriers that are considered safe and effective to form a unit dosage as described herein, and may be administered to an individual without causing undesirable biological side effects or unwanted interactions.

These dosage forms can take the form of solutions, suspensions, emulsion, tablets, pills, capsules, powders, sustained-release formulations and the like.

In one preferred embodiment, the dosage form is in the form of a tablet, including an IRAK4 degraders (e.g., Compound A). The dosage form is administered to the subject in need thereof, for a time period effective to ameliorate the patient condition (e.g., a MYD88 mutant B-cell lymphoma).

Excipients and Carriers

Pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions.

Suitable pharmaceutical excipients include starch, glucose, sucrose, gelatin, lactose, malt, rice, flour, chalk, silica gel, sodium stearate, glycerol monostearate, talc, sodium chloride, glycerol, propylene, glycol, water, ethanol and the like. The pharmaceutical composition may also contain wetting or emulsifying agents or suspending/diluting agents, or pH buffering agents, or agents for modifying or maintaining the rate of release of the disclosed salts, all of which are disclosed further herein.

Administration and Dosage

As described herein, the IRAK4 degraders provided herein are administered by parenteral and enteral routes. In some embodiments, an IRAK4 degrader (e.g., Compound A) or a pharmaceutically acceptable salt thereof, is administered intravenously. In some embodiments, an IRAK4 degrader (e.g., Compound A) or a pharmaceutically acceptable salt thereof is administered by an IV injection. In some embodiments, an IRAK4 degrader (e.g., Compound A) or a pharmaceutically acceptable salt thereof is administered by an IV infusion.

As described herein, an IRAK4 degrader (e.g., Compound A) or a pharmaceutically acceptable salt thereof, is administered enterally. In some embodiments, an IRAK degraders (e.g., Compound A) or a pharmaceutically acceptable salt thereof is administered in amorphous or in crystalline form (e.g., pressed into pills or in capsules). In some embodiments, an IRAK4 degrader (e.g., Compound A) or a pharmaceutically acceptable salt thereof is administered as a lyophilized powder.

In some embodiments, a method of the invention comprises orally administering to a patient a pharmaceutical composition comprising an IRAK degrader. In some embodiments, a pharmaceutical composition is a solid pharmaceutical composition. In some embodiments, the solid pharmaceutical composition is a powder. In some embodiments, the pharmaceutical composition is lyophilized powder. In some embodiments, the solid pharmaceutical composition is granules. In some embodiments, the solid pharmaceutical composition of the invention is tablets. In some embodiments, the solid pharmaceutical composition is capsules. In some embodiments, the solid pharmaceutical composition is pills. In some embodiments, the solid pharmaceutical composition is suspensions. In some embodiments, the solid pharmaceutical composition is emulsions. In some embodiments, the solid pharmaceutical composition is solutions.

In some embodiments, the methods and uses described herein, such as the method of or use in treating MYD88 mutant B-cell lymphoma in a patient in need thereof, is achieved by administering (e.g., orally or intravenously) a therapeutically effective amount of an IRAK4 degrader (e.g., Compound A), such as up to 1600 mg of Compound A in a single or multiple dosage units. In some embodiments, the method can include administering (e.g., orally or intravenously), in a single or multiple dosage units ranging from about 10 to about 1600 mg/dosage form, such as about 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or about 1000 mg. For example, an enteric tablet form can include 100 mg, 150 mg, 200 mg, 250 mg, 300 mg, 350 mg, 400 mg, 450 mg, or 500 mg/dosage form of an IRAK4 degrader (e.g., Compound A) or a pharmaceutically acceptable salt thereof.

In some embodiments, Compound A or a pharmaceutically acceptable salt thereof is intravenously administered at a dose of up to 300 mg to the patient. In some embodiments, Compound A or a pharmaceutically acceptable salt thereof is intravenously administered at a dose of up to 400 mg to the patient. In some embodiments, Compound A or a pharmaceutically acceptable salt thereof is orally administered at a dose of up to 900 mg to the patient. In some embodiments, Compound A or a pharmaceutically acceptable salt thereof is orally administered at a dose of up to 1600 mg to the patient. In some embodiments, Compound A or a pharmaceutically acceptable salt thereof is orally administered at a dose of from about 300 mg to about 900 mg. In some embodiments, Compound A or a pharmaceutically acceptable salt thereof is intravenously administered at a dose of from about 100 mg to about 400 mg.

In some embodiments, a pharmaceutical composition is provided, wherein, the pharmaceutically composition comprises 50 mg to about 600 mg of Compound A, or a pharmaceutically acceptable salt thereof, and one or more pharmaceutically acceptable excipient or carrier. In some embodiments, a pharmaceutical composition is provided, wherein, the pharmaceutically composition comprises 100 mg to about 400 mg of Compound A, or a pharmaceutically acceptable salt thereof, and one or more pharmaceutically acceptable excipient or carrier. In some embodiments, a pharmaceutical composition is provided, wherein, the pharmaceutically composition comprises 300 mg to about 900 mg of Compound A, or a pharmaceutically acceptable salt thereof, and one or more pharmaceutically acceptable excipient or carrier.

In some embodiments (for example, as described in Example 6), Compound A, or a pharmaceutically acceptable salt thereof, or a pharmaceutical composition thereof, is administered to a mouse at a dose of up to about 60 mg/kg for oral administration, which corresponds to up to about 180 mg/m$^2$ according to the FDA guidance as described above. Accordingly, in some embodiments, Compound A, or a pharmaceutically acceptable salt thereof, or a pharmaceutical composition thereof, is administered orally to a patient at a dose of up to about 180 mg/m$^2$. In some embodiments, Compound A, or a pharmaceutically acceptable salt thereof, or a pharmaceutical composition thereof, is administered orally to a patient at a dose of up to about 135 mg/m$^2$, or up to about 90 mg/m$^2$, or up to about 60 mg/m$^2$, or up to about 30 mg/m$^2$. In some embodiments, Compound A, or a pharmaceutically acceptable salt thereof, or a pharmaceutical composition thereof, is administered orally to a patient at a dose of about 10 mg/m$^2$ to about 30 mg/m$^2$, or about 10 mg/m$^2$ to about 60 mg/m$^2$, or about 30 mg/m$^2$ to about 60 mg/m$^2$, or about 10 mg/m$^2$ to about 90 mg/m$^2$, or about 30 mg/m$^2$ to about 90 mg/m$^2$, or about 60 mg/m$^2$ to about 90 mg/m$^2$, or about 10 mg/m$^2$ to about 135 mg/m$^2$, or about 30 mg/m$^2$ to about 135 mg/m$^2$, or about 60 mg/m$^2$ to about 135 mg/m$^2$, or about 90 mg/m$^2$ to about 135 mg/m$^2$, or about 10 mg/m$^2$ to about 180 mg/m$^2$, or about 30 mg/m$^2$ to about 180 mg/m$^2$, or about 60 mg/m$^2$ to about 180 mg/m$^2$, or about 90 mg/m$^2$ to about 180 mg/m$^2$, or about 135 mg/m$^2$ to about 180 mg/m$^2$. In some embodiments, Compound A, or a pharmaceutically acceptable salt thereof, or a pharmaceutical composition thereof, is administered orally to a patient at a dose of about 180 mg/m$^2$, about 165 mg/m$^2$, about 150 mg/m$^2$, about 135 mg/m$^2$, about 120 mg/m$^2$, about 105 mg/m$^2$, about 90 mg/m$^2$, about 75 mg/m$^2$, about 60 mg/m$^2$, about 45 mg/m$^2$, about 30 mg/m$^2$, or about 15 mg/m$^2$.

In some embodiments (for example, as described in Example 6), Compound A, or a pharmaceutically acceptable salt thereof, or a pharmaceutical composition thereof, is administered to a mouse at a dose of up to about 12 mg/kg for intravenous administration, which corresponds to up to about 36 mg/m$^2$ according to the FDA guidance as described above. Accordingly, in some embodiments, Compound A, or a pharmaceutically acceptable salt thereof, or a pharmaceutical composition thereof, is administered intravenously to a patient at a dose of up to about 36 mg/m$^2$. In some embodiments, Compound A, or a pharmaceutically acceptable salt thereof, or a pharmaceutical composition thereof, is administered intravenously to a patient at a dose of up to about 27 mg/m$^2$, or up to about 18 mg/m$^2$, or up to about 9 mg/m$^2$. In some embodiments, Compound A, or a pharmaceutically acceptable salt thereof, or a pharmaceutical composition thereof, is administered intravenously to a patient at a dose of about 3 mg/m$^2$ to about 9 mg/m$^2$, or about 3 mg/m$^2$ to about 18 mg/m$^2$, or about 9 mg/m$^2$ to about 18 mg/m$^2$, or about 3 mg/m$^2$ to about 27 mg/m$^2$, or about 9 mg/m$^2$ to about 27 mg/m$^2$, or about 18 mg/m$^2$ to about 27 mg/m$^2$, or about 3 mg/m$^2$ to about 36 mg/m$^2$, or about 9 mg/m$^2$ to about 36 mg/m$^2$, or about 18 mg/m$^2$ to about 36 mg/m$^2$, or about 27 mg/m$^2$ to about 36 mg/m$^2$. In some embodiments, Compound A, or a pharmaceutically acceptable salt thereof, or a pharmaceutical composition thereof, is administered intravenously to a patient at a dose of about 36 mg/m$^2$, about 33 mg/m$^2$, about 30 mg/m$^2$, about 27 mg/m$^2$, about 24 mg/m$^2$, about 21 mg/m$^2$, about 18 mg/m$^2$, about 15 mg/m$^2$, about 12 mg/m$^2$, about 9 mg/m$^2$, about 6 mg/m$^2$, or about 3 mg/m$^2$.

In some embodiments (for example, as described in Example 7), Compound A, or a pharmaceutically acceptable salt thereof, or a pharmaceutical composition thereof, is administered to a monkey at a dose of up to about 100 mg/kg for oral administration, which corresponds to up to about 35 mg/kg Human Equivalent dose (HED) according to the FDA guidance as described above. Accordingly, in some embodiments, Compound A, or a pharmaceutically acceptable salt thereof, or a pharmaceutical composition thereof, is administered orally to a patient at a dose of up to about 35 mg/kg. In some embodiments, Compound A, or a pharmaceutically acceptable salt thereof, or a pharmaceutical composition thereof, is administered orally to a patient at a dose of up to about 26 mg/kg, or up to about 18 mg/kg, or up to about 9 mg/kg. In some embodiments, Compound A, or a pharmaceutically acceptable salt thereof, or a pharmaceutical composition thereof, is administered orally to a patient at a dose of about 9 mg/kg to about 18 mg/kg, or about 9 mg/kg to about 26 mg/kg, or about 18 mg/kg to about 26 mg/kg, or about 9 mg/kg to about 35 mg/kg, or about 18 mg/kg to about 35 mg/kg, or about 26 mg/kg to about 35 mg/kg. In some embodiments, Compound A, or a pharmaceutically acceptable salt thereof, or a pharmaceutical composition thereof, is administered orally to a patient at a dose of about 35 mg/kg, about 30 mg/kg, about 25 mg/kg, about 20 mg/kg, about 15 mg/kg, about 10 mg/kg, or about 5 mg/kg.

In some embodiments (for example, as described in Example 7), Compound A, or a pharmaceutically acceptable salt thereof, or a pharmaceutical composition thereof, is administered to a monkey at a dose of up to about 100 mg/kg for oral administration, which corresponds to up to about 1200 mg/m$^2$ according to the FDA guidance as described above. Accordingly, in some embodiments, Compound A, or a pharmaceutically acceptable salt thereof, or a pharmaceutical composition thereof, is administered orally to a patient at a dose of up to about 1200 mg/m$^2$. In some embodiments, Compound A, or a pharmaceutically acceptable salt thereof, or a pharmaceutical composition thereof, is administered orally to a patient at a dose of up to about 900 mg/m$^2$, or up to about 600 mg/m$^2$, or up to about 300 mg/m$^2$, or up to about 150 mg/m$^2$. In some embodiments, Compound A, or a pharmaceutically acceptable salt thereof, or a pharmaceutical composition thereof, is administered orally to a patient at a dose of about 150 mg/m$^2$ to about 300 mg/m$^2$, or about 150 mg/m$^2$ to about 600 mg/m$^2$, or about 300 mg/m$^2$ to about 600 mg/m$^2$, or about 150 mg/m$^2$ to about 900 mg/m$^2$, or about 300 mg/m$^2$ to about 900 mg/m$^2$, or about 600 mg/m$^2$ to about 900 mg/m$^2$, or about 150 mg/m$^2$ to about 1200 mg/m$^2$, or about 300 mg/m$^2$ to about 1200 mg/m$^2$, or about 600 mg/m$^2$ to about 1200 mg/m$^2$, or about 900 mg/m$^2$ to about 1200 mg/m$^2$. In some embodiments, Compound A, or a pharmaceutically acceptable salt thereof, or a pharmaceutical composition thereof, is administered orally to a patient at a dose of about 150 mg/m$^2$, about 200 mg/m$^2$, about 250 mg/m$^2$, about 300 mg/m$^2$, about 350 mg/m$^2$, about 400 mg/m², about 450 mg/m², about 500 mg/m², about 550 mg/m², about 600 mg/m², about 650 mg/m², about 700 mg/m², about 750 mg/m², about 800 mg/m², about 850 mg/m², about 900 mg/m², about 950 mg/m², about 1000 mg/m², about 1050 mg/m², about 1100 mg/m², about 1150 mg/m², or about 1200 mg/m².

In some embodiments (for example, as described in Example 7), Compound A, or a pharmaceutically acceptable salt thereof, or a pharmaceutical composition thereof, is administered to a monkey at a dose of up to about 20 mg/kg for intravenous administration, which corresponds to up to about 10 mg/kg HED according to the FDA guidance as described above. Accordingly, in some embodiments, Compound A, or a pharmaceutically acceptable salt thereof, or a pharmaceutical composition thereof, is administered intravenously to a patient at a dose of up to about 10 mg/kg. In some embodiments, Compound A, or a pharmaceutically acceptable salt thereof, or a pharmaceutical composition thereof, is administered intravenously to a patient at a dose of up to about 8 mg/kg, up to about 6 mg/kg, up to about 5 mg/kg, up to about 4 mg/kg, or up to about 2 mg/kg. In some embodiments, Compound A, or a pharmaceutically acceptable salt thereof, or a pharmaceutical composition thereof, is administered intravenously to a patient at a dose of about 2 mg/kg to about 4 mg/kg, about 2 mg/kg to about 6 mg/kg, about 4 mg/kg to about 6 mg/kg, about 2 mg/kg to about 8 mg/kg, about 4 mg/kg to about 8 mg/kg, about 6 mg/kg to about 8 mg/kg, about 2 mg/kg to about 10 mg/kg, about 4 mg/kg to about 10 mg/kg, about 6 mg/kg to about 10 mg/kg, or about 8 mg/kg to about 10 mg/kg. In some embodiments, Compound A, or a pharmaceutically acceptable salt thereof, or a pharmaceutical composition thereof, is administered intravenously to a patient at a dose of about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.

In some embodiments (for example, as described in Example 7), Compound A, or a pharmaceutically acceptable salt thereof, or a pharmaceutical composition thereof, is administered to a monkey at a dose of up to about 20 mg/kg for intravenous administration, which corresponds to up to about 240 mg/m² according to the FDA guidance as described above. Accordingly, in some embodiments, Compound A, or a pharmaceutically acceptable salt thereof, or a pharmaceutical composition thereof, is administered intravenously to a patient at a dose of up to about 240 mg/m². In some embodiments, Compound A, or a pharmaceutically acceptable salt thereof, or a pharmaceutical composition thereof, is administered intravenously to a patient at a dose of up to about 180 mg/m², up to about 120 mg/m², or up to about 60 mg/m². In some embodiments, Compound A, or a pharmaceutically acceptable salt thereof, or a pharmaceutical composition thereof, is administered intravenously to a patient at a dose of about 60 mg/m² to about 120 mg/m², about 60 mg/m² to about 180 mg/m², about 120 mg/m² to about 180 mg/m², about 60 mg/m² to about 240 mg/m², about 120 mg/m² to about 240 mg/m², or about 180 mg/m² to about 240 mg/m². In some embodiments, Compound A, or a pharmaceutically acceptable salt thereof, or a pharmaceutical composition thereof, is administered intravenously to a patient at a dose of about 240 mg/m², about 220 mg/m², about 200 mg/m², about 180 mg/m², about 160 mg/m², about 140 mg/m², about 120 mg/m², about 100 mg/m², about 80 mg/m², about 60 mg/m², about 40 mg/m², about 20 mg/m², or about 10 mg/m².

In some embodiments, Compound A, or a pharmaceutically acceptable salt thereof, or a pharmaceutical composition thereof, is orally or intravenously administered at a dosage to achieve one or more of the pharmacokinetics properties as described in the Examples, for example, the AUC as listed in tables 11 and 12 in Example 7.

Dosing Schedule

As provided in view of preclinical data described herein, an IRAK4 degrader (e.g., Compound A) or a pharmaceutically acceptable salt thereof, or a pharmaceutical composition thereof, is administered to a patient at a dosing schedule appropriate to give the desired tumor regression effect with minimum side effects. In some embodiments, the IRAK degrader or pharmaceutical composition thereof is administered to a patient once every 1, 2, 3, 4, 5, 6, or 7 days. In some embodiments, a pharmaceutical composition of the invention is administered to a patient biweekly (BIW). Biweekly doses can be administered hours apart (e.g., 1, 3, 6, 12 hours) or days apart (e.g., 1, 2, 3, or 4 days). In some embodiments, biweekly doses are administered on day 1 and day 2. In some embodiments, biweekly doses are administered on day 1 and day 4. In some embodiments, a pharmaceutical composition of the invention is administered to a patient weekly (QW).

Figure 4:
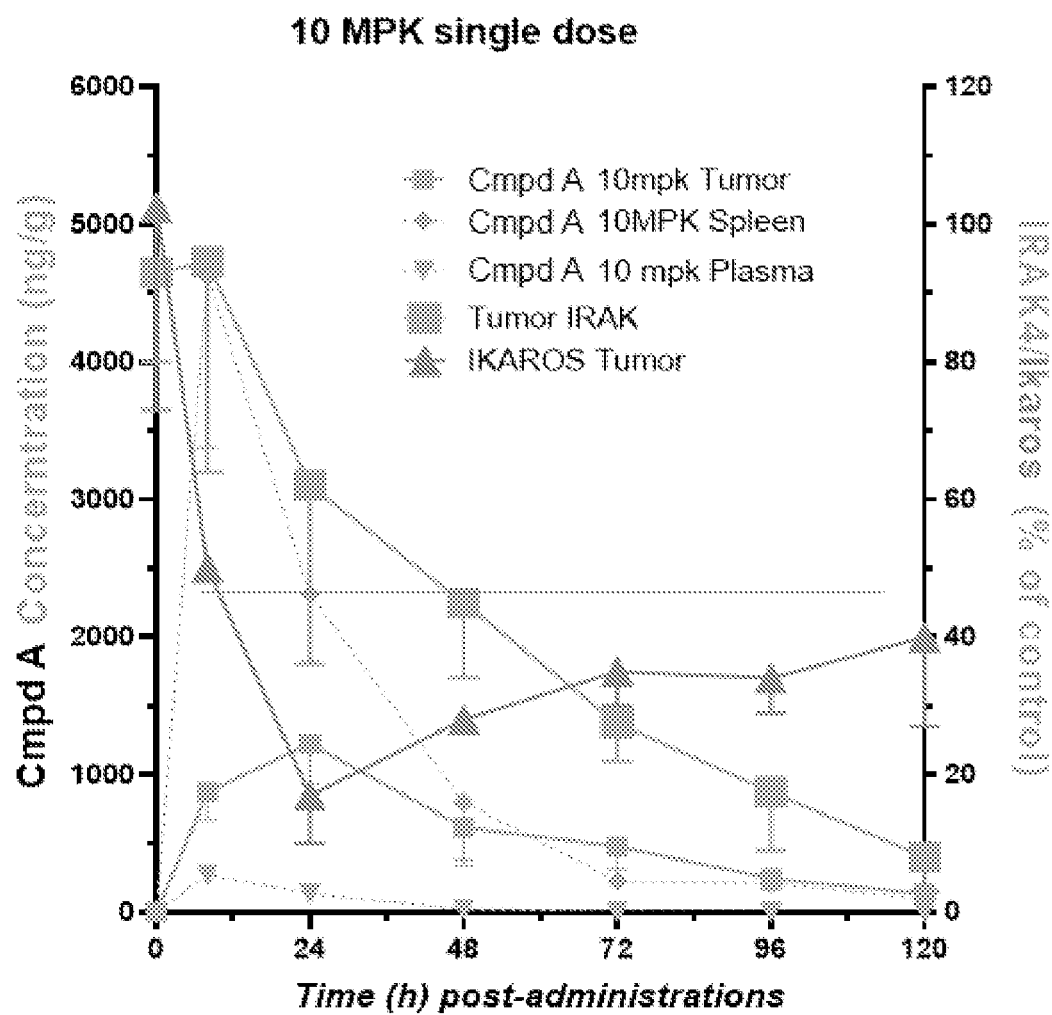
FIG. 4 shows that Compound A gives sustained tumor PD effect in OCI-Ly10, supporting target coverage from intermittent dosing.

It has also been found that Compound A gives high tissue exposure relative to plasma and sustained PD effect following a single dose, and that tumor shows relatively slower clearance compared to spleen, which has $C_L$ similar to plasma (see, for example, Example 6 and FIG. 4). Accordingly, in some embodiments, Compound A, or a pharmaceutically acceptable salt thereof, or a pharmaceutical composition thereof, is orally or intravenously administered is administered to a patient once every 1, 2, 3, or 4 weeks, or once every 7, 10, 14, 17, 21, 24, or 28 days.

As described herein in some embodiments, an IRAK4 degrader (e.g., Compound A) or a pharmaceutically acceptable salt thereof is administered once weekly for two or three out of four weeks. In some embodiments, an IRAK4 degrader (e.g., Compound A) or a pharmaceutically acceptable salt thereof is administered twice weekly for two or three out of four weeks. In some embodiments, an IRAK4 degrader (e.g., Compound A) or a pharmaceutically acceptable salt thereof is administered once weekly for two out of three weeks. In some embodiments, an IRAK4 degrader (e.g., Compound A) or a pharmaceutically acceptable salt thereof is administered twice weekly for two out of three weeks. In some embodiments, an IRAK4 degrader (e.g., Compound A) or a pharmaceutically acceptable salt thereof is administered once weekly every other week out of four weeks. In some embodiments, an IRAK4 degrader (e.g., Compound A) or a pharmaceutically acceptable salt thereof is administered twice weekly every other week out of four weeks.

In some embodiments, an IRAK4 degrader (e.g., Compound A) or a pharmaceutically acceptable salt thereof is administered to the patient once weekly in week 1 and week 2 in a 3 week administration cycle. In some embodiments, an IRAK4 degrader (e.g., Compound A) or a pharmaceutically acceptable salt thereof is administered to the patient once weekly in week 1 and week 2 in a 4 week administration cycle. In some embodiments, an IRAK4 degrader (e.g., Compound A) or a pharmaceutically acceptable salt thereof is administered to the patient once weekly in week 1 and week 2 in a 4 week administration cycle. In some embodiments, an IRAK4 degrader (e.g., Compound A) or a pharmaceutically acceptable salt thereof is administered to the patient once weekly in week 1 and week 3 in a 4 week administration cycle. In some embodiments, an IRAK4 degrader (e.g., Compound A) or a pharmaceutically acceptable salt thereof is administered to the patient once weekly in weeks 1-3 in a 4 week administration cycle.

In some embodiments, an IRAK4 degrader (e.g., Compound A) or a pharmaceutically acceptable salt thereof is administered to the patient twice weekly in week 1 and week 2 in a 3 week administration cycle. In some embodiments, an IRAK4 degrader (e.g., Compound A) or a pharmaceutically acceptable salt thereof is administered to the patient twice weekly in week 1 and week 2 in a 4 week administration cycle. In some embodiments, an IRAK4 degrader (e.g., Compound A) or a pharmaceutically acceptable salt thereof is administered to the patient once weekly in week 1 and week 2 in a 4 week administration cycle. In some embodiments, an IRAK4 degrader (e.g., Compound A) or a pharmaceutically acceptable salt thereof is administered to the patient twice weekly in week 1 and week 3 in a 4 week administration cycle. In some embodiments, an IRAK4 degrader (e.g., Compound A) or a pharmaceutically acceptable salt thereof is administered to the patient twice weekly in weeks 1-3 in a 4 week administration cycle.

Figure 5:
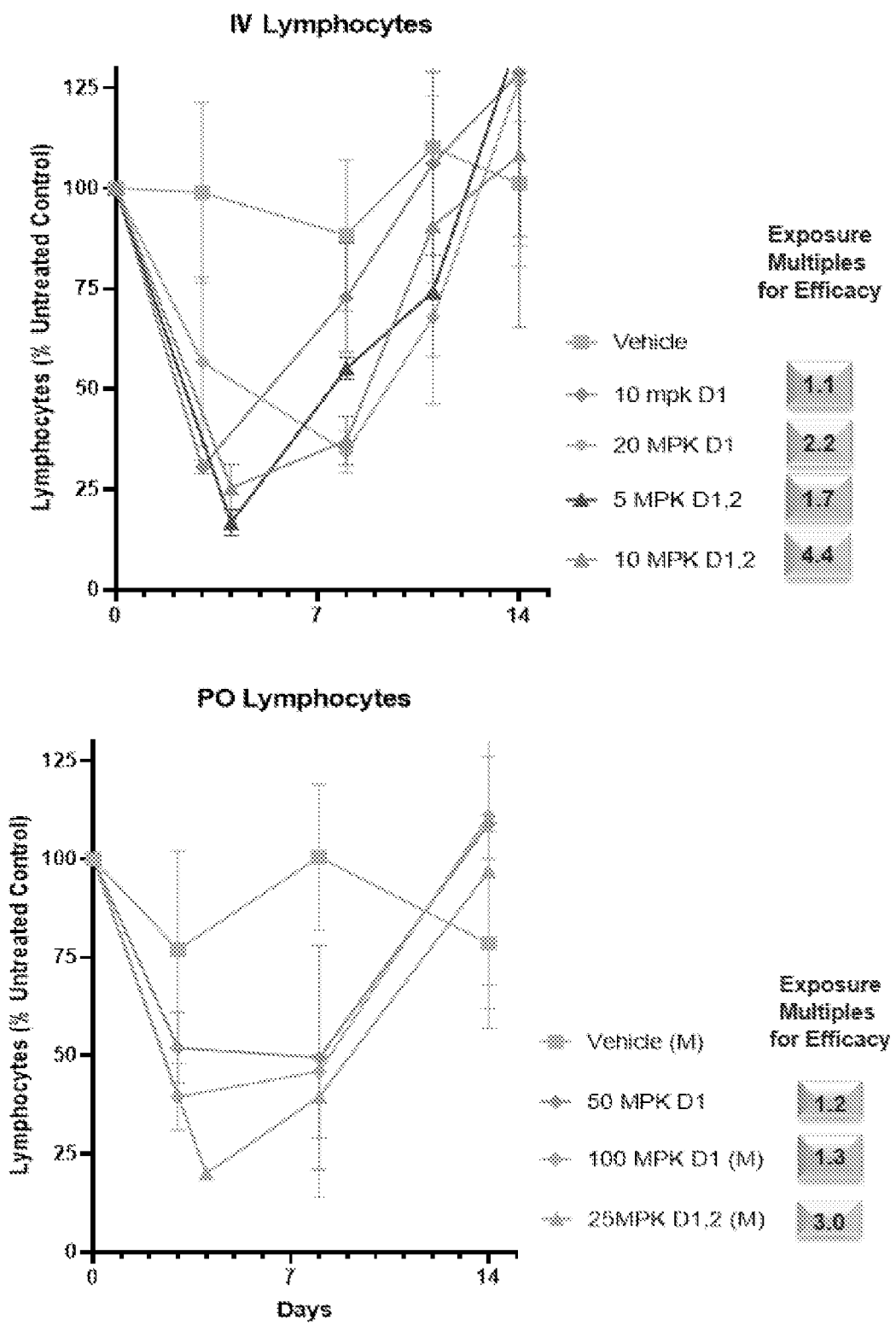
FIG. 5 shows lymphopenia results indicating lymphocyte changes are consistent between IV and PO dosing.

In some embodiments, the dosing schedule is any one of those shown in FIG. 5. In some embodiments, the dosing schedule is any one of those shown in FIG. 6.

In some embodiments, an IV infusion of a pharmaceutical composition of the invention lasts about 5-30 minutes. In some embodiments, an IV infusion of a pharmaceutical composition of the invention lasts about 30-90 minutes. In some embodiments, an IV infusion of a pharmaceutical composition of the invention lasts about 5, 10, 15, 20, 25, 30, 35, 40, 45, 50, 55, 60, 65, 70, 75, 80, 85, or 90 minutes. In some embodiments, an IV infusion of a pharmaceutical composition of the invention lasts about 2, 2.5, 3, 3.5, or 4 hours.

In some embodiments, a pharmaceutical composition of the invention is administered intravenously twice weekly at a dose of about of about 10 mg/m$^2$ to about 40 mg/m$^2$. In some embodiments, a pharmaceutical composition of the invention is administered orally twice weekly at a dose of about 30 mg/m$^2$ to about 90 mg/m$^2$.

In some embodiments, Compound A, or a pharmaceutically acceptable salt thereof, or a pharmaceutical composition thereof, is orally or intravenously administered at a dosing schedule to achieve one or more of the pharmacokinetics properties as described in the Examples, for example, the AUC as listed in tables 11 and 12 in Example 7.

Formulation of Pharmaceutical Compositions

The administration of the IRAK4 degraders of the present invention may be by any suitable means that results in a concentration of the drug that, combined with the other component, is able to ameliorate the patient condition (e.g., a MYD88 mutant lymphoma).

While it is possible for the active ingredients of the combination to be administered as the pure chemical, it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable and adapted for use for treatment with the combination of the present invention.

The drug may be contained in any appropriate amount in any suitable carrier substance, and may be present in an amount of 1-99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose ($LD_{50}$) to median effective dose ($ED_{50}$)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Enteral Use

Oral formulations can include standard carriers such as pharmaceutical grades of mannitol, lactose, sodium saccharine, starch, magnesium stearate, cellulose, magnesium carbonate, etc. Such compositions will contain a therapeutically effective amount of the disclosed salts with a suitable amount of carrier so as to provide the proper form to the patient based on the mode of administration to be used.

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. The preferred formulation is a tablet, preferably including mannitol in a 1:1 ratio mannitol to active agent; with the active agent, however, mannitol can be including a ratio ranging from 2:1 to a ratio of 1:2. The concentration of mannitol is effective to stabilize the formulation. For example, mannitol can make up between 40-70% by weight of the formulation, for example, 40%, 45%, 50%, 55%, 60%, 65% and 70%. Values intermediate to those specifically disclosed are also contemplated, for example, 61, 62, 63, 64, 65, 66, 67, 69, and 69%. Preferred formulations include microcrystalline cellulose at a concentration ranging from 10-30% w/w preferably, between 15 and 26% w/w.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof Carrier also includes all components of the coating composition, which may include plasticizers, pigments, colorants, stabilizing agents, and glidants. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers", are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, AVCEL® (microcrystalline cellulose), ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil, including in a concentration range between 0.5 and 2.6% w/w of the formulation, preferably, between 1 and 2.0%.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Liquids for Oral Administration

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

If for intravenous administration, the compositions are packaged in solutions of sterile isotonic aqueous buffer. Where necessary, the composition may also include a solubilizing agent. The components of the composition are can be either separately or mixed together in unit dosage form, for example, as a dry lyophilized powder (which can be reconstituted before use with a carrier such as saline) or concentrated solution in a hermetically sealed container such as an ampoule or sachet indicating the amount of active agent. If the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to injection.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to buffers, surfactants, dispersants, emulsifiers, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene, and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-laurylβiminodipropionate, myristoamphoacetate, lauryl betaine, and lauryl sulfobetaine. The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

In some embodiments, a buffering agent is at an amount to adjust pH of a pharmaceutical composition of the invention to about 6-8. In some embodiments, a buffering agent is added at an amount of about 0.1-5 mg per mg of IRAK4 degrader (e.g., Compound A), or a pharmaceutically acceptable thereof In some embodiments, a liquid pharmaceutical composition of the invention is at a pH of about 6-8. In some embodiments, a liquid pharmaceutical composition of the invention is at a pH of about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof The powders can be prepared in such a manner that the particles are porous in nature, which can increase dissolution of the particles. Methods for making porous particles are well known in the art.

The parenteral formulations described herein can be formulated for controlled release including immediate release, delayed release, extended release, pulsatile release, and combinations thereof.

In some embodiments, the invention provides a liquid pharmaceutical composition prepared by dissolving a solid pharmaceutical composition of the invention in water. In some embodiments, the invention provides a liquid pharmaceutical composition prepared by dissolving a solid pharmaceutical composition of the invention in an injectable medium (e.g., saline or 5% dextrose). In some embodiments, the invention provides a liquid pharmaceutical composition prepared by reconstitute a solid pharmaceutical composition of the invention in water, followed by dilution with 5% dextrose. In some embodiments, a liquid pharmaceutical composition is diluted into a 5% dextrose IV bag for IV administration. In some embodiments, a liquid pharmaceutical composition in a 5% dextrose IV bag is stored under room temperature (about 20-25° C.) for up to about 4 hours before IV administration. In some embodiments, a liquid pharmaceutical composition in a 5% dextrose IV bag is stored under refrigerated (about 2-8° C.) conditions for up to about 20 hours before IV administration. In some embodiments, a liquid pharmaceutical composition in a 5% dextrose IV bag is stored under refrigerated (about 2-8° C.) conditions for up to about 20 hours, followed by storage under room temperature (about 20-25° C.) for up to about 4 hours, before IV administration.

Uses of Compounds and Pharmaceutically Acceptable Compositions

Compounds and compositions described herein are generally useful for the degradation of kinase activity of one or more enzymes.

In some embodiments, the invention provides IRAK degraders that modulate targeted ubiquitination and degradation of one or more IRAK kinase. In some embodiments, a provided IRAK degrader modulates targeted ubiquitination and degradation of one or more IRAK kinase and one or more additional protein. In some instances, a provided IRAK degrader modulates targeted ubiquitination and degradation of IRAK4 and one, two, three, four, or five additional proteins.

In certain embodiments, the invention provides IRAK degraders that combine IRAK kinase degradation with IKZF1 and IKZF3 degradation. Some of the most commonly employed E3 ligase ligands are thalidomide and its derivatives, lenalidomide and pomalidomide, commonly referred to as IMiDs (immunomodulatory imide drugs). These agents are small-molecule ligands of cereblon (CRBN) (Ito et al. "Identification of a primary target of thalidomide teratogenicity" Science 2010, 327(5971):1345-1350), a substrate adaptor for the ubiquitously expressed cullin ring ligase 4 (CUL4)-RBX1-DDB1-CRBN (CUL4CRBN) E3 ligase. It has been shown that thalidomide interacts with CRBN to form a novel surface, resulting in interactions with neosubstrates such as Ikaros (IKZF1) and Aiolos (IKZF3) and their ubiquitination and subsequent proteasomal degradation (Krönke et al. "Lenalidomide causes selective degradation of IKZF1 and IKZF3 in multiple myeloma cells" Science 2014, 343(6168):301-305; and Lu et al. "The myeloma drug lenalidomide promotes the cereblon-dependent destruction of Ikaros proteins" Science, 2014; 343(6168):305-309). This activity alone has potent antitumor effects in some liquid malignancies, and lenalidomide (Revlimid®) is US Food and Drug Administration approved for the treatment of MCL, multiple myeloma, and myelodysplastic syndromes with deletion of chromosome 5q. Lenalidomide is also undergoing late-stage clinical trials for a number of lymphomas, including MCL and the activated B-cell subtype of diffuse large B-cell lymphoma (ABC DLBCL).

It has been shown that activating MYD88 mutations increase production of beta-IFN, a pro-apoptotic cytokine, in ABC-DLBCL cells (Yang et al. "Exploiting synthetic lethality for the therapy of ABC diffuse large B cell lymphoma" Cancer Cell 2012, 21(6):723-737). The cells are rendered resistant to this effect by a concomitant MYD88-driven activation of NFkB signaling via IRF4 and SPIB transactivating CARD11 (Yang, Cancer Cell 2012). IMiDs are also known to increase the IFN response in MYD88 mutant ABC-DLBCL to levels sufficient to increase apoptosis (Yang, Cancer Cell 2012; and Hagner et al. "CC-122, a pleiotropic pathway modifier, mimics an interferon response and has antitumor activity in DLBCL" Blood 2015, 126: 779-789). This effect has been shown to synergize with inhibition of NFkB signaling to further drive DLBCL cell death (Yang, Cancer Cell 2012).

In some instances, the combination of an IMiD with a small molecule IRAK4 kinase inhibitor shows little to no additive effect on viability of the MYD88 mutant ABC DLBCL cell lines, such as OCI-LY10. In some embodiments, the combination of an IRAK4 inhibitor with IMiD is less active than the IRAK degraders provided herein.

In certain embodiments, the combination of IRAK4 degradation with IKZF1 and IKZF3 degradation shows potent, single agent activity versus MYD88 mutant ABC DLBCL cell lines in vitro and OCI-LY10 xenograft in vivo. In some embodiments, IMiD-based IRAK4 degraders retain degradation of Ikaros (IKZF1) and other known IMiDs neosubstrates, while more strongly inducing an interferon response compared to pomalidomide alone. In some embodiments, IMiD-based IRAK4 degraders are potent at killing MYD88 mutant ABD-DLBCL cell lines in vitro, demonstrating increased activity versus that obtained from combining an IRAK4 inhibitor with IMiDs as single agents.

In certain embodiments, a provided IMiD-based IRAK4 degrader degrades IRAK4, Ikaros, and Aiolos in MYD88 mutant ABC DLBCL cell line xenografts in vivo, and strongly induces a signature of interferon-driven proteins exemplified by IFIT1 (interferon-inducible transcript 1) and IFIT3 (interferon-inducible transcript 3). In some embodiments, a provided IMiD-based IRAK4 degrader drives regression of tumor xenografts as a single agent.

In some embodiments, the provided compounds of present invention highlight a synergy obtained by combining IRAK4 degradation with IMiD induction of interferon response to drive single agent anti-tumor activity in MYD88 mutant DLBCL and possibly in other heme malignancies. In certain embodiments, a provided IMiD-based IRAK4 degrader degrade IRAK4, Ikaros, and Aiolos, acts synergistically. In some embodiments, a provided IMiD-based IRAK4 degrader degrades IRAK4, Ikaros, and Aiolos with increased activity in comparison to a provided IRAK4 degrader comprising the same IRAK4 binder and a non-IMiD-based E3 ligase and the same IMiD-based E3 ligase as a single agent.

In some embodiments the proliferative disease which can be treated according to the methods of this invention is an MyD88 driven disorder. In some embodiments, the MyD88 driven disorder which can be treated according to the methods of this invention is selected from ABC DLBCL, primary CNS lymphomas, primary extranodal lymphomas, Waldenstrom macroglobulinemia, Hodgkin's lymphoma, primary cutaneous T-cell lymphoma and chronic lymphocytic leukemia.

In some embodiments, the present invention provides a method of treating ABC DLBCL in a patient in need thereof, comprising administering an IRAK4 degrader (e.g., Compound A) of the present invention, or a pharmaceutically acceptable salt thereof.

In some embodiments, the present invention provides a method of treating primary CNS lymphomas in a patient in need thereof, comprising administering an IRAK4 degrader (e.g., Compound A) of the present invention, or a pharmaceutically acceptable salt thereof.

In some embodiments, the present invention provides a method of treating Hodgkin's lymphoma in a patient in need thereof, comprising administering an IRAK4 degrader (e.g., Compound A) of the present invention, or a pharmaceutically acceptable salt thereof.

In some embodiments, the present invention provides a method of treating primary cutaneous T-cell lymphoma in a patient in need thereof, comprising administering an IRAK4 degrader (e.g., Compound A) of the present invention, or a pharmaceutically acceptable salt thereof.

In some embodiments, the present invention provides a method of treating chronic lymphocytic leukemia in a patient in need thereof, comprising administering an IRAK4 degrader (e.g., Compound A) of the present invention, or a pharmaceutically acceptable salt thereof.

In some embodiments, the present invention provides a method of treating solid and liquid tumors in a patient in need thereof, comprising administering an IRAK4 degrader (e.g., Compound A) of the present invention, or a pharmaceutically acceptable salt thereof.

In some embodiments, the present invention provides a method of treating MYD88 mutant Waldenstrom macroglobulinemia in a patient in need thereof, comprising administering an IRAK4 degrader (e.g., Compound A) of the present invention, or a pharmaceutically acceptable salt thereof.

In some embodiments, the present invention provides a method of treating AML, or a subset thereof, in a patient in need thereof, comprising administering an IRAK4 degrader (e.g., Compound A) of the present invention, or a pharmaceutically acceptable salt thereof.

In some embodiments, the present invention provides a method of treating NSCLC in a patient in need thereof, comprising administering an IRAK4 degrader (e.g., Compound A) of the present invention, or a pharmaceutically acceptable salt thereof.

In some embodiments the proliferative disease which can be treated according to the methods of this invention is an IL-1 driven disorder. In some embodiments the IL-1 driven disorder is Smoldering of indolent multiple myeloma.

In some embodiments, the present invention provides a method for the treatment of adult patients with a MYD88-mutant B-cell lymphoma who have received one prior therapy.

In some embodiments, the present invention provides a method for the treatment of adult patients with a MYD88-mutant B-cell lymphoma who have received two prior therapies.

In some embodiments, the present invention provides a method for the treatment of adult patients with a MYD88-mutant B-cell lymphoma who have received at least one prior therapy.

In some embodiments, the present invention provides a method for the treatment of adult patients with a MYD88-mutant B-cell lymphoma who have received at least two prior therapies.

Combination Therapies

Depending upon the particular MYD88-mutant B-cell lymphoma to be treated, additional therapeutic agents, which are normally administered to treat that condition, may be administered in combination with compounds and compositions of this invention. As used herein, additional therapeutic agents that are normally administered to treat a particular MYD88-mutant B-cell lymphoma, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: anti-inflammatory agents such as corticosteroids, TNF blockers, IL-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketoconazole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours apart.

In one embodiment, the present invention provides a composition comprising a provided IRAK4 degrader or a pharmaceutically acceptable salt thereof and one or more additional therapeutic agents. The therapeutic agent may be administered together with a provided IRAK4 degrader or a pharmaceutically acceptable salt thereof, or may be administered prior to or following administration of a provided IRAK4 degrader or a pharmaceutically acceptable salt thereof. Suitable therapeutic agents are described in further detail below. In certain embodiments, a provided IRAK4 degrader or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided IRAK4 degrader or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating a solid tumor comprising administering to a patient in need thereof a provided IRAK4 degrader or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating diffuse large B-cell lymphoma (DLBCL) comprising administering to a patient in need thereof a provided IRAK4 degrader or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In some embodiments, the present invention provides a method of treating DLBCL comprising administering to a patient in need thereof a provided IRAK4 degrader or a pharmaceutically acceptable salt thereof and a CHOP (cyclophosphamide, Hydrodaunorubicin®, Oncovin®, and prednisone or prednisolone) or R-CHOP (rituximab, cyclophosphamide, Hydrodaunorubicin®, Oncovin®, and prednisone or prednisolone) chemotherapy regimen.

In some embodiments, the present invention provides a method of treating DLBCL comprising administering to a patient in need thereof a provided IRAK4 degrader or a pharmaceutically acceptable salt thereof and a rituximab or bendamustine chemotherapy regimen.

In some embodiments, the present invention provides a method of treating DLBCL comprising administering to a patient in need thereof a provided IRAK4 degrader or a pharmaceutically acceptable salt thereof and a BTK inhibitor (e.g., ibrutinib).

In some embodiments, the present invention provides a method of treating DLBCL comprising administering to a patient in need thereof a provided IRAK4 degrader or a pharmaceutically acceptable salt thereof and an anti-CD20 antibody (e.g., rituximab).

In some embodiments, the present invention provides a method of treating DLBCL comprising administering to a patient in need thereof a provided IRAK4 degrader or a pharmaceutically acceptable salt thereof and an anti-CD79B ADC (e.g., polatuzumab).

In some embodiments, the present invention provides a method of treating DLBCL comprising administering to a patient in need thereof a provided IRAK4 degrader or a pharmaceutically acceptable salt thereof and a BCL2 inhibitor (e.g., venetoclax).

In some embodiments, the present invention provides a method of treating DLBCL comprising administering to a patient in need thereof a provided IRAK4 degrader or a pharmaceutically acceptable salt thereof and lenalidomide or pomalidomide.

In some embodiments, the present invention provides a method of treating DLBCL comprising administering to a patient in need thereof a provided IRAK4 degrader or a pharmaceutically acceptable salt thereof and a PI3K inhibitor (e.g., umbralisib).

In some embodiments, the present invention provides a method of treating a T-cell disease or deficiency describing herein comprising administering to a patient in need thereof a provided IRAK4 degrader or a pharmaceutically acceptable salt thereof and a PI3K inhibitor (e.g., umbralisib).

In some embodiments, the present invention provides a method of treating DLBCL comprising administering to a patient in need thereof a provided IRAK4 degrader or a pharmaceutically acceptable salt thereof and a proteasome inhibitor (e.g., bortezomib).

In some embodiments, the present invention provides a method of treating DLBCL comprising administering to a patient in need thereof a provided IRAK4 degrader or a pharmaceutically acceptable salt thereof and chimeric antigen receptor T-cells.

In some embodiments, the present invention provides a method of treating a MYD88-mutant B-cell lymphoma comprising administering to a patient in need thereof a provided IRAK4 degrader (e.g., Compound A) or a pharmaceutically acceptable salt thereof and a BTK inhibitor (e.g., ibrutinib).

In some embodiments, the present invention provides a method of treating a MYD88-mutant B-cell lymphoma comprising administering to a patient in need thereof a provided IRAK4 degrader (e.g., Compound A) or or a pharmaceutically acceptable salt thereof and an anti-CD20 antibody (e.g., rituximab).

In some embodiments, the present invention provides a method of treating a MYD88-mutant B-cell lymphoma comprising administering to a patient in need thereof a provided IRAK4 degrader (e.g., Compound A) or or a pharmaceutically acceptable salt thereof and a BCL2 inhibitor (e.g., venetoclax).

In another embodiment, the present invention provides a method of treating multiple myeloma comprising administering to a patient in need thereof a provided IRAK4 degrader or a pharmaceutically acceptable salt thereof and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström macroglobulinemia comprising administering to a patient in need thereof a provided IRAK4 degrader or a pharmaceutically acceptable salt thereof and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFB). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFB "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF 1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZd$_6$244 from AstraZeneca, PD181461 from Pfizer and leucovorin.

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaeceuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547, 632 (Pfizer); foretinib (Exelexis, GlaxoSmithKline); quizartinib (Daiichi Sankyo) and motesanib (Amgen/Takeda).

In another embodiment, the present invention provides a method of treating or lessening the severity of a disease comprising administering to a patient in need thereof a provided IRAK4 degrader or a pharmaceutically acceptable salt thereof and a BTK inhibitor, wherein the disease is selected from B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenström macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis.

In another embodiment, the present invention provides a method of treating or lessening the severity of a disease comprising administering to a patient in need thereof a provided IRAK4 degrader or a pharmaceutically acceptable salt thereof and a PI3K inhibitor, wherein the disease is selected from lymphomas, (including, for example, non-Hodgkin's Lymphoma (NHL) and Hodgkin's lymphoma (also termed Hodgkin's or Hodgkin's disease)).

In some embodiments, one or more other therapeutic agent is a phosphatidylinositol 3 kinase (PI3K) inhibitor selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethyl-amino-17-demethoxy-geldanamycin, NSC707545), IPI-504, CNF 1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™) The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™ Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO 2008/118802, US 2010/0197686), navitoclax (and analogs thereof, see U.S. Pat. No. 7,390,799), NH-1 (Shenayng Pharmaceutical University), obatoclax (and analogs thereof, see WO 2004/106328, US 2005/0014802), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl) methyl]amino}-benzoic acid adamantyl ester; NSC 680410, adaphostin); l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

Compounds which target, decrease or inhibit the activity of a protein or lipid phosphatase are e.g. inhibitors of phosphatase 1, phosphatase 2A, or CDC25, such as okadaic acid or a derivative thereof.

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™),); carfilzomib (Kyprolis®, Amgen); and ixazomib (Ninlaro®, Takeda), and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251 , BAY 12-9566, TAA211 , MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuranosylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCRS, particularly CCR-5 antagonists such as Schering-Plough antagonists SC-351125, SCH- 55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided IRAK4 degrader is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a MYD88-mutant B-cell lymphoma.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD- L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin αlβ2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO 2011/070024, US 2011/0165156, WO 2011/0107553, US 2012/0329997, WO 2011/131407, US 2013/0005949, WO 2013/087699, US 2014/0336363, WO 2013/119716, WO 2013/132044, US 2014/0079706) or FPA-008 (WO 2011/140249, US 2011/0274683; WO 2013/169264; WO 2014/036357, US 2014/0079699).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO 2010/077634, US 2010/0203056), durvalumab (MEDI4736), BMS-936559 (WO 2007/005874, US 2009/0055944), and MSB0010718C (WO 2013/079174, US 2014/0341917).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO 2010/019570, US 2010/0150892, WO 2014/008218, US 2014/0093511), or IMP-731 or IMP-321 (WO 2008/132601, US 2010/0233183, WO 2009/044273, US 2011/0008331).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO 2006/105021, US 2007/0098719, WO 2009/009116, US 2009/0136494), or MK-4166 (WO 2011/028683, US 2012/0189639).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, New-Link Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO 2009/073620, US 2011/053941, WO 2009/132238, US 2011/136796, WO 2011/056652, US 2012/277217, WO 2012/142237, US 2014/066625).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO 2006/029879, U.S. Pat. No. 7,501,496).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO 2011/109400, US 2013/0149236).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TGO1 and TGO2 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8$^+$T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARS link to endogenous signaling pathways in the effector cell and generate activating signals similar to those initiated by the TCR complex.

For example, in some embodiments the CAR-T cell is one of those described in U.S. Pat. No. 8,906,682, the entirety of each of which is herein incorporated by reference, which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiment, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γ6, and memory CD8$^+$(αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-Hl; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

Exemplification

General Synthetic Methods

The following examples are intended to illustrate the invention and are not to be construed as being limitations thereon. Temperatures are given in degrees centigrade. If not mentioned otherwise, all evaporations were performed under reduced pressure, preferably between about 15 mm Hg and 100 mm Hg (=20-133 mbar). The structure of final products, intermediates and starting materials was confirmed by standard analytical methods, e.g., microanalysis and spectroscopic characteristics, e.g., MS, IR, NMR. Abbreviations used are those conventional in the art.

All starting materials, building blocks, reagents, acids, bases, solvents, and catalysts utilized to synthesis the compounds of the present invention were either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions were carried out under nitrogen or argon unless otherwise stated.

Proton NMR ($^1$ NMR) was conducted in deuterated solvent. In certain compounds disclosed herein, one or more $^1$H shifts overlap with residual proteo solvent signals; these signals have not been reported in the experimental provided hereinafter.

TABLE 2

| | Analytical instruments |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give MH$^+$] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml /min and mobile phase are used (A) 2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give MH$^+$] and equipped with Xbridge C18, 2.1×50 mm columns packed with 5 mm C18-coated silica or Kinetex EVO C18 2.1×30mm columns packed with 5 mm C18-coated silica, eluting with 0.05 vol % NH$_3$·H$_2$O in water (solvent A) and acetonitrile (solvent B).

HPLC Analytical Method: HPLC was carried out on X Bridge C18 150*4.6 mm, 5 micron. Column flow is 1.0 ml/min and mobile phase are used (A) 0.1% Ammonia in water and (B) 0.1% Ammonia in Acetonitrile.

Prep HPLC Analytical Method: The compound was purified on Shimadzu LC-20AP and UV detector. The column used was X-BRIDGE C18 (250*19)mm, 5 μ. Column flow was 16.0 ml/min. Mobile phase used was (A) 0.1% Formic Acid in Water and (B) Acetonitrile. Basic method used was (A) 5 mM ammonium bicarbonate and 0.1% NH$_3$ in Water and (B) Acetonitrile or (A) 0.1% Ammonium Hydroxide in Water and (B) Acetonitrile. The UV spectra were recorded at 20 2nm & 254 nm.

NMR Method: The 1H NMR spectra were recorded on a Bruker Ultra Shield Advance 400 MHz/5 mm Probe (BBFO). The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Intermediates 2-(2,6-Dioxopiperidin-3-yl)-4-fluoroisoindoline-1,3-dione (Intermediate R)

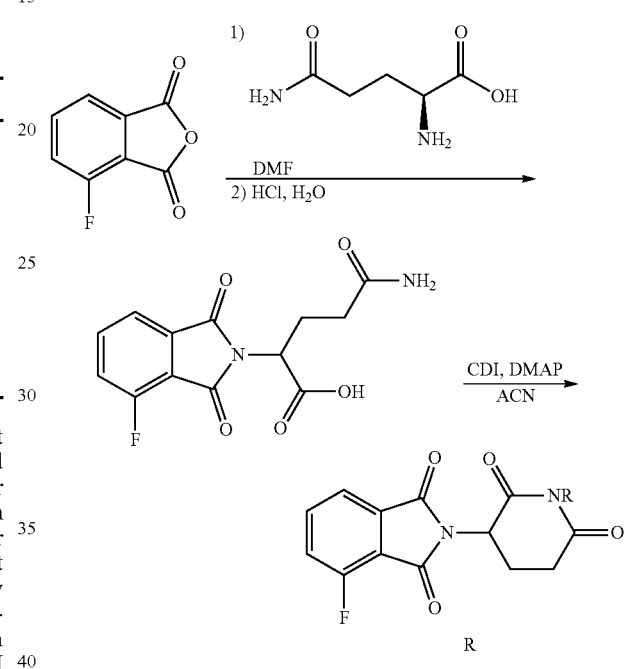

Step 1—5-amino-2-(4-fluoro-1,3-dioxoisoindolin-2-yl)-5-oxopentanoic acid

To a stirred solution of 4-fluoroisobenzofuran-1,3-dione (25 g, 150 mmol, CAS#652-39-1) in DMF (100 mL) was added L-glutamine (22 g, 150 mmol) at rt. The resulting reaction mixture was heated to at 90° C. and stirred for 2 h. The reaction mixture was then evaporated under reduced pressure, transferred into 4 N aqueous HCl solution and the resulting mixture was stirred for 36 h at rt. The solid precipitate was then filtered off, washed with cold water and dried under reduced pressure to give 5-amino-2-(4-fluoro-1,3-dioxoisoindolin-2-yl)-5-oxopentanoic acid as a white solid (28 g, 63%). LC-MS (ESI$^+$) m/z 295 (M+H)$^+$.

Step 2—2-(2,6-dioxopiperidin-3-yl)-4-fluoroisoindoline-1,3-dione

To a stirred solution of 5-amino-2-(4-fluoro-1,3-dioxoisoindolin-2-yl)-5-oxopentanoic acid (28 g, 95 mmol) in acetonitrile (200 mL) was added CDI (19 g, 110 mmol) and DMAP (0.14 g, 1.1 mmol) at rt. The resulting reaction mixture then heated to 90° C. and stirred for 5 h. The reaction mixture was then evaporated under reduced pressure. The crude product was purified using silica gel column chromatography (2% MeOH-DCM) to give 2-(2,6-dioxopiperidin-3-yl)-4-fluoroisoindoline-1,3-dione as a yellow solid (12 g, 46%). $^1$H NMR (400 MHz, DMSO) δppm 11.16 (s, 1H), 7.98-7.93 (m, 1H), 7.80-7.76 (m, 2H), 5.19-5.14 (m, 1H), 2.94-2.85 (m, 1H), 2.63-2.54 (m, 2H), 2.09-2.04 (m, 1H).

Tert-butyl 6-(2-aminoethyl)-2-azaspiro[3.3]heptane-2-carboxylate (Intermediate ATG)

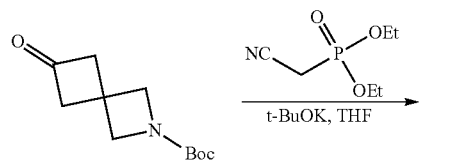

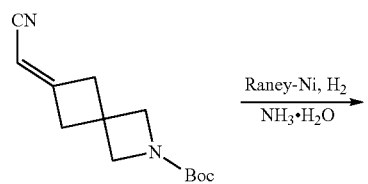

Step 1—Tert-butyl 6-(cyanomethylene)-2-azaspiro[3.3]heptane-2-carboxylate

To a solution of t-BuOK (3.98 g, 35.5 mmol,) in THF (35 mL) was added a solution of 2-diethoxyphosphorylacetonitrile (6.29 g, 35.5 mmol) in THF (70 mL) at 0° C. dropwise, and the reaction was stirred at 25° C. for 0.5 h. After, the mixture was cooled to 0° C. and a solution of tert-butyl 6-oxo-2-azaspiro[3.3]heptane-2-carboxylate (5.00 g, 23.7 mmol, CAS#1147557-97-8) in THF (35 mL) was added and the reaction was stirred at 25° C. for 16 hours. On completion, the reaction was quenched with water (10 mL) and the solvent was removed in vacuo to give a residue. The residue was purified by silica gel column chromatography (PE: EA from 5:1 to 1:1) to give the title compound (4.10 g, 66% yield) as a yellow oil. $^1$H NMR (400 MHz, DMSO-$d_6$) δ5.55 (t, J=2.4 Hz, 1H), 3.91 (d, J=2.0 Hz, 4H), 3.17-3.01 (m, 4H), 1.37 (s, 9H).

Step 2—Tert-butyl 6-(2-aminoethyl)-2-azaspiro[3.3]heptane-2-carboxylate

To a solution of tert-butyl 6-(cyanomethylene)-2-azaspiro [3.3]heptane-2-carboxylate (4.10 g, 17.5 mmol) in MeOH (80 mL) and NH$_3$·H$_2$O (8 mL) was added Raney-Ni (1.50 g, 17.5 mmol). The mixture was degassed and purged with H$_2$ gas 3 times and then was stirred at 25° C. under H$_2$ at 50 psi for 3 hours. On completion, the reaction was filtered through celite, the filtered cake was washed with MeOH (3×5 mL) and the filtrate was concentrated in vacuo to give the title compound (3.10 g, 66% yield) as yellow oil. $^1$H NMR (400 MHz, DMSO-$d_6$) δ3.82 (d, J=7.6 Hz, 4H), 2.47-2.00 (m, 5H), 1.79-1.67 (m, 2H), 1.46-1.38 (m, 2H), 1.36 (s, 9H).

4-[2-(2-Azaspiro[3.3]heptan-6-yl)ethylamino]-2-(2,6-dioxo-3-piperidyl)isoindoline-1,3-dione (Intermediate ATH)

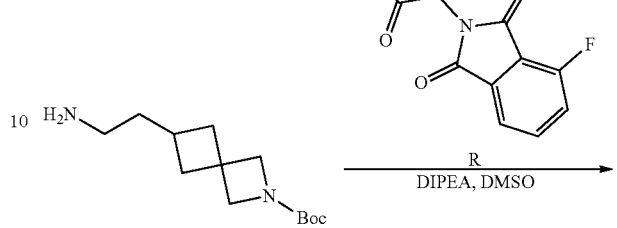

Step 1—Tert-butyl 6-[2-[[2-(2,6-dioxo-3-piperidyl)-1,3-dioxo-isoindolin-4-yl]amino]ethyl]-2-azaspiro[3.3]heptane-2-carboxylate To a solution of tert-butyl 6-(2-aminoethyl)-2-azaspiro [3.3]heptane-2-carboxylate (3.00 g, 12.5 mmol, Intermediate ATG) and 2-(2,6-dioxo-3-piperidyl)-4-fluoro-isoindoline-1,3-dione (3.79 g, 13.7 mmol, Intermediate R) in DMSO (30 mL) was added DIPEA (4.84 g, 37.5 mmol). The mixture was stirred at 130° C. for 1 hour. On completion, the reaction was diluted with EA (150 mL), washed with water (3×50 mL) and brine (100 mL), dried over Na$_2$SO$_4$, filtered and concentrated in vacuo to give a crude product which was purified by reversed phase (0.1% FA condition) to give the title compound (3.20 g, 46% yield) as a yellow solid. $^1$H NMR (400 MHz, DMSO-$d_6$) δ11.10 (s, 1H), 7.59 (dd, J=7.2, 8.4 Hz, 1H), 7.11-6.97 (m, 2H), 6.49 (t, J=5.6 Hz, 1H), 5.06 (dd, J=5.6, 12.8 Hz, 1H), 3.84 (s, 2H), 3.73 (s, 2H), 3.22 (q, J=6.4 Hz, 2H), 2.91-2.83 (m, 1H), 2.65-2.54 (m, 2H), 2.32-2.22 (m, 2H), 2.16 (t, J=7.6 Hz, 1H), 2.04 (d, J=2.4 Hz, 1H), 1.86-1.78 (m, 2H), 1.65 (q, J=7.2 Hz, 2H), 1.36 (s, 9H); LC-MS (ESI$^+$) m/z 497.3 (M+H)$^+$.

Step 2—4-[2-(2-Azaspiro[3.3]heptan-6-yl)ethylamino]-2-(2,6-dioxo-3-piperidyl)isoindoline-1,3-dione To a solution of tert-butyl 6-[2-[[2-(2,6-dioxo-3-piperidyl)-1,3-dioxo-isoindolin-4-yl]amino]ethyl]-2-azaspiro [3.3]heptane-2-carboxylate (0.30 g, 604 umol) in DCM (3 mL) was added TFA (2.31 g, 20.3 mmol). The mixture was stirred at 25° C. for 1 hour. On completion, the reaction was concentrated in vacuo to give the title compound (0.18 g, TFA, 58% yield) as a yellow solid.

(1R,4r)-4-((Benzyloxy)methyl)cyclohexanecarbonyl chloride (Intermediate BAU)

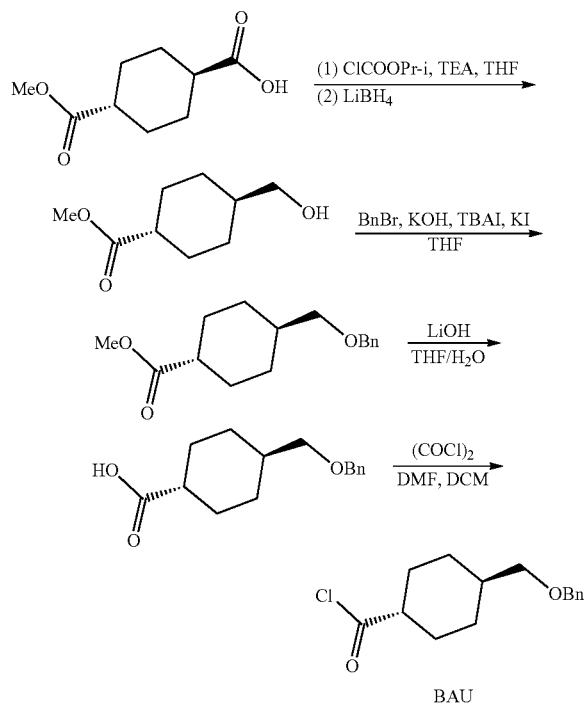

BAU

Step 1—(1R,4r)-Methyl 4-(hydroxymethyl)cyclohexanecarboxylate

To a solution of 4-methoxycarbonylcyclohexanecarboxylic acid (20.0 g, 107 mmol, CAS#15177-67-0) in the THF (200 mL) was added Et$_3$N (21.7 g, 215 mmol, 29.9 mL) and isopropyl carbonochloridate (19.7 g, 161 mmol, 22.4 mL) at 0° C. The mixture was stirred at 25° C. for 1 hour. Then the mixture was filtered and the LiBH$_4$ (11.7 g, 537 mmol) was added in portion at 0° C. The mixture was stirred at 25° C. for 4 hours. On completion, the mixture was quenched by water (500 mL) and extracted with EA (3×1000 mL). The organic layers were dried over Na$_2$SO$_4$, filtered and concentrated in vacuo. The residue was purified by column chromatography to give the title compound (9.70 g, 52% yield) as colorless oil. $^1$H NMR (400 MHz, CDCl$_3$) δ3.67 (s, 3H), 3.47 (d, J=6.0 Hz, 2H), 2.26 (tt, J=3.6, 12.4 Hz, 1H), 2.06-1.99 (m, 2H), 1.88 (dd, J=3.2, 13.6 Hz, 2H), 1.56-1.39 (m, 3H), 1.07-0.93 (m, 2H).

Step 2—(1R,4r)-Methyl 4-((benzyloxy)methyl)cyclohexanecarboxylate

To a solution of methyl 4-(hydroxymethyl)cyclohexanecarboxylate (9.70 g, 56.3 mmol) in the THF (100 mL) was added KOH (4.74 g, 84.5 mmol), TBAI (4.16 g, 11.3 mmol), KI (1.87 g, 11.3 mmol) and BnBr (14.5 g, 84.5 mmol, 10.0 mL). The mixture was stirred at 25° C. for 12 hours. On completion, the reaction mixture was filtered and concentrated in vacuo. The residue was purified by column chromatography to give the title compound (11.0 g, 74% yield) as colorless oil. $^1$H NMR (400 MHz, CDCl$_3$) δ7.39-7.27 (m, 5H), 4.50 (s, 2H), 3.67 (s, 3H), 3.29 (d, J=6.4 Hz, 2H), 2.25 (tt, J=3.6, 12.4 Hz, 1H), 2.04-1.98 (m, 2H), 1.91 (br dd, J=3.6, 13.6 Hz, 2H), 1.71-1.61 (m, 1H), 1.45-1.42 (m, 2H), 1.08-0.94 (m, 2H).

Step 3—(1R,4r)-4-((benzyloxy)methyl)cyclohexanecarboxylic acid

To a solution of methyl 4-(benzyloxymethyl)cyclohexanecarboxylate (11.0 g, 41.9 mmol) in the THF (100 mL), MeOH (20 mL) and H$_2$O (20 mL) was added LiOH (5.02 g, 210 mmol). The mixture was stirred at 25° C. for 12 hours. On completion, the reaction mixture was concentrated in vacuo. The residue was diluted with water (100 mL) and washed with PE (200 mL). The water phase was acidifed by HCl (aq, 1M) to pH=4. Then the mixture was extracted with DCM (3×200 mL). The organic layer was dried over Na$_2$SO$_4$, filtered and concentrated in vacuo to give the title compound (10.1 g, 97% yield) as colorless oil. $^1$H NMR (400 MHz, CDCl$_3$) δ7.41-7.26 (m, 5H), 4.50 (s, 2H), 3.30 (d, J=6.4 Hz, 2H), 2.28 (tt, J=3.6, 12.4 Hz, 1H), 2.05 (dd, J=2.8, 13.6 Hz, 2H), 1.92 (dd, J=2.8, 13.6 Hz, 2H), 1.65-1.62 (m, 1H), 1.46 (dq, J=3.6, 12.8 Hz, 2H), 1.11-0.95 (m, 2H).

Step 4—(1R,4r)-4-((Benzyloxy)methyl)cyclohexanecarbonyl chloride

To a solution of 4-(benzyloxymethyl)cyclohexanecarboxylic acid (10.0 g, 40.3 mmol) in the DCM (100 mL) was added DMF (294 mg, 4.03 mmol) and (COCl)$_2$ (7.67 g, 60.4 mmol, 5.29 mL) in portion at 0° C. The mixture was stirred at 0° C. for 2 hrs. On completion, the reaction mixture was concentrated in vacuo to give the title compound (10.7 g, 99% yield) as yellow oil.

Methyl 5-amino-2-bromo-4-iodo-benzoate (Intermediate BAV)

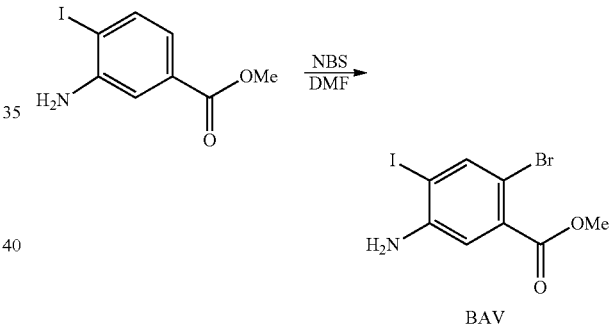

BAV

To a solution of methyl 3-amino-4-iodo-benzoate (5.00 g, 18.1 mmol, CAS#412947-54-7) in DMF (25 mL) was added NBS (3.28 g, 18.4 mmol). The mixture was stirred at 0° C. for 2 hours. On completion, the mixture was poured into 500 mL water and a solid was obtained. The mixture was filtered then the filtered cake was washed with water (3×50 mL) and dried in vacuo to give the title compound (6.00 g, 93% yield) as yellow solid. $^1$H NMR (400 MHz, DMSO-d$_6$) δ7.84 (s, 1H), 7.13 (s, 1H), 5.66 (br s, 2H), 3.81 (s, 3H).

Methyl 6-bromo-2-[4-(hydroxymethyl)cyclohexyl]-1,3-benzothiazole-5-carboxylate (Intermediate BAW)

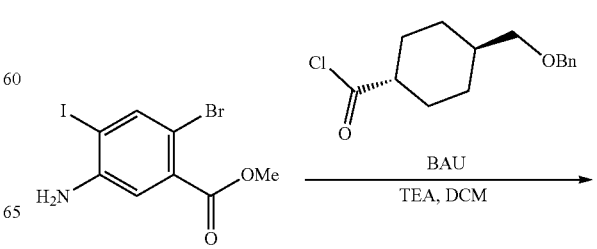

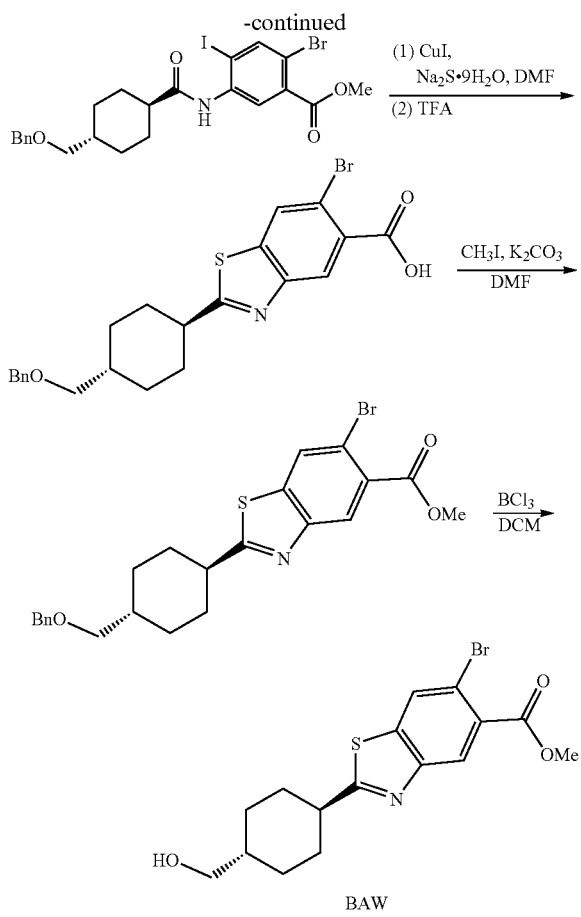

BAW

Step 1—Methyl 5-[[4-(benzyloxymethyl)cyclohexanecarbonyl]amino]-2-bromo-4-iodo-benzoate To a solution of methyl 5-amino-2-bromo-4-iodo-benzoate (707 mg, 1.9 mmol, Intermediate BAV) in DCM (10 mL) was added Et$_3$N (603 mg, 5.96 mmol). Then a mixture of 4-(benzyloxymethyl)cyclohexane carbonyl chloride (530 mg, 1.99 mmol, Intermediate BAU) in DCM (20 mL) was added to the reaction mixture. The mixture was stirred at 0° C. for 2 hours. On completion, the mixture was concentrated in vacuo. The residue was diluted with water (50 mL) and extracted with EA (3×100 mL). The combined organic layers were washed with brine (50 mL), dried over Na$_2$SO$_4$, filtered and concentrated of most solvent. Then the solid was precipitated out, then filtered, the cake was dried in vacuo to give the title compound (660 mg, 56% yield) as white solid. $^1$H NMR (400 MHz, CDCl$_3$) 67 8.76 (d, J=1.6 Hz, 1H), 8.09 (d, J=1.6 Hz, 1H), 7.52 (s, 1H), 7.41-7.27 (m, 5H), 4.52 (d, J=1.6 Hz, 2H), 3.92 (d, J=1.6 Hz, 3H), 3.34 (dd, J=1.6, 6.0 Hz, 2H), 2.35-2.24 (m, 1H), 2.12 (d, J=13.2 Hz, 2H), 2.00 (d, J=13.2 Hz, 2H), 1.77-1.58 (m, 3H), 1.19-1.05 (m, 2H).

Step 2—2-[4-(Benzyloxymethyl)cyclohexyl]-6-bromo-1,3-benzothiazole-5-carboxylic acid To a solution of methyl 5-[[4-(benzyloxymethyl)cyclohexanecarbonyl]amino]-2-bromo-4-iodo-benzoate (5.60 g, 9.55 mmol) in DMF (50 mL) was added CuI (363 mg, 1.91 mmol) and Na$_2$S·9H$_2$O (13.7 g, 57.3 mmol). The mixture was stirred at 80° C. for 6 hours, and then cooled to rt. Then TFA (15.4 g, 135 mmol) was added to the mixture and the mixture was stirred at 25° C. for 6 hours. On completion, the residue was diluted with water (100 mL) and extracted with EA (3×100 mL). The combined organic layers were washed with brine (100 mL), dried over Na$_2$SO$_4$, filtered and concentrated in vacuo to give the title compound (4.00 g, 56% yield) as yellow oil. LC-MS (ESI+) m/z 462.1 (M+3)$^+$.

Step 3—Methyl 2-[4-(benzyloxymethyl)cyclohexyl]-6-bromo-1,3-benzothiazole-5-carboxylate To a solution of 2-[4-(benzyloxymethyl)cyclohexyl]-6-bromo-1,3-benzothiazole-5-carboxylic acid (4.00 g, 8.69 mmol) in DMF (20 mL) was added CH$_3$I (2.47 g, 17.3 mmol) and K$_2$CO$_3$ (2.40 g, 17.3 mmol). The mixture was stirred at 15° C. for 2 hours. On completion, the mixture was filtered and concentrated in vacuo. The residue was purified by flash silica gel chromatography (PE: EA 3:1) to give title compound (3.00 g, 72% yield) as white solid. $^1$H NMR (400 MHz, CDCl$_3$) δ8.31 (s, 1H), 8.05 (s, 1H), 7.31-7.21 (m, 5H), 4.44 (s, 2H), 3.88 (s, 3H), 3.27 (d, J=6.0 Hz, 2H), 2.97 (t, J=12.0 Hz, 1H), 2.87 (s, 5H), 2.80 (s, 5H), 2.19 (d, J=12.4 Hz, 2H), 1.95 (d, J=13.6 Hz, 2H), 1.73-1.65 (m, 1H), 1.58 (q, J=12.8 Hz, 2H), 1.20-1.07 (m, 2H).

Step 4—Methyl 6-bromo-2-[4-(hydroxymethyl)cyclohexyl]-1,3-benzothiazole-5-carboxylate To a solution of methyl 2-[4-(benzyloxymethyl)cyclohexyl]-6-bromo-1,3-benzothiazole-5-carboxylate (2.00 g, 4.22 mmol) in DCM (40 mL) was added BCl$_3$ (9.88 g, 84.3 mmol). The mixture was stirred at 25° C. for 2 hours. On completion, to the mixture was added sat.NaHCO$_3$. aq (50 mL) then extracted with DCM (3×50 mL). The combined organic layers were washed with brine (100 mL), dried over Na$_2$SO$_4$, filtered and concentrated in vacuo to give the title compound (1.60 g, 90% yield) as white solid. $^1$NMR (400 MHz, CDCl$_3$) δ8.48 (s, 1H), 8.21-8.13 (m, 1H), 3.98 (s, 3H), 3.55 (d, J=6.0 Hz, 2H), 3.25-3.12 (m, 1H), 2.42-2.26 (m, 2H), 2.09-1.98 (m, 2H), 1.78-1.62 (m, 3H), 1.29-1.16 (m, 2H).

6-(Trifluoromethyl)pyridine-2-carboxamide (Intermediate ATI)

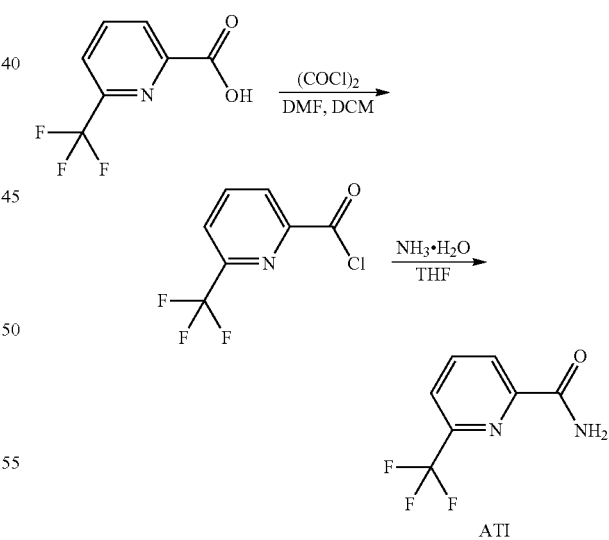

Step 1—6-(Trifluoromethyl)pyridine-2-carbonyl chloride

To a mixture of 6-(trifluoromethyl)pyridine-2-carboxylic acid (21.0 g, 109 mmol, CAS#131747-42-7) and DMF (401 mg, 5.49 mmol) in DCM (300 mL) was added (COCl)$_2$ (27.9 g, 219 mmol) at 0° C. The mixture was stirred at 25° C. for 1 hour. On completion, the reaction mixture was concentrated in vacuo to give the title compound (22 g, 95% yield) as light yellow oil.

Step 2—6-(Trifluoromethyl)pyridine-2-carboxamide

A solution of 6-(trifluoromethyl)pyridine-2-carbonyl chloride (21.5 g, 102 mmol) in THF (100 mL) was added NH$_3$·H$_2$O (143 g, 1.03 mol, 158 mL, 25% solution) at 0° C. The mixture was stirred at 25° C. for 1 hour. On completion, the reaction mixture was concentrated in vacuo to remove THF and then filtered to give the filter cake as title product (19 g, 90% yield) as light yellow solid. $^1$H NMR (400 MHz, DMSO-d$_6$) δ8.35-8.24 (m, 2H), 8.08 (dd, J=1.6, 6.8 Hz, 1H), 8.05-7.78 (m, 2H); LC-MS (ESI$^+$) m/z 191.0 (M+H)$^+$.

N-[2-2(4-formylcyclohexyl)-5-(1-hydroxy-1-methyl-ethyl)-1,3-benzothiazol-6-yl]-6-(trifluoromethyl) pyridine-2-carboxamide (Intermediate BAX)

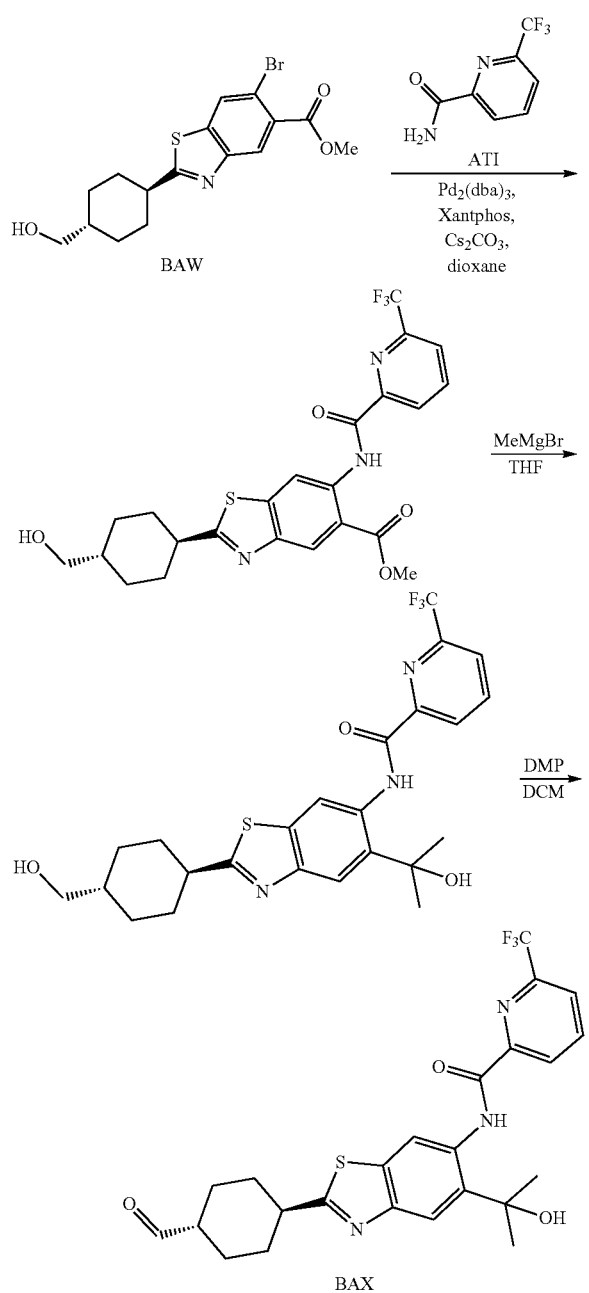

Step 1—Methyl 2-[4-(hydroxymethyl)cyclohexyl]-6-[[6-(trifluoromethyl)pyridine-2-carbonyl]amino]-1,3-benzothiazole-5-carboxylate To a solution of methyl 6-bromo-2-[4-(hydroxymethyl)cyclohexyl]-1,3-benzothiazole-5-carboxylate (300 mg, 780 umol, Intermediate BAW) and 6-(trifluoromethyl)pyridine-2-carboxamide (163 mg, 858 umol, Intermediate ATI) in dioxane (30 mL) was added Xantphos (90.3 mg, 156 umol), Cs$_2$CO$_3$ (763 mg, 2.34 mmol) and Pd$_2$(dba)$_3$ (71.4 mg, 78.1 umol) at 25° C. The mixture was stirred at 80° C. for 12 hrs under N$_2$. On completion, the mixture was filtered with celite and concentrated in vacuo. The residue was purified by column chromatography to give title compound (120 mg, 31% yield) as yellow solid. $^1$H NMR (400 MHz, DMSO-d$_6$) δ12.82 (s, 1H), 9.44 (s, 1H), 8.54 (s, 1H), 8.50-8.46 (m, 1H), 8.45-8.38 (m, 1H), 8.23 (d, J=7.8 Hz, 1H), 4.53-4.40 (m, 1H), 3.98 (s, 3H), 3.27 (t, J=5.6 Hz, 2H), 3.08 (s, 1H), 2.19 (d, J=13.0 Hz, 2H), 1.93-1.83 (m, 2H), 1.66-1.51 (m, 2H), 1.48-1.38 (m, 1H), 1.18-1.05 (m, 2H).

Step 2—N-[2-[4-(hydroxymethyl)cyclohexyl]-5-(1-hydroxy-1-methyl-ethyl)-1,3-benzothiazol-6-yl]-6-(trifluoromethyl)pyridine-2-carboxamide To a solution of methyl 2-[4-(hydroxymethyl)cyclohexyl]-6-[[6-(trifluoromethyl)pyridine-2-carbonyl]amino]-1,3-benzothiazole-5-carboxylate (120 mg, 243 umol) in THF (10 mL) was added MeMgBr (3 M, 405 uL). The mixture was stirred at 0° C. for 2 hours. The reaction mixture was quenched by addition sat. NH$_4$Cl (10 mL) at 0° C., and then diluted with water (50 mL) and extracted with EA (3×50 mL). The combined organic layers were washed with brine (100 mL), dried over Na$_2$SO$_4$, filtered and concentrated in vacuo to give a residue. The residue was purified by prep-HPLC (column: Phenomenex Synergi C18 150*25*10 um; mobile phase: [water (0.225% FA)-ACN]; B%: 44%-74%, 10 min) to give the title compound (80.0 mg, 60% yield) as white solid. NMR (400 MHz, DMSO-d$_6$) δ12.56 (s, 1H), 9.07 (s, 1H), 8.51-8.45 (m, 1H), 8.39 (t, J=8.0 Hz, 1H), 8.20 (d, J=7.6 Hz, 1H), 7.94-7.88 (m, 1H), 6.08 (s, 1H), 4.46 (t, J=5.2 Hz, 1H), 3.28 (t, J=5.6 Hz, 2H), 3.10-3.00 (m, 1H), 2.19 (d, J=11.2 Hz, 2H), 1.94-1.84 (m, 2H), 1.64 (s, 6H), 1.61-1.53 (m, 2H), 1.50-1.40 (m, 1H), 1.19-1.06 (m, 2H).

Step 3—N-[2-(4-formylcyclohexyl)-5-(1-hydroxy-1-methyl-ethyl)-1,3-benzothiazol-6-yl]-6-(trifluoromethyl) pyridine-2-carboxamide To a solution of N-[2-[4-(hydroxymethyl)cyclohexyl]-5-(1-hydroxy-1-methyl-ethyl)-1,3-benzothiazol-6-yl]-6-(trifluoromethyl) pyridine-2-carboxamide (50.0 mg, 101 umol) in DCM (10 mL) was added DMP (51.5 mg, 121 umol). The mixture was stirred at 25° C. for 2 hours. On completion, the mixture was added 10 mL sat. NaHCO$_3$ and 10 ~mL sat. Na$_2$S$_2$O$_3$, then extracted with DCM (3×50 mL). The combined organic layers were washed with brine (100 mL), dried over Na$_2$SO$_4$, filtered and concentrated in vacuo to give the title compound (60.0 mg, 90% yield) as yellow solid. LC-MS (EST$^+$) m/z 492.2 (M+1)$^+$.

Example 1

Synthesis of N-[2-[4-[[6-[2-[[2-(2,6-dioxo-3-piperidyl)-1,3-dioxo-isoindolin-4-yl]amino]ethyl]-2-azaspiro[3.3]heptan-2-yl]methyl]cyclohexyl]-5-(1-hydroxy-1-methyl-ethyl)-1,3-benzothiazol-6-yl]-6-(trifluoromethyl) pyridine-2-carboxamide (Compound A)

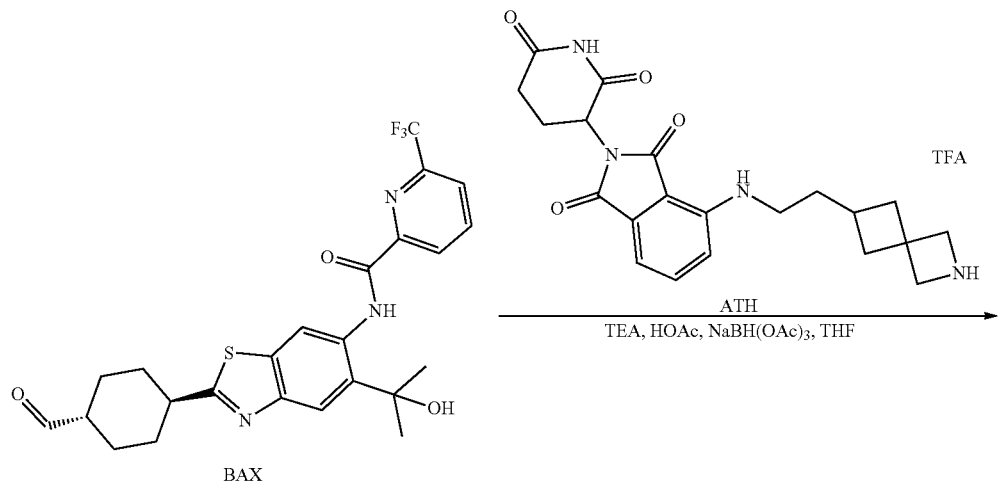

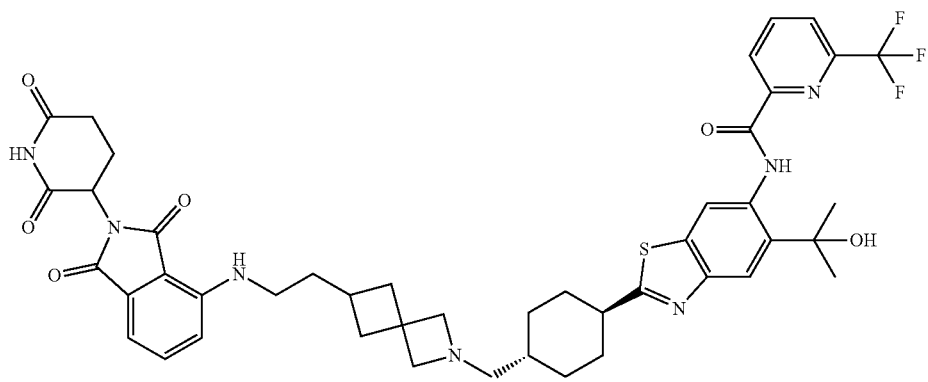

To a solution of 4-[2-(2-azaspiro[3.3]heptan-6-yl)ethylamino]-2-(2,6-dioxo-3-piperidyl) isoindoline-1,3-dione (75.8 mg, 148 umol, TFA salt, Intermediate ATH) in THF (2 mL) was added TEA (15.0 mg, 148 umol), then the mixture stirred at 25° C. for 10 min. Next, HOAc (8.92 mg, 148 umol) and N-[2-(4-formylcyclohexyl)-5-(1-hydroxy-1-methyl-ethyl)-1,3-benzothiazol-6-yl]-6-(trifluoromethyl) pyridine-2-carboxamide (73.0 mg, 148 umol, Intermediate BAX) were added to the mixture and the mixture was stirred at 25° C. for 20 minutes, then NaBH(OAc)$_3$ (62.9 mg, 297 umol) was added to the mixture at 0° C. The reaction mixture was stirred at 0-25° C. for 2 hours. On completion, the reaction mixture was quenched with H$_2$O (1 mL) and concentrated in vacuo. The residue was purified by prep-HPLC (column: Phenomenex Synergi C18 150*25*10 um; mobile phase: [water(0.225% FA)-ACN]; B %: 31%-58%, 9 min) to give the title compound (59.1 mg, 41% yield) as a yellow solid. $^1$H NMR (400 MHz, DMSO-d$_6$) δ12.54 (s, 1H), 11.09 (s, 1H), 9.06 (s, 1H), 8.49-8.44 (m, 1H), 8.38 (t, J=8.0 Hz, 1H), 8.19 (d, J=8.0 Hz, 1H), 7.88 (s, 1H), 7.58 (t, J=8.0 Hz, 1H), 7.10-6.99 (m, 2H), 6.47 (t, J=5.6 Hz, 1H), 6.07 (s, 1H), 5.05 (dd, J=5.6, 12.8 Hz, 1H), 3.54-3.47 (m, 2H), 3.25-3.18 (m, 4H), 3.06-2.99 (m, 1H), 2.93-2.83 (m, 1H), 2.63-2.56 (m, 1H), 2.54 (s, 3H), 2.30-2.21 (m, 2H), 2.30-2.21 (m, 3H), 2.06-1.99 (m, 1H), 1.88-1.77 (m, 4H), 1.68-1.61 (m, 8H), 1.58-1.49 (m, 2H), 1.45-1.36 (m, 1H), 1.15-1.02 (m, 2H); LC-MS (ESI+) m/z 872.2 (M+H)$^+$.

Example 2

Syntheses of N-[2-[4-[[6-[2-[[2-[(3R)-2,6-dioxo-3-piperidyl]-1,3-dioxo-isoindolin-4-yl]amino]ethyl]-2-azaspiro[3.3]heptan-2-yl]methyl]cyclohexyl]-5-(1-hydroxy-1-methyl-ethyl)-1,3-benzothiazol-6-yl]-6-(trifluoromethyl) pyridine-2-carboxamide and N-[2-[4-[[6-[2-[[2-[(3S)-2,6-dioxo-3-piperidyl]-1,3-dioxo-isoindolin-4-yl]amino]ethyl]-2-azaspiro[3.3]heptan-2-yl]methyl]cyclohexyl]-5-(1-hydroxy-1-methyl-ethyl)-1,3-benzothiazol-6-yl]-6-(trifluoromethyl) pyridine-2-carboxamide

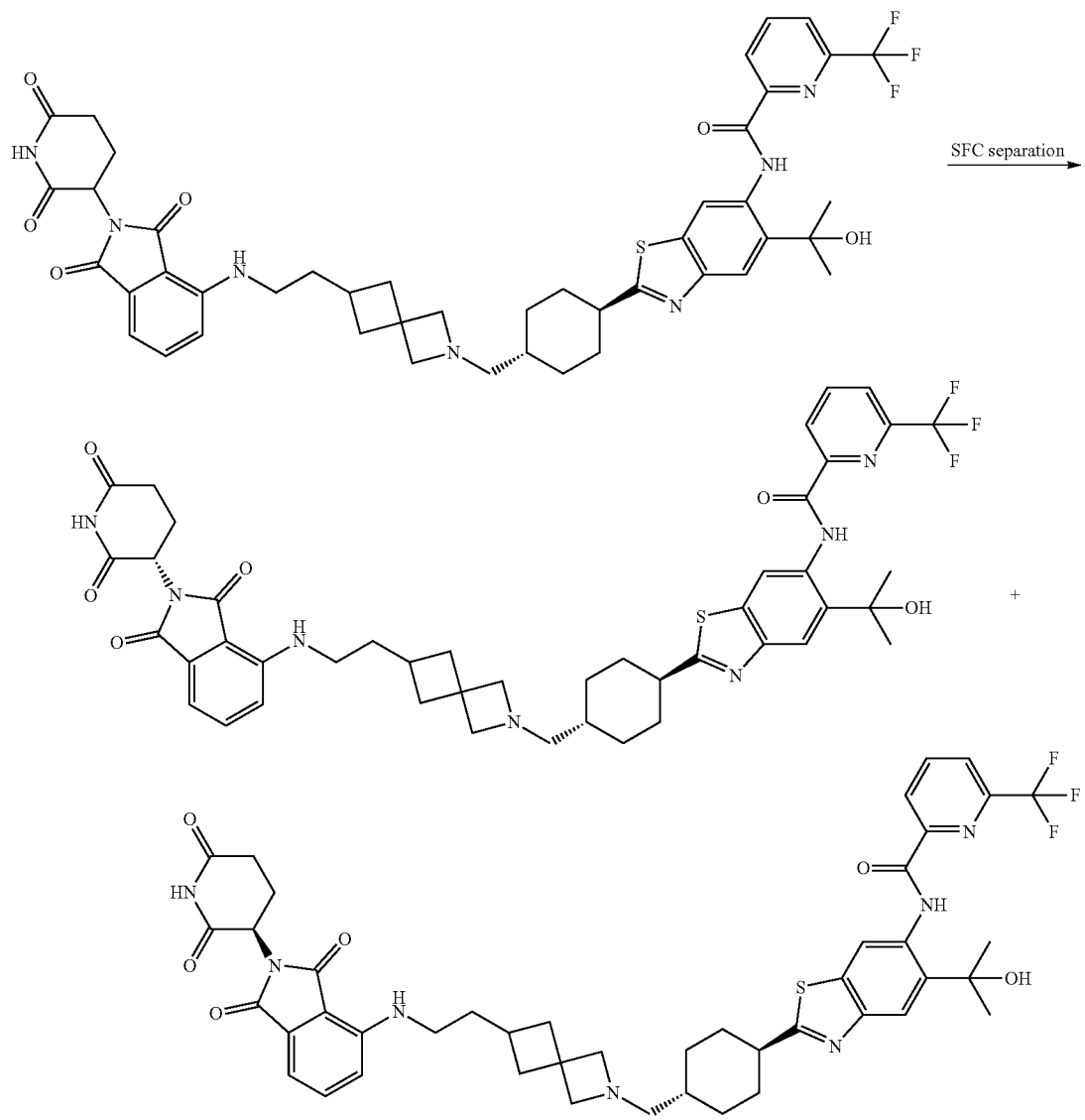

N-[2[4-[[6[2-[[2-(2,6-dioxo-3-piperidyl)-1,3-dioxo-isoindolin-4-yl]amino]ethyl]-2-azaspiro[3.3]heptan-2-yl]methyl]cyclohexyl]-5-(1-hydroxy-1-methyl-ethyl)-1,3-benzothiazol-6-yl]-6-(trifluoromethyl) pyridine-2-carboxamide (600 mg, 688 umol, Example I-3) was separated by SFC. The reactant was separated by SFC (column: DAICEL CHIRALPAK IA (250 mm*30 mm, 10 um); mobile phase: [0.1% NH$_3$H$_2$OIPA]; B %: 50%-50% 9.5 min; 200 min) to give the impure peak 1 and peak 2. The impure peak 1 and peak 2 was purified by reverse phase (0.1% FA) to give N-[2-[4-[[6-[2-[[2-[(3R)-2,6-dioxo-3-piperidyl]-1,3-dioxo-isoindolin-4-yl]amino]ethyl]-2-azaspiro[33]heptan-2-yl]methyl]cyclohexyl]-5-(1-hydroxy-1-methyl-ethyl)-1,3-benzothiazol-6-yl]-6-(trifluoromethyl) pyridine-2-carboxamide (204 mg, 64% yield, 99% purity, FA salt) as yellow solid: $^1$H NMR (400 MHz, DMSO-d$_6$) δ12.54 (s, 1H), 11.09 (s, 1H), 9.06 (s, 1H), 8.49-8.44 (m, 1H), 8.38 (t, J=8.0 Hz, 1H), 8.18 (d, J=8.0 Hz, 1H), 7.88 (s, 1H), 7.62-7.54 (m, 1H), 7.06 (d, J=8.4 Hz, 1H), 7.02 (d, J=7.2 Hz, 1H), 6.47 (t, J=5.6 Hz, 1H), 6.22-5.96 (m, 1H), 5.08-5.02 (m, 1H), 3.25 (s, 2H), 3.21 (d, J=6.0 Hz, 2H), 3.15 (s, 2H), 3.05-2.98 (m, 1H), 2.94-2.82 (m, 1H), 2.63-2.51 (m, 3H), 2.34-2.29 (m, 2H), 2.24-2.11 (m, 5H), 2.07-1.98 (m, 1H), 1.89-1.80 (m, 2H), 1.80-1.72 (m, 2H), 1.65 (s, 1H), 1.63 (s, 6H), 1.58-1.47 (m, 2H), 1.40-1.27 (m, 1H), 1.13-0.98 (m, 2H); LC-MS (ESI$^+$) m/z 872.6 (M+H)$^+$; and N-[2-[4-[[6-[2-[[2-[(3S)-2,6-dioxo-3-piperidyl]-1,3-dioxo-isoindolin-4-yl]amino]ethyl]-2- azaspiro [3.3]heptan-2-yl]methyl]cyclohexyl]-5-(1-hydroxy-1-methyl-ethyl)-1,3-benzothiazol-6-yl]-6-(trifluoromethyl) pyridine-2-carboxamide (233 mg, 73% yield, 99% purity, FA salt) as yellow solid. $^1$H NMR (400 MHz, DMSO-d$_6$) δ612.54 (s, 1H), 11.20-10.94 (m, 1H), 9.06 (s, 1H), 8.50-8.44 (m, 1H), 8.38 (t, J=7.6 Hz, 1H), 8.18 (d, J=8.4 Hz, 1H), 7.88 (s, 1H), 7.63-7.55 (m, 1H), 7.06 (d, J=8.8 Hz, 1H), 7.02 (d, J=7.2 Hz, 1H), 6.47 (t, J=6.0 Hz, 1H), 6.16-5.99 (m, 1H), 5.09-5.01 (m, 1H), 3.27 (s, 2H), 3.21 (d, J=6.8 Hz, 2H), 3.17 (s, 2H), 3.05-2.98 (m, 1H), 2.94-2.83 (m, 1H), 2.64-2.51 (m, 3H), 2.32 (d, J=6.4 Hz, 2H), 2.25-2.10 (m, 5H), 2.06-1.98 (m, 1H), 1.84 (d, J=11.6 Hz, 2H), 1.80-1.73 (m, 2H), 1.68-1.64 (m, 1H), 1.63 (s, 6H), 1.58-1.46 (m, 2H), 1.43-1.28 (m, 1H), 1.13-1.00 (m, 2H); LC-MS (ESI$^+$) m/z 872.6 (M+H)$^+$. The absolute configuration of the stereoisomers was assigned arbitrarily.

Example 3.

IRAK4 MSD Degradation in OCI-Ly10

Degradation of IRAK4 in OCI-Ly10 was quantitatively measured using Meso Scale Discovery technology. OCI-Ly10 cells were seeded in 96-well plates (Corning 3799) with a density of 300,000 cells per well in 100 μL fresh media. Compounds were then added to the assay plates with a final top concentration of 1 to 10 μM in a 1:3 dilution series with total of 8 doses. The assay plates were then incubated for 4 to 24 hours at 37° C. under 5% CO$_2$. The assay plates were then centrifuged for 5 minutes and the cell pellets were treated with 100 μL/well RIPA lysis buffer (Boston Bio-Products BP-115D) with proteinase inhibitors. To prepare MSD assay plates (Meso Scale Discovery Catalog number L15XA-3), the plates were coated with 2 μg/mL capture antibody (mouse Anti-IRAK4 antibody [2H9], ab119942) in PBS, at 40 μL/well. The plates were then incubated overnight at 4° C., washed 3 times with 150 μL/well TBST buffer (Cell Signaling Technology, Catalog number 9997S) and blocked with 150 μL/well blocking buffer (Meso Scale Discovery Catalog number R93BA-4). Cell lysates were then added to MSD assay plates and the plates were incubated at room temperature for 1 hour. The plates were then washed 3 times with 150 μL/well TBST buffer and 254/well primary detection antibody (rabbit Anti-IRAK4 antibody [Y279], from Abcam. Catalog number ab32511, 1 μg/mL). The assay plates were then incubated at room temperature for 1 hour, washed 3 times with 150 μL/well TBST buffer and 25 μL/well secondary detection antibody, SULFO-TAG anti-rabbit antibody were added (anti rabbit antibody from Meso Scale Discovery, Catalog number R32AB-1, 1 μg/mL). The assay plates were then incubated at room temperature for 1 hour, washed 3 times with 150 μL/well TBST buffer, and 150 μL/well MSD reading buffer (Meso Scale Discovery catalog number R92TC-2) was added. The plates were then analyzed by a MSD reader (Meso Scale Discovery, Model Quick Plex SQ 120). The data was then analyzed by software Prism 7.0 from GraphPad and the dose-depended IRAK4 degradation were fit using a three-parameter logistic equation to calculate DC$_{50}$.

IRAK4 MSD degradation results in OCI-LY10 cells for compounds of the invention are presented in Table 5. The letter codes for IRAK4 DC$_{50}$ include: A (<0.05 μM); B (0.05-0.1 μM); C (0.1-0.5 μM); D (0.5-1.0 μM); and E (>1.0 μM).

TABLE 5

IRAK4 MSD Degradation in OCI-Ly10 Results

| Compound | IRAK4 degradation in OCI-Ly10 at 4 hrs: DC$_{50}$ (μM) | IRAK4 degradation in OCI-Ly10 at 24 hrs: DC$_{50}$ (μM) |
|---|---|---|
| A | B | A |
| (R)-A | — | A |
| (S)-A | — | A |

Example 4

Cell viability Assay with OCI-Ly10 and SUDHL-2

Compound-mediated viability effect on OCI-Ly10 or SUDHL-2 was quantitatively determined using the CellTiter-Glo® Luminescent Cell Viability Assay kit from Promega (Catalog number G7570) following manufacturer's recommended procedures. Briefly, OCI-Ly10 or SUDHL-2 cells were seeded into 384 well plates (Grenier Bio-One, Catalog number 781080) with a density of 10,000 cells per well. Compounds were then added to the assay plate with final top concentration of 10 μM and 1:3 dilution series with total of 9 doses. The final DMSO concentration was normalized to 0.2%. The assay plates were incubated at 37° C. for 4 days under 5% CO$_2$. Then the assay plate was equilibrated at room temperature for 10 minutes. To determine cell viability, 30 μL CellTiter Glo reagent was added to each well and the assay plate was centrifuged at 1000 rpm for 30 second, incubated at room temperature for 10 min, and analyzed by detecting the luminescence using a multimode plate reader (EnVision 2105, PerkinElmer). The data was then analyzed by software Prism 7.0 from GraphPad and the dose response curves were fit using a three-parameter logistic equation to calculate IC$_{50}$.

CTG Cell Viability Assay—OCI-Ly10 and SUDHL-2 results for compounds of the invention are presented in Table 6. The letter codes for IRAK4 IC$_{50}$ include: A (<0.05 μM); B (0.05-0.1 μM); C (0.1-0.5 μM); D (0.5-1.0 μM); and E (>1.0 μM).

TABLE 6

CTG Cell Viability Assay Results

| Compound | CTG Cell Viability Assay - OCI-Ly10: IC$_{50}$ (μM) | CTG Cell Viability Assay - SUDHL-2: IC$_{50}$ (μM) |
|---|---|---|
| A | A | — |
| (R)-A | A | — |
| (S)-A | A | — |

Example 5

Quantification of Ikaros and Aiolos Degradation

Degradation of Ikaros (protein product of gene IKZF1) and Aiolos (protein product of gene IKZF3) were determined by quantitative immunoblotting as follows. OCI-Ly10 cells, 2×10$^6$ cells/well, were treated with listed concentrations of IRAK4 degraders or control compounds in 6 well plates for 6 h. Cells were collected, washed with cold PBS, lysed in RIPA buffer (Boston BioProducts BP-115D) with protease/phosphatase inhibitor cocktail (Roche 05892791001/Roche 04906837001) and centrifuged at 13000 RPM for 20 min to precipitate insoluble material. The supernatant fraction was diluted in SDS-PAGE loading buffer (Beyotime Bio P0015) and 20 μL of each sample was resolved on 4-12% Bis-Tris SDS-PAGE gels (Novex, WG1402BOX). Resolved samples were transferred to nitrocellulose membranes by wet electro-transfer method at 250 mV for 1.5 h. The membrane was blocked with LICOR blocking buffer (LI-COR, 927-50000) for 1 hour, washed three times with TBST (CST#99975) for 5 minutes each and incubated with primary antibody prepared in block buffer with 0.1% Tween-20 (Solarbio, P8220) at 4° C. overnight. Ikaros antibody was rabbit monoclonal D6N9Y (CST#14859), at 1:1000 dilution. Aiolos antibody was rabbit monoclonal D1C1E (CST#15103), at 1:1000 dilution. Signal was normalized to mouse anti-beta-Actin monoclonal 8H10D10 (CST#3700) used at 1:10,000 dilution. After incubation in primary antibodies, membranes were washed three times with TBST, 5 minutes each, incubated with fluorescently labeled secondary antibodies anti-rabbit IgG (Licor,926-32211) at 1:5000 dilution; anti-mouse IgG (LI-COR, 926-68070) at 1:5000 dilution, for 1 hour at RT. After incubation in secondary, membranes were washed three times with TBST, 5 minutes each and read on LICOR Odyssey imager. Data was reported as signal for Ikaros or Aiolos relative to signal for actin, and normalized to DMSO-treated control.

Ikaros and Aiolos degradation assay results in OCI-Ly10 cells for compounds of the invention are presented in Table 7. The letter codes for Ikaros and Aiolos $DC_{50}$ include: A (<0.05 µM); B (0.05-0.1 µM); C (0.1-0.5 µM); D (0.5-1.0 µM); and E (>1.0 µM).

Table 7. Ikaros and Aiolos Degradation Assay Results

TABLE 7

| Ikaros ans Aiolos Degradation Assay Results | | |
|---|---|---|
| Compound # | Ikaros Degradation in OCI-Ly10: $DC_{50}$ (µM) | Aiolos Degradation in OCI-Ly10: $DC_{50}$ (µM) |
| A | A | A |

Figure 8:
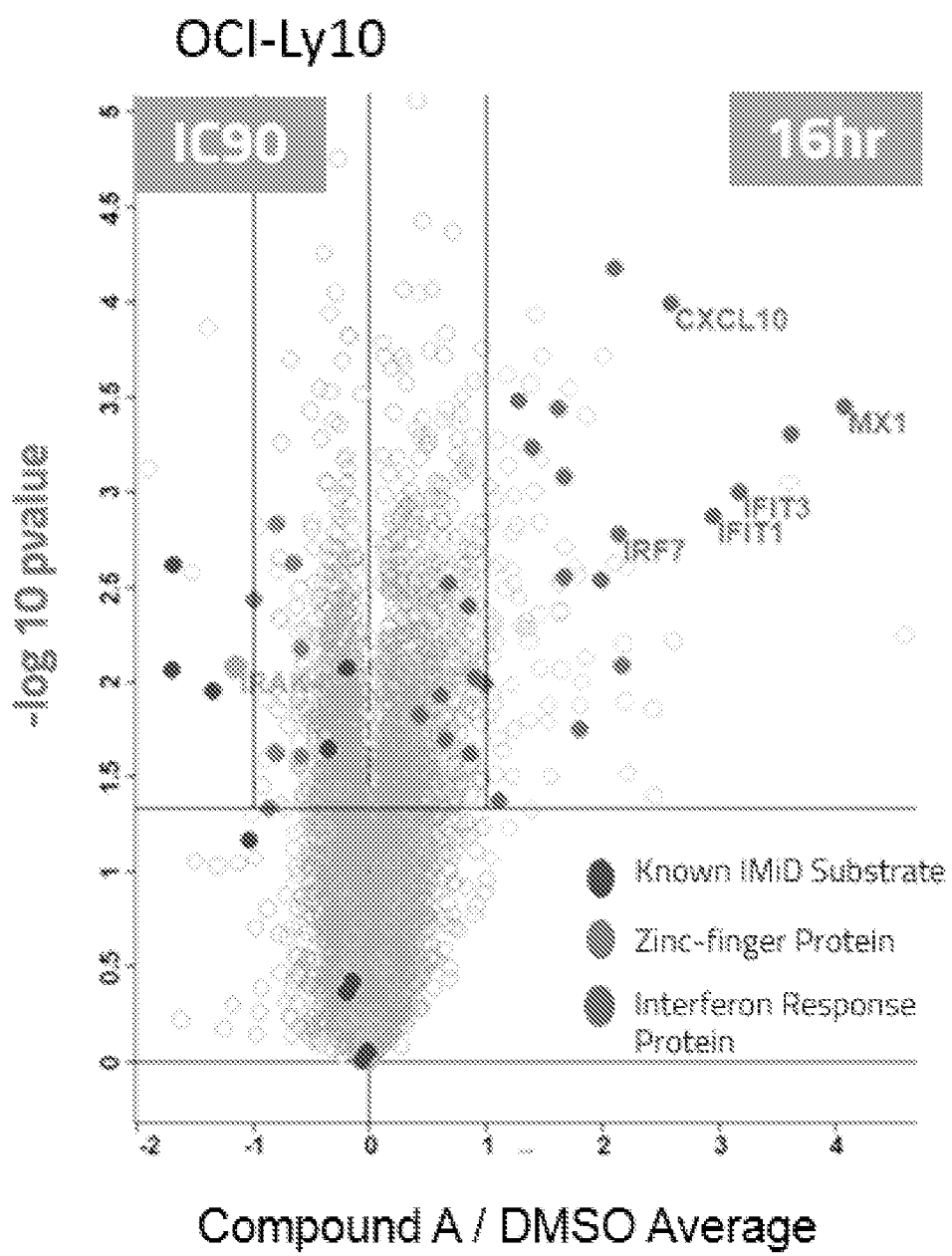
FIG. 8 depicts deep proteomics scatterplots showing degradation of IRAK4 and IMiD substrates in OCI-Ly10 using Compound A.

FIG. 8 depicts deep proteomics scatterplots showing degradation of IRAK4 and IMiD substrates in OCI-Ly10 using Compound A. Type 1 IFN signaling was activated in OCI-Ly10 MYD88$^{MT}$ DLBCL. The degradation time course shows hierarchical substrate degradation and rapid degradation of IMiD substrates, with >80% degradation of IRAK4 between 16-24 h post treatment.

Example 6

Xenograph Tumor Studies

Cell Culture: The OCI-LY10 tumor cells were maintained as suspension in RPMI1640 medium supplemented with 10% fetal bovine serum, 100 U/mL penicillin and 100 µg/mL streptomycin at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

Animals: C.B. 17 SCID, female, 6-8 weeks, weighing approximately 16-18 g were used. Animals were housed and maintained according to IACUC protocols.

Tumor Inoculation: Each mouse was inoculated subcutaneously at the right flank with OCI-LY10 tumor cells (10×10$^6$) in 0.2 mL of PBS with matrigel for tumor development. The treatments were started when the tumor sizes reached approximately 150-450 mm$^3$ for the studies.

Assignment to Groups: Before commencement of treatment, all animals were weighed and the tumor volumes were measured. Since the tumor volume can affect the compound PK/PD, mice are assigned into groups using an Excel-based randomization procedure performing stratified randomization based upon their tumor volumes.

Observation: After tumor inoculation, the animals were checked daily for morbidity and mortality. During routine monitoring, the animals were checked for any effects of tumor growth and treatments on behavior such as mobility, food and water consumption, body weight gain/loss, eye/hair matting and any other abnormalities. Mortality and observed clinical signs were recorded for individual animals in detail.

Data Collection: Tumor volumes were measured in two dimensions using a caliper, and the volumes were expressed in mm$^3$ using the formula: "V=(L×W×W)/2, where V is tumor volume, L is tumor length (the longest tumor dimension) and W is tumor width (the longest tumor dimension perpendicular to L).

At termination: At pre-determined time points based on study design, animals were humanely sacrificed by $CO_2$. Blood was obtained by cardiac puncture for isolation of plasma, any residual tumor was removed and divided in 2 portions, 1 (minimal) for terminal compound exposure and 1 to determine IRAK4 and actin. Compound was determined in tumor and plasma using LC/MS with calibrated standards.

Interleukin-1 receptor-associated kinase 4 (IRAK4) was quantified in human OCI-LY10 xenograft tumors, together with mouse splenocytes and peripheral blood mononuclear cells (PBMCs), by ultra-performance liquid chromatography-tandem mass spectrometry (UPLC-MS/MS). The concentrations of IRAK4 were normalized by the concentrations of actin in the respective samples. The tumors, splenocytes and PBMCs were lysed in tissue protein extraction reagent (T-PER, ThermoFisher). The samples were centrifuged at 10,000 rpm for 10 minutes. The supernatant (cell lysate) was transferred to another tube. The cell lysates were denatured, reduced, and alkylated with iodoacetamide. The alkylated samples were treated with trypsin to generate the IRAK4 peptide LAVAIK and the actin peptide GYSFTTTAER. These peptides are unique and specific to IRAK4 and actin, respectively, in human, rat and mouse cells and tissues due to sequence conservation between these species.

Signature peptide concentrations were quantitated using a sensitive and specific targeted LC-MS/MS method. Corresponding mass-shifted, stable isotope-labeled peptides (LAV(d8)AIK and GYSF(d8)TTTAE(d6)R) were used as internal standards (ISs). Calibration standards and were prepared fresh on the day of analysis by diluting synthetic LAVAIK and GYSF(d8)TTTAER peptides into 0.1% formic acid in 90/10 water acetonitrile (v/v). The standards and study samples) were aliquoted into a 96-well plate and mixed with IS spiking solution. The sample plate was covered with heating foil.

Signature peptide levels (LAVAIK, GYSFTTTAER) were quantified by UPLC-MS/MS. Injections were made using a Shimadzu ultra performance liquid chromatograph (UPLC) platform. Mobile phase A was 0.1% formic acid in water. Mobile phase B was 0.1% formic acid in 90:10 acetonitrile/water (v/v). A SCIEX TripleTOF 6600 LC-MS/MS system was used for the detection and quantitation of analytes. The intensities of the analytes and ISs were determined by integration of extracted ion peak areas using Analyst and MultiQuant 3.0 software. Calibration curves were prepared by plotting the analyte to IS peak area ratio vs. concentration. The model for the calibration curves was linear with $1/x^2$ weighting. The working range of the assay was 0.02-50 ng/mL for LAVAIK and 1-2500 ng/mL for GYSFTTTAER in digested cell lysate. Measured peptide levels were corrected for sample work up and converted to actual protein concentrations in ng/mg total protein of cell lysate. The concentrations of IRAK4 were normalized across samples by actin concentration.

Figure 2:
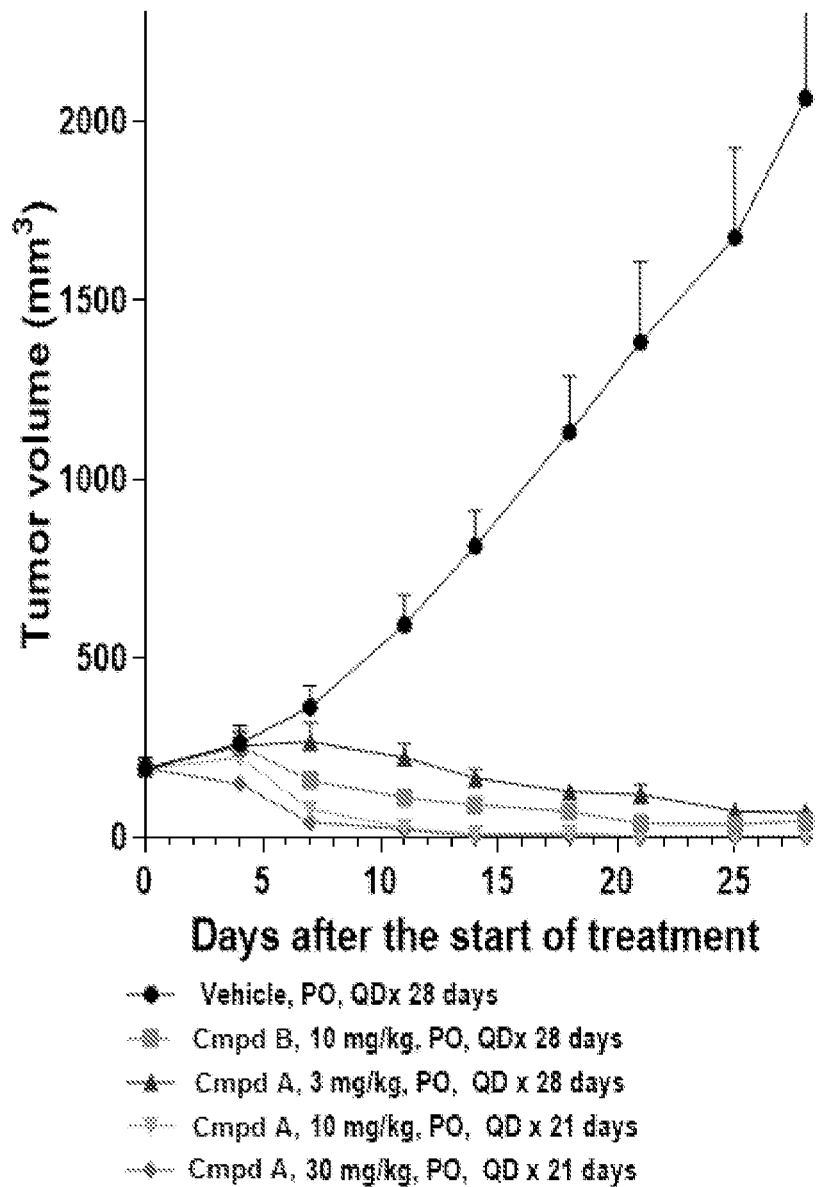
FIG. 2 shows that Compound A leads to more potent regressions than Compound B in OCI-Ly10 tumor xenographs. Compound A shows regressions at 3 mpk×21 d in OCI-Ly10 with higher doses (≥10 mpk) showing more rapid and complete regressions.

FIG. 2 shows that Compound A leads to potent regressions in OCI-Ly10 tumor xenographs. Compound A shows regressions at 3 mpk×21 d in OCI-Ly10 with higher doses (>10 mpk) showing more rapid and complete regressions. Target exposure for efficacy in OCI-Ly10 is steady state $C_{24h}$ of 10-80 nM based on either a 3 mpk or 10 mpk dose. Rapid regressions are associated with strong degradation of both IRAK4 and IMiD substrates. Table 8 and Table 9 show obtained PK and PD parameters.

TABLE 8

Compound A PK/Tumor PD Parameters After 5d Dosing

| Dose (mpk) | Plasma $C_{24h}$ (uM) | Spleen $C_{24h}$ (uM) | Tumor $C_{24h}$ (uM) | IRAK4 (% Deg) | Aiolos (% Deg) | TGI (28D) | |
|---|---|---|---|---|---|---|---|
| 3 | 0.01 | 0.5 | 0.43 | 16 | 49 | 91% | 4PR, 1SD |
| 10 | 0.08 | 4.1 | 4.2 | 75 | 91 | 99.9% | 5CR |
| 30 | 0.64 | 59.0 | 64 | 83 | 97 | 99.9% | 5CR |

TGI (tumor growth inhibition)=(1−T/C)100; PR (partial response)≥50% tumor shrinkage; CR (complete response) >95% tumor shrinkage from starting volume

TABLE 9

Compound A 10 mpk PO PK Parameters

| PK parameters | Unit | PO |
|---|---|---|
| $T_{1/2}$ | h | 9.35 |
| $T_{max}$ | h | 8 |
| $C_{max}$ | μM | 0.180 |
| $C_{24h}$ | μM | 0.055 |
| $AUC_{last}$ | μM * h | 2.83 |
| F | % | 19.0 |

Figure 3:
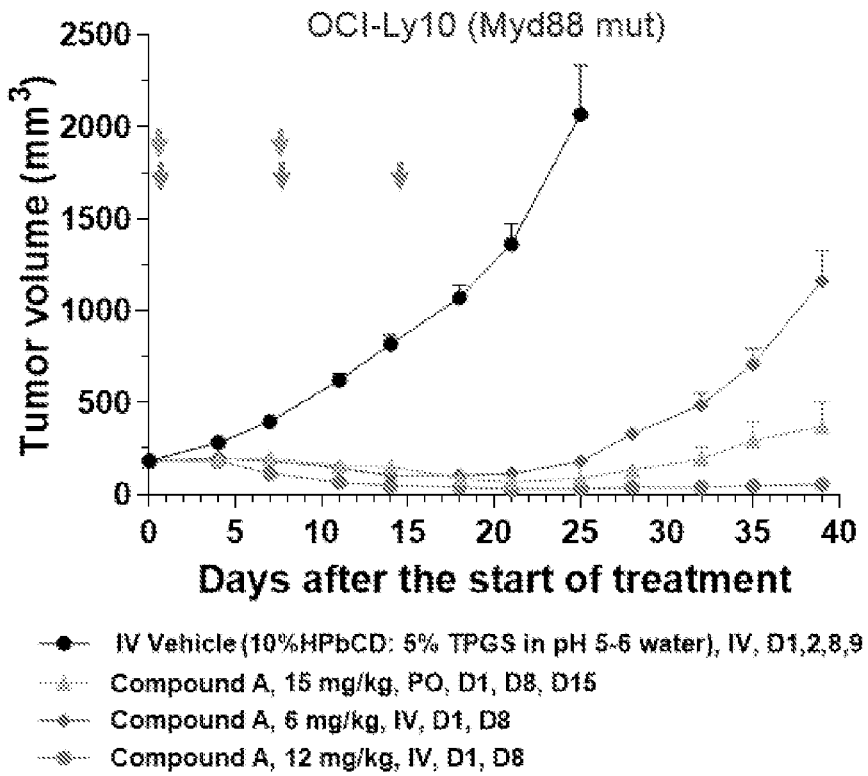
FIG. 3 shows minimum efficacious doses for QW and BIW schedules of Compound A in OCI-Ly10 tumor xenographs.
Figure 3:
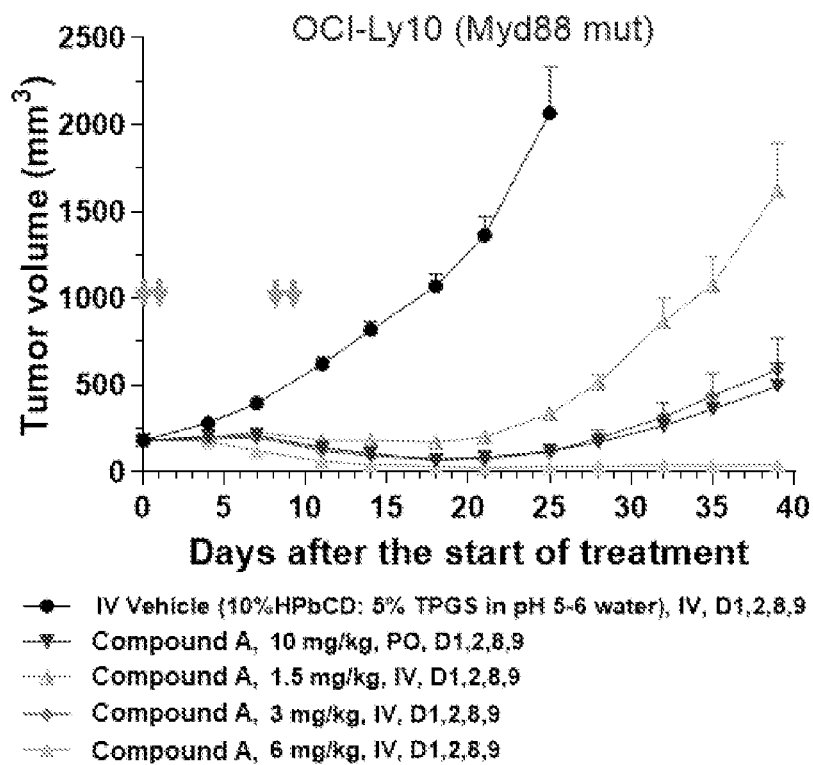

FIG. 3 shows the minimum efficacious dose results for QW and BIW schedules of Compound A in OCI-Ly10 tumor xenographs and that intermittent dosing schedules are efficacious in vivo. Compound A induces regression when dosed BIW every 3 weeks and IV and PO dosing were both equally active on QW and BIW schedules. BIW dosing requires lower weekly exposure than QW.

FIG. 4 shows that Compound A gives high tissue exposure relative to plasma and sustained PD effect following a single dose. Tumor shows relatively slower clearance compared to spleen, which has CL similar to plasma. The efficacy was consistent with potent degradation of IRAK4 and Ikaros with Ikaros degradation faster than IRAK4. Similar data was observed in SUDHL2 xenograph, which is prepared substantially as described above using OCI-LY10.

Table 10 lists OCI-Ly10 tumor xenograph results for various schedules.

TABLE 10

OCI-Ly10 Activity on Various Schedules

| Activity | Dose (mg/kg) | ROA | Schedule | TGI (D14) | CR | PR | SD | PD | Notes |
|---|---|---|---|---|---|---|---|---|---|
| Insufficient | 5 | PO | D1-4, 15-18 | 62 | | | 6 | 1 | All tumors growing after D14 |
| | 5 | PO | D1-7 | 75 | | 2 | 5 | | All tumors growing after D14 |
| | 15 | PO | D1, 8, 15 | 83 | | | 5 | | 3/5 show some regression; 2/5 are growing slightly |
| Minimal | 10 | PO | D1, 2, 8, 9 | 88 | | 2 | 3 | | All show tumor regression and continue trending down |
| | 3 | IV | D1, 2, 8, 9 | 89 | | 3 | 2 | | All tumors shrank and continue to trend down |
| | 3 | IV | D1, 4, 8, 11 | 89 | | 3 | 2 | | All tumors shrank and continue to trend down |
| | 10 | PO | D1-3 | 82 | | 5 | 1 | 1 | All SD show some regression |
| | 10 | PO | D1, 4, 8, 11 | 85 | | 5 | 2 | | 6 PR and 1 near PR on D18; tumors continue to shrink |
| | 10 | PO | D1-4, 15-18 | 87 | | 7 | | | All tumors shrank significantly from D10 |
| | 15 | PO | D1, 2, 8, 9 | 91 | | 7 | | | Very Active: Tumors shrank significantly from D10 |
| | 6 | IV | D1, 2, 8, 9 | 94 | | 5 | | | |
| | 12 | IV | D1, 8, | 94 | | 5 | | | All show tumor regression and continue trending down |
| Optimal | 30 | PO | D1, 8, 15 | 96 | 2 | 5 | | | |
| | 10 | PO | D1-7 | 96 | 1 | 6 | | | BENCHMARK |
| | 20 | PO | D1-3 | 96 | 1 | 6 | | | |
| | 10 | PO | D1-7 | 97 | 1 | 6 | | | |
| | 60 | PO | D1 | 97 | 2 | 5 | | | |
| | 30 | PO | D1, 4, 8 | 97 | 3 | 4 | | | Tumors continue to regress at D18 (5CR, 2PR) |
| | 30 | PO | D1,2 | 99 | 4 | 3 | | | 6 CR by D18 |
| | 30 | PO | D1-3 | 99 | 4 | 3 | | | 7 CR by D18 |
| | 45 | PO | D1,2 | 99 | 4 | 3 | | | 7 CR by D18 |

ROA (route of administration);
TGI (tumor growth inhibition);
PR (partial response);
CR (complete response);
SD (stable disease);
PD (progressive disease).

Figure 9:
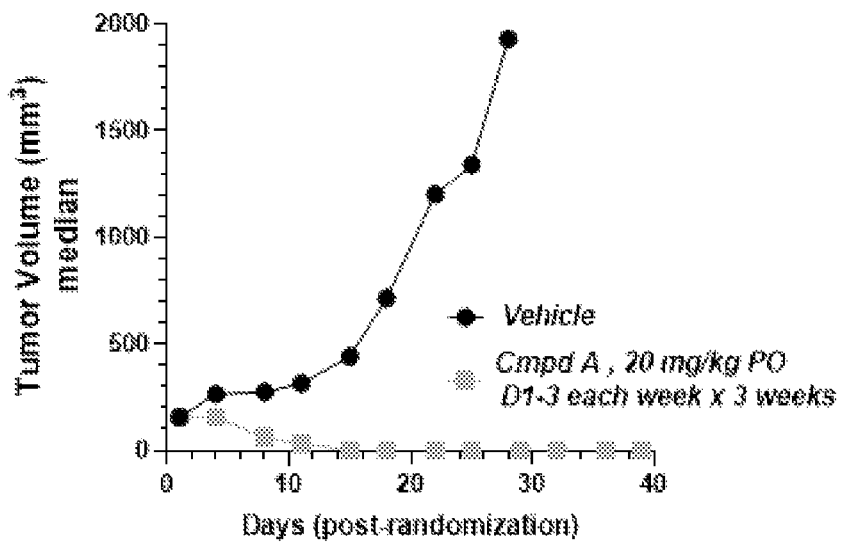
FIG. 9 shows regressions in MYD88-mutant patient-derived xenograph (PDX) models using Compound A.

FIG. 9 shows regressions in MYD88-mutant patient-derived xenograph (PDX) models using Compound A. Table 10A shows results of the PDX models.

TABLE 10A

PDX Results.

| Model | MYD88 | CD79B | TNFAIP3 | Other | Cmpd A (% TGI) |
|---|---|---|---|---|---|
| LY14019 | L265P | MT | MT | | 100 |
| LY2264 | L265P | MT | | IRF4 | 100 |
| LY2298 | L265P | MT | | BCL2/BCL6 | 90 |
| LY12699 | L265P | MT | | | 87 |
| LY2345 | WT | | MT | | 70 |
| LY2301 | WT | | | | 30 |
| LY0257 | L265P | | | BCL2/BCL6/IKZF3 | 0 |

Compound A dosed orally shows strong tumor growth inhibition (>85% TGI) in 4/5 MYD88-mutant DLBCL PDX models. Activity is observed regardless of co-mutations that activate NFkB and IRF4 pathways. The non-responsive MYD88$^{MT}$ model LY0257 harbors a mutation in Aiolos and is reported to be insensitive to lenalidomide. Lower tumor growth inhibition observed in MYD88-wild type PDX may be consistent with IMiD activity of Compound A Example 7

Exploratory Non-Human Primate Safety 7.1 Single Intravenous Bolus Administration to Male and Female Cynomolgus Monkeys

TABLE 7-1-1

STUDY DESIGN

| | | | Treatment | | | | | |
|---|---|---|---|---|---|---|---|---|
| Group No. | No. of animals | Test Articles | Dose (mg/kg) | Dose Volume (mL/kg) | Target Dose Concentration (mg/mL) | Vehicle | Route | Comment |
| 1 | 1 male + 1 female | Compound A | 0 | 1 | 0 | 10% HPBCD:2% TPGS | IV Bolus | Control group, Single dosing on day 1 and Day 2 |
| 2 | 1 male + 1 female | Compound A | 1 | 1 | 1 | 10% HPBCD:2% TPGS | IV Bolus | Single dosing on day 1 |
| 3 | 2 male + 2 female | Compound A | 2.5 | 1 | 2.5 | 10% HPBCD:2% TPGS | IV Bolus | Single dosing on day 1 |
| 4 | 1 male + 1 female | Compound A | 2.5 | 1 | 2.5 | 10% HPBCD:2% TPGS | IV Bolus | Single dosing on day 1 and day 2 |
| 5 | 1 male + 1 female | Compound A | 5 | 1 | 5 | 10% HPBCD:2% TPGS | IV Bolus | Single dosing on day 1 |

Note:
1. 10% HP-b-CD is 10% hydroxypropyl beta cyclodextrim.

TABLE 7-1-2

SAMPLE COLLECTION

| | | | Sampling time point (hr) | | | | | | | | | | | | |
|---|---|---|---|---|---|---|---|---|---|---|---|---|---|---|---|
| Group | Dosage (mg/kg) | Animal No. | Predose[a,b] | 0.5 | 1 | 2 | 4 | 8 | 12 | 24[a] (Day 2) | 48 (Day 3) | 72 (Day 4) | 96 (Day 5) | 120 (Day 6) | 168[a,b] (Day 8) | Day 14[b] |
| 1 | 0 | 1001, 1501 | PD, CP | — | — | — | — | — | — | PD | CP | — | — | — | PD, CP | CP |
| 2 | 1 | 2001, 2501 | PD, CP | PK | PK | PK | PK | PK | PK | PK, PD, PK CP | PK | PK | PK | PK, PD, CP | CP |
| 3 | 2.5 | 3001, 3501, 3002, 3502 | PD, CP | PK | PK | PK | PK | PK | PK | PK, PD, PK CP | PK | PK | PK | PK, PD, CP | CP |
| 5 | 5 | 5001, 5501 | PD, CP | PK | PK | PK | PK | PK | PK | PK, PD, PK CP | PK | PK | PK | PK, PD, CP | CP |

[a]Extra blood at predose, 24 hr, Day 8 will be collected for whole blood lysate preparaion.
[b]Extra blood at predose, 48 hr, Day 8 and Day 14 will be collected for hemoatology, clinical chemistry tests.

| | | | | | Sampling time point (hr) | | | | | | |
|---|---|---|---|---|---|---|---|---|---|---|---|
| Group | Dosage (mg/kg) | Animal No. | Day 1- Predose[a,b] | Day 1- 0.5 h | Day 1- 1 hr | Day 1- 2 h | Day 1- 4 h | Day 1- 8 h | Day 1- 12 h | Day 1- 24[a,b] (Day2) | Day 2- 0.5 h | Day 2- 1 hr |
| 4 | 2.5 | 4001, 4501 | PD, CP | PK | PK | PK | PK | PK | PK | PD | PK | PK |

| | | | | Sampling time point (hr) | | | | | | |
|---|---|---|---|---|---|---|---|---|---|---|
| Group | Day 2- 2 h | Day 2- 4 h | Day 2- 8 h | Day 2- 12 h | Day 2- 24[a] (Day 3) | Day 2- 48 h[b] (Day 4) | Day 2- 96 h (Day 6) | Day 2- 120 h (Day 7) | Day 2- 144 h[a,b] (Day 8) | Day 2- 168 h[a,b] (Day 9) | Day 14[b] |
| 4 | PK | PK | PK | PK | PK, PD | PK, CP | PK | PK | PK, CP | PK, PD | CP |

[a]Extra blood at Day 1-predose, Day 1-24 h, Day 2-24 h and Day 9 will be collected for whole blood lysate preparation.
[b]Extra blood at Day 1-predose, Day 2-48 h, Day 8 and Day 14 will be collected for hematology, clinical chemistry tests.

Body weight measurement at pre-dose on Day 1, Day 4, Day 7, Day 14. Monitor clinical observation of the animal for 14 days post dose.

PK refers to plasma samples.

Procedure to prepare whole blood lysate for PD:

Collect enough blood to have (2) aliquots. Each aliquot will be 200 uL.

1) Prepare BD lyse/Fix buffer 5×

From BD product insert "dilute the required amount of BD Phosflow™ Lyse/Fix Buffer (5× concentrate) 1:5 with deionoized or distilled water (at room temperature) and then pre-warm the solution to 37° C. The 1× working solution should be made fresh for each experiment and any remaining solution at the end of the experiment should be discarded."

2) Fix cells by transferring the 200 uL of blood to 1.8 mL of BD Lyse/Fix Buffer (*1:10 dilution).

3) Incubate for 10 minutes at room temperature.

4) Spin cells down at 1400 rpm for 5 minutes. Aspirate and wash with 10 mM PBS/0.5% BSA (Add this buffer for final volume of 10 mL to spin down)

5) transfer cells to 1.5 mL centrifuge tubes with 1.0 mL of PBS/0.5% BSA buffer spin cells down at 1400 rpm for 5 minutes.

6) Aspirate and freeze down cell pellet. (pure cell pellet with no liquid)

*If lysis appears incomplete can adjust to 1:20 dilution (200 uL of blood to 3.8 mL of BD/Lyse/Fix buffer.

Blood Collection for Hematology

Whole blood (at least 1.0 mL) at 168 hours post dose will be collected from the experimental animals into commercially available tubes with Potassium (K2) EDTA at room temperature (RT). The blood samples will be sent to clinical pathology Lab in RT and tested for hematology parameters.

Hematology test items will be performed as below:

| Hematology | |
|---|---|
| Erythrocyte count (RBC) | Red cell distribution width (RDW) |
| Hematocrit (HCT) | Platelet count (PLT) |
| Hemoglobin (HGB) | Mean platelet volume (MPV) |
| Mean corpuscular volume (MCV) | Leukocyte counts (WBC) and Differential (absolute and percent) |
| Mean corpuscular hemoglobin (MCH) | Absolute reticulocyte count(Retic) |
| Mean corpuscular hemoglobin concentration (MCHC) | |

Serum Processing for Clinical Chemistry

Whole blood samples (approximately 1.0 mL) without anticoagulant at 168 hours post dose will be collected and held at RT and up-right for at least 30 minutes and sent to clinical pathology Lab for analysis.

Clinical chemistry test items will be performed as below:

| Clinical Chemistry | |
|---|---|
| Alkaline Phosphatase (ALP) | Total Protein (TP) |
| Alanine Aminotransferase (ALT) | Albumin (ALB) |
| Aspartate Aminotransferase (AST) | g-glutamyltransferase (GGT) |
| Bilirubin, total (TBIL) | Globulin (GLB) |
| Phosphorus (P) | Albumin/Globulin Ratio |
| Creatinine (CRE) | Sodium (Na) |
| Glucose (GLU) | Chloride (Cl) |
| Calcium (Ca) | Triglycerides (TG) |
| Total Cholesterol (TCHO) | Urea (UREA) |
| Potassium (K) | |

Study Objective

The objective of this study is to determine the pharmacokinetics of Compound A following single intravenous bolus administrations of Compound A in male and female cynomolgus monkeys. The test article will be measured in plasma at selected time points for up to 14 days post dosing.

Test Article and Vehicle Information

Test Article

| Name: | Physical State | Chemical Formula | MW/FW (g/mol) | Purity (%) | C.F. |
|---|---|---|---|---|---|
| Compound A | Powder | C45H48F3N7O6S | 871/871 | 98.9 | 1.0111 |

| Storage Conditions: | Desiccate at room temperature, protect from light |
|---|---|
| Dose Preparation: | Doses will be prepared according to the instructions. A copy of the instructions, as well as details of preparation will be maintained in the study records. |
| Dose Solution Analysis Samples: | After each dose preparation, remove at least 20 μL from the formulations, transfer the aliquots into polypropylene micro-centrifuge tubes and stored at −60° C. or lower until assayed in duplicate for dose validation. |
| Disposition of Remaining Test Article Formulation: | Remaining formulations will be stored room temperature. |

Test System Identification
Animal Specifications

| | |
|---|---|
| Species | Cynomolgus monkeys |
| Justification for Species Selection | This is an acceptable species to support PK studies for compounds intended to use in humans. |
| History of Dosing | Non-naïve animals |
| Body Weight Range | ≥2.5 kg |
| Age | ≥2 years old |
| Sex | Male and Female |
| Number of Animals for Acclimation | 8 males and 8 females |
| Number of Animals for Dosing | 6 males and 6 females |
| Justification for number Animals | The number of animals in each group is the minimum number of animals necessary for assessment of inter-animal variability. |
| Selection of Animals | 8 males and 8 females will be selected and will have undergone a physical examination for general health. 6 males and 6 females, confirmed as being healthy, will be assigned to study. |
| Acclimation Period | Selected animals will be acclimated prior to the study. |

Animal Care
Environmental Conditions

The room(s) will be controlled and monitored for relative humidity (targeted mean range 40% to 70%, and any excursion from this range for more than 3 hours will be documented as a deviation) and temperature (targeted mean range 18° to 26° C., and any excursion from this range will be documented as a deviation) with 10 to 20 air changes/hour. The room will be on a 12-hour light/dark cycle except when interruptions are necessitated by study activities.

Housing

Animals will be individually housed in stainless-steel mesh cages during in-life.

Diet and Feeding

Animals will be fed twice daily. Stock monkeys will be fed approximately 120 grams of Certified Monkey Diet daily. These amounts can be adjusted as necessary based on food consumption of the group or an individual body weight changes of the group or an individual and/or changes in the certified diet. In addition, animals will receive fruit daily as nutritional enrichment.

Feeding design refer to Table 7-1-1.

Drinking Water

RO (reverses osmosis) water will be available to all animals, ad libitum.

Feed and Water Analyses

RO water was analyzed every three months and every batch of feed will be analyzed before using. Feed and water analyses will be maintained in the facility records.

Environmental Enrichment

Enrichment toys will be provided. Fresh fruits purchased from human food suppliers will be supplied daily, except during periods of fasting.

Administration of Dose Formulation

Observations and Examinations
Clinical Observations

Twice daily (approximately 9:30 a.m. and 4:00 p.m.), Cage-side observations for general health and appearance will be done. Animals will be given physical examination prior to study initial to confirm animals' health. Day of dosing: before and after dosing, and before and after each PK sample time point through 24 hour PK sample. Twice daily thereafter. General condition, behavior, activity, excretion, respiration or other unusual observations noted throughout the study will be recorded in the raw data. When necessary, additional clinical observations will be performed and recorded.

Body Weight

All animals will be weighed on the dosing day prior to dosing to determine the dose volume to be administered, and again weekly thereafter.

Blood and Urine Samples Collection

Blood: All blood samples will be collected from a peripheral vessel from restrained, non-sedated animals.

Animals: All available, all groups

Blank Plasma: Whole blood will be collected from available stock animal into commercially available tubes containing Potassium (K2) EDTA on wet ice and processed for plasma. The plasma will be pooled to serve as blank plasma.

Pre-Dose and Post-Dose

Blood volume: Approximately, 0.5 mL, for each time point

Anticoagulant: Potassium ($K_2$) EDTA

Frequency: Refer to Table 7-1-2. Actual sample collection times will be recorded in the study records. For samples collected within the first hour of dosing, a ±1 minute is acceptable. For the remaining time points, samples that are taken within 5% of the scheduled time are acceptable and will not be considered as protocol deviation.

Sample Processing for plasma: 12.5 µL 20% Tween 20 will be added into a commercial tube containing Potassium (K2) EDTA (0.85-1.15 mg) on wet ice, 0.4~0.5 ml blood will be collected into these tubes and processed for plasma. Samples will be centrifuged (3,000×g for 10 minutes at 2 to 8° C.) within one hour of collection. The plasma samples (0.2 mL/Sample) will be transferred into labeled polypropylene micro-centrifuge tubes, respectively, and stored frozen in a freezer set to maintain −60° C. or lower.

Sample Assay and Storage
Dose formulation concentration verification

A LC/UV or LC/MS/MS method will be developed with a calibration curve consisting of 6 calibration standards.

The concentrations of the test compound in dose formulation samples will be determined by the LC/UV or LC/MS/MS method.

Acceptance criteria for an analytical run: at least of 5 of 6 calibration standards should be within 20% of nomi-

| | |
|---|---|
| Administration Route: | Intravenously by bolus injection via the cephalic or saphenous vein |
| Justification for the Dose Level: | Dose levels chosen to characterize the pharmacokinetics of test article in monkeys over adose and plasma concentration range that approximate expected efficacious exposures, with moderate exposure multiples assuming exposure increases with dose. These doses and resultant exposures are not expected to cause any morbidity or toxicity in the NHP based on responses in rodents across similar dose ranges. |
| Justification for the Administration Route: | This administration route is consistent with the proposed initial route of human administration or is needed to meet the study objective. |
| Dose Administration: | The dose formulation will be administered per facility SOPs. Intravenous (IV): The IV doses will be administered by slow injection via the cephalic or saphenous vein. The vein used for the dosing will not be used for the blood sample collection for the first 4 hours post dose. | nal values by using LC/UV method and 30% of nominal values by using LC/MS/MS method.

Bioanalytical method development and sample analysis

LC-MS/MS method development:
1. A LC-MS/MS method for the quantitative determination of test compound in biological matrix will be developed under non-GLP compliance.
2. A calibration curve with at least 7 non-zero calibration standards will be applied for the method including LLOQ.
3. A set of QC samples consisting of low, middle, and high concentration will be applied for the method.
4. N in 1 cassette LC-MS/MS method can be developed for samples coming from different studies as long as these studies belong to same sponsor and the interference among all cassette analytes will be evaluated during the method development.
5. Cassette administration assay could be performed if the mass difference (ΔMass) among different analytes is more than 4 Da. In this case, interference evaluation is not necessary. If the ΔMass among different analytes is less than 4 Da, there is a potential risk that interference would occur during LC-MS/MS analysis. If such kind cassette assay is still requested by the study sponsor, interference between analytes will not be evaluated but the LC separation of those analytes by using a generic method will be tried. If these analytes could not be separated, notice to client will be conducted and documentation on experiment record are needed.
6. Biological sample in matrix other than plasma can be diluted with plasma first and then quantified against plasma calibration curve. And the corresponding dilution QCs to insure the dilution accuracy and matrix difference, will be inserted into analytical run.

Sample analysis:
1. If sample number within a batch is ≤12, at least one set of standard curve separated with two parts through begin and end of the sequence, should be included in the run and QCs are not required. The recommended injection order is C8, C6, C4, C2, study samples, C7, C5, C3, C1.
2. If sample number within a batch >12, one standard curve and two sets of QC samples with low, middle and high concentrations will be applied for bioanalysis, meanwhile, QC sample number should be more than 5% of study sample number.
3. Samples, coming from one client with same types of matrix though in different studies, are allowed to be quantified in one analysis run by using the developed N in 1 cassette LC-MS/MS method.
4. Biological samples in matrix other than plasma are recommended to be diluted with plasma and then quantified against plasma calibration curve. The corresponding dilution QCs to insure the dilution accuracy and matrix difference, will be inserted into analytical run. If sponsor requests specifically, biological samples are then to be quantified against calibration curves in their own corresponding matrices.

Acceptance criteria:
1. Linearity: ≥75% STDs is back calculated to within ±20% of their nominal values in biofluid and within 25% of their nominal values in tissue and feces sample.
2. Accuracy: ≥67% all QC samples is back calculated to within ±20% of their nominal values for biofluid and within 25% of their nominal values for tissue and feces samples.
3. Specificity: The mean calculated concentration in the single blank matrix should be ≤50% LLOQ.
4. Sensitivity:
    4.1 If the biological samples in matrix other than plasma are diluted with plasma and quantified against plasma calibration curve, the LLOQ of plasma calibration curve will be tried to target ≤2 ng/mL, which LLOQ is equivalent to ≤4 ng/mL in biological matrix other than plasma (if dilution 2 folds is applied).
    4.2 If the biological samples are quantified against the calibration curves prepared by their corresponding matrix, the LLOQ will be tried to target ≤3 ng/mL. Any adjustment of LLOQ will inform sponsor in advance
5. Carryover: The mean calculated carry-over peak area in the blank matrix immediately after the highest standard injection should be less than that of LLOQ. If the carryover couldn't meet the criteria, he impact of the carryover on unknown samples should be evaluated according to the below procedure:
    Carryover evaluation should be estimated according to absolute carryover. Carryover contribution is calculated by the area ratio of the blank with the highest carryover (Area max of carryover blank) to the ULOQ with the minimum calculated value (Area min of ULOQ); Carryover impact is calculated by the area ratio of one injection (Area of one injection) to the following injection (Area of the following injection); Absolute carryover is calculated by carryover contribution multiplies carryover impact, the value of absolute carryover should be below 20%.
    Carryover contribution=Area max of carryover blank/Area min of ULOQ
    Carryover impact=Area of one injection/Area of the following injection
    Absolute carryover=Carryover contribution*Carryover impact 7.2 Pharmacokinetic and Tolerability Characterization following Intravenous Bolus Administration to Male and Female Cynomolgus Monkeys

TABLE 7-2-1

STUDY DESIGN

| Group No. | No. of animals | Test Articles | Dose (mg/kg) | Dose Volume (mL/kg) | Target Dose Concentration (mg/mL) | Vehicle | Route | Comment |
|---|---|---|---|---|---|---|---|---|
| 1 | 1 male + 1 female | Compound A | 0 | 1 | 0 | 5 wt % TPGS in 0.1M Acetate | IV Bolus | Control group, Single dosing on day 1 and Day 2 |
| 2 | 1 male + 1 female | Compound A | 10 | 1 | 10 | 5 wt % TPGS in 0.1M Acetate | IV Bolus | Single dosing on day 1 |

TABLE 7-2-1-continued

STUDY DESIGN

Treatment

| Group No. | No. of animals | Test Articles | Dose (mg/kg) | Dose Volume (mL/kg) | Target Dose Concentration (mg/mL) | Vehicle | Route | Comment |
|---|---|---|---|---|---|---|---|---|
| 3 | 1 male + 1 female | Compound A | 20 | 1 | 20 | 5 wt % TPGS in 0.1M Acetate | IV Bolus | Single dosing on day 1 |
| 4 | 1 male + 1 female | Compound A | 5 | 1 | 5 | 5 wt % TPGS in 0.1M Acetate | IV Bolus | Single dosing on day 1 and day 2 |
| 5 | 1 male + 1 female | Compound A | 10 | 1 | 10 | 5 wt % TPGS in 0.1M Acetate | IV Bolus | Single dosing on day 1 |

Note:
10% HP-b-CD is 10% hydroxypropyl beta cyclodextrin.

TABLE 7-2-2

SAMPLE COLLECTION

| | | | Sampling time point (hr) | | | | | | | | | | | | |
|---|---|---|---|---|---|---|---|---|---|---|---|---|---|---|---|
| Group | Dosage (mg/kg) | Animal No. | predose$^{a,b}$ | 0.5 | 1 | 2 | 4 | 8 | 12 | 24$^a$ (Day 2) | 48 (Day 3) | 72 (Day 4) | 96$^a$ (Day 5) | 120 (Day 6) | 168$^{a,b}$ (Day 8) | Day 11$^b$ | Day 14$^b$ |
| 1 | 0 | 1001, 1501 | PD, CP | — | — | — | — | — | — | PD | CP | — | PD | — | PD, CP | CP | CP |

$^a$Extra blood at predose, 24 hr, 96 hr, Day 8 will be collected for whole blood lysate preparation.
$^b$Extra blood at predose, 48 hr, Day 8, Day 11 and Day 14 will be collected for hematology, clinical chemistry tests.

SAMPLE COLLECTION

| | | | Sampling time point (hr) | | | | | | | | | | | | |
|---|---|---|---|---|---|---|---|---|---|---|---|---|---|---|---|
| Group | Dosage (mg/kg) | Animal No. | predose$^{a,b}$ | 0.5 | 1 | 2 | 4 | 8 | 12 | 24$^a$ (Day 2) | 48 (Day 3) | 72 (Day 4) | 96$^a$ (Day 5) | 120 (Day 6) | 168$^{a,b}$ (Day 8) | Day 11$^b$ | Day 14$^b$ |
| 2 | 10 | 2001, 2501 | PD, CP | PK | PK | PK | PK | PK | PK | PK, PD | PK CK | PK, PD | PK | PK | PK, PD, CP CP | CP | CP |
| 3 | 20 | 3001, 3501 | PD, CP | PK | PK | PK | PK | PK | PK | PK, PD | PK CK | PK, PD | PK | PK | PK, PD, CP CP | CP | CP |

$^a$Extra blood at predose, 24 hr, 72 hr, Day 8 will be collected for whole blood lysate preparation.
$^b$Extra blood at predose, 48 hr, Day 8, Day 11 and Day 14 will be collected for hematology, clinical chemistry tests.

| | | | Sampling time point (hr) | | | | | | | | |
|---|---|---|---|---|---|---|---|---|---|---|---|
| Group | Dosage (mg/kg) | Animal No. | predose$^{a,b}$ | Day 1- 0.5 h | Day 1- 1 hr | Day 1- 2 h | Day 1- 4 h | Day 1- 8 h | Day 1- 12 h | Day 1- 24$^a$ (Day 2) | Day 2- 0.5 h | Day 2- 1 hr |
| 4 | 5 | 4001, 4501 | PD, CP | PK | PK | PK | PK | PK | PK | PK, PD | PK | PK |
| 5 | 10 | 5001, 5501 | PD, CP | PK | PK | PK | PK | PK | PK | PK, PD | PK | PK |

| | | | | Sampling time point (hr) | | | | | | | | |
|---|---|---|---|---|---|---|---|---|---|---|---|---|
| Group | Day 2- 2 h | Day 2- 4 h | Day 2- 8 h | Day 2- 12 h | Day 2- 24$^a$ (Day 3) | Day 2- 48 h$^b$ (Day 4) | Day 2- 72 h$^a$ (Day 4) | Day 2- 96 h (Day 6) | Day 2- 120 h (Day 7) | Day 2- 144 h$^b$ (Day 8) | Day 2- 168 h$^a$ (Day 9) | Day 11$^b$ | Day 14$^b$ |
| 4 | PK | PK | PK | PK | PK, PD | PK, CP | PD | PK | PK | PK, CP | PK, PD | CP | CP |
| 5 | PK | PK | PK | PK | PK, PD | PK, CP | PD | PK | PK | PK, CP | PK, PD | CP | CP |

$^a$Extra blood at predose, Day 1-24 h, Day 2-24 h, Day 2-72 h and Day 9 will be collected for whole blood lysate preparation.
$^b$Extra blood at predose, Day 2-48 h, Day 8, Day 11 and Day 14 will be collected for hematology, clinical chemistry tests.

Body weight measurement at pre-dose on Day 1, Day 4, Day 7, Day 14. Monitor clinical observation of the animal for 14 days post dose.

PK refers to plasma samples.

Procedure to prepare whole blood lysate for PD:

Collect enough blood to have (2) aliquots. Each aliquot will be 200 uL.

1) Prepare BD lyse/Fix buffer 5×

From BD product insert "dilute the required amount of BD Phosflow™ Lyse/Fix Buffer (5× concentrate) 1:5 with deionoized or distilled water (at room temperature) and then pre-warm the solution to 37° C. The 1× working solution should be made fresh for each experiment and any remaining solution at the end of the experiment should be discarded."

2) Fix cells by transferring the 200 uL of blood to 1.8 mL of BD Lyse/Fix Buffer (*1:10 dilution).

3) Incubate for 10 minutes at room temperature.

4) Spin cells down at 1400 rpm for 5 minutes. Aspirate and wash with 10 mM PBS/0.5% BSA (Add this buffer for final volume of 10 mL to spin down)

5) transfer cells to 1.5 mL centrifuge tubes with 1.0 mL of PBS/0.5% BSA buffer spin cells down at 1400 rpm for 5 minutes.

6) Aspirate and freeze down cell pellet. (pure cell pellet with no liquid)

*If lysis appears incomplete can adjust to 1:20 dilution (200 uL of blood to 3.8 mL of BD/Lyse/Fix buffer Blood Collection for Hematology Whole blood (at least 1.0 mL) at 168 hours post dose will be collected from the experimental animals into commercially available tubes with Potassium (K2) EDTA at room temperature (RT). The blood samples will be sent to clinical pathology Lab in RT and tested for hematology parameters.

Hematology test items will be performed as below:

| Hematology | |
|---|---|
| Erythrocyte count (RBC) | Red cell distribution width (RDW) |
| Hematocrit (HCT) | Platelet count (PLT) |
| Hemoglobin (HGB) | Mean platelet volume (MPV) |
| Mean corpuscular volume (MCV) | Leukocyte counts (WBC) and Differential (absolute and percent) |
| Mean corpuscular hemoglobin (MCH) | Absolute reticulocyte count(Retic) |
| Mean corpuscular hemoglobin concentration (MCHC) | |

Serum Processing for Clinical Chemistry

Whole blood samples (approximately 1.0 mL) without anticoagulant at 168 hours post dose will be collected and held at RT and up-right for at least 30 minutes and sent to clinical pathology Lab for analysis.

Clinical chemistry test items will be performed as below:

| Clinical Chemistry | |
|---|---|
| Alkaline Phosphatase (ALP) | Total Protein (TP) |
| Alanine Aminotransferase (ALT) | Albumin (ALB) |
| Aspartate Aminotransferase (AST) | g-glutamyltransferase (GGT) |
| Bilirubin, total (TBIL) | Globulin (GLB) |
| Phosphorus (P) | Albumin/Globulin Ratio |
| Creatinine (CRE) | Sodium (Na) |
| Glucose (GLU) | Chloride (Cl) |
| Calcium (Ca) | Triglycerides (TG) |
| Total Cholesterol (TCHO) | Urea (UREA) |
| Potassium (K) | |

Study Objective

The objective of this study is to determine the pharmacokinetics and tolerability of Compound A following intravenous bolus administrations of Compound A on a single day or two consecutive days in male and female cynomolgus monkeys. The test article will be measured in plasma at selected time points for up to 14 days post dosing.

Test Article and Vehicle Information

Test Article

| Name: | Physical State | Chemical Formula | MW/FW (g/mol) | Theoretical Potency* (%) | C.F. |
|---|---|---|---|---|---|
| Compound A | Powder | C45H48F3N7O6S | 871/871 | 20% | 5 |

*Test article is comprised of 20% active (Compound A) and 80% excipient (HPBCD)

| Storage Conditions: | Desiccate at room temperature, protect from light |
|---|---|
| Handling Instructions: | Standard laboratory precautions |

| Dose Preparation: | Doses will be prepared according to instructions provided by the sponsor. A copy of the instructions, as well as details of preparation will be maintained in the study records. |
|---|---|
| Dose Solution Analysis Samples: | After each dose preparation, remove at least 20 µL from the formulations, transfer the aliquots into polypropylene micro-centrifuge tubes and stored at −60° C. or lower until assayed in duplicate for dose validation. |
| Disposition of Remaining Test Article Formulation: | Remaining formulations will be stored room temperature. |
| Disposition of Remaining Test Article (dry powder or solid): | Remaining test article will be stored at room temperature desiccated, and protected from light and will be shipped back to sponsor or discarded 6 months after the final report is signed or at approval of sponsor. |

Vehicle and formulation preparation

20%:80% Compound A:HPBCD SDD Solution Preparation Protocol:

Purpose: To prepare a 20 mgA/mL solution of 20%:80% Compound A:HPBCD SDD in an aqueous vehicle comprised of 5 wt % TPGS in 0.1 M Acetate suitable for IV dosing in NHP.

| Test Article: 20%:80% Compound A:HPBCD SDD | | | | | |
|---|---|---|---|---|---|
| Name: | Physical State | Chemical Formula | MW/FW (g/mol) | Theoretical Potency* (%) | C.F. |
| Compound A | Powder | C45H48F3N7O6S | 871/ 871 | 20% | 5 |

*Test article is comprised of 20% active (Compound A) and 80% excipient (HPBCD)

Materials

Purified water, Type II or HPLC grade

Glacial acetic acid

TPGS

Test Article: 20%:80% Compound A: HP-β-CD SDD (DBR-KY1-004-A)

Vehicle Preparation 5 wt % TPGS, 0.1 M Acetate, pH 3.5 a. Add 0.572 mL glacial acetic acid to 85 mL purified water, mix until fully dissolved b. pH adjust to pH 3.5 with NaOH c. QS with water to 100 mL d. Add 5.26 g TPGS and mix until fully dissolved IV Solution Preparation
a. Weigh test article as specified in formulation table into an appropriately sized vessel
b. Add vehicle and immediately mix thoroughly until test article has fully dissolved
  a. Solution should appear bright yellow and translucent with no visible particles
  b. Avoid excessive vortexing to prevent bubble formation
  c. pH adjust solution slowly with constant vigorous mixing to pH 6.0 using 5 N NaOH.

Test System Identification
Animal Specifications

| | |
|---|---|
| Species | Cynomolgus monkeys |
| Justification for Species Selection | This is an acceptable species to support PK studies for compounds intended to use in humans. |

| | |
|---|---|
| Administration Route: | Intravenously by bolus injection via the cephalic or saphenous vein |
| Justification for the Dose Level: | Dose levels chosen to characterize the pharmacokinetics of test article in monkeys over adose and plasma concentration range that approximate expected efficacious exposures, with moderate exposure multiples assuming exposure increases with dose. These doses and resultant exposures are not expected to cause any morbidity or toxicity in the NHP based on responses in rodents across similar dose ranges. |
| Justification for the Administration Route: | This administration route is consistent with the proposed initial route of human administration or is needed to meet the study objective. |
| Dose Administration: | The dose formulation will be administered per facility SOPs. Intravenous (IV): The IV doses will be administered by slow injection via the cephalic or saphenous vein. The vein used for the dosing will not be used for the blood sample collection for the first 4 hours post dose. |

-continued

| | |
|---|---|
| History of Dosing | Non-naïve animals |
| Body Weight Range | ≥2.5 kg |
| Age | ≥2 years old |
| Sex | Male and Female |
| Number of Animals for Acclimation | 7 males and 7 females |
| Number of Animals for Dosing | 5 males and 5 females |
| Justification for number of Animals | The number of animals in each group is the minimum number of animals necessary for assessment of inter-animal variability. |
| Selection of Animals | 7 males and 7 females will be selected from available stock animals. Animals will have undergone a physical examination for general health. 5 males and 5 females, confirmed as being healthy, will be assigned to study. |
| Acclimation Period | Selected animals will be acclimated prior to the study. |

Animal Care
Environmental Conditions
The room(s) will be controlled and monitored for relative humidity (targeted mean range 40% to 70%, and any excursion from this range for more than 3 hours will be documented as a deviation) and temperature (targeted mean range 18° to 26° C., and any excursion from this range will be documented as a deviation) with 10 to 20 air changes/hour. The room will be on a 12-hour light/dark cycle except when interruptions are necessitated by study activities.

Housing
Animals will be individually housed in stainless-steel mesh cages during in-life Diet and Feeding
Animals will be fed twice daily. Stock monkeys will be fed approximately 120 grams of Certified Monkey Diet daily. These amounts can be adjusted as necessary based on food consumption of the group or an individual body weight changes of the group or an individual and/or changes in the certified diet. In addition, animals will receive fruit daily as nutritional enrichment.

Feeding design refer to Table 7-2-1.

Drinking Water
RO (reverses osmosis) water will be available to all animals, ad libitum.

Feed and Water Analyses
RO water was analyzed every three months and every batch of feed will be analyzed before using. Feed and water analyses will be maintained in the facility records.

Environmental Enrichment
Enrichment toys will be provided. Fresh fruits purchased from human food suppliers will be supplied daily, except during periods of fasting.

Administration of Dose Formulation

Observations and Examinations
Clinical Observations
Twice daily (approximately 9:30 a.m. and 4:00 p.m.), Cage-side observations for general health and appearance will be done. Animals will be given physical examination prior to study initial to confirm animals' health. Day of dosing: before and after dosing, and before and after each PK sample time point through 24 hour PK sample. Twice daily thereafter. General condition, behavior, activity, excretion, respiration or other unusual observations noted throughout the study will be recorded in the raw data. When necessary, additional clinical observations will be performed and recorded.

Body Weight
All animals will be weighed on the dosing day prior to dosing to determine the dose volume to be administered, and again weekly thereafter.

Blood and Urine Samples Collection
Blood: All blood samples will be collected from a peripheral vessel from restrained, non-sedated animals.
Animals: All available, all groups
Blank Plasma: Whole blood will be collected from available stock animal into commercially available tubes containing Potassium (K2) EDTA on wet ice and processed for plasma. The plasma will be pooled to serve as blank plasma.
Pre-Dose and Post-Dose
Blood volume: Approximately, 0.5 mL, for each time point
Anticoagulant: Potassium ($K_2$) EDTA
Frequency: Refer to Table 7-2-2. Actual sample collection times will be recorded in the study records. For samples collected within the first hour of dosing, a ±1 minute is acceptable. For the remaining time points, samples that are taken within 5% of the scheduled time are acceptable and will not be considered as protocol deviation.

Sample Processing for plasma: 12.5 μL 20% Tween 20 will be added into a commercial tube containing Potassium (K2) EDTA (0.85-1.15 mg) on wet ice, 0.4~0.5 ml blood will be collected into these tubes and processed for plasma. Samples will be centrifuged (3,000×g for 10 minutes at 2 to 8° C.) within one hour of collection. The plasma samples (0.2 mL/Sample) will be transferred into labeled polypropylene micro-centrifuge tubes, respectively, and stored frozen in a freezer set to maintain −60° C. or lower.

Sample Assay and Storage

Dose formulation concentration verification

A LC/UV or LC/MS/MS method will be developed with a calibration curve consisting of 6 calibration standards.

The concentrations of the test compound in dose formulation samples will be determined by the LC/UV or LC/MS/MS method.

Acceptance criteria for an analytical run: at least of 5 of 6 calibration standards should be within 20% of nominal values by using LC/UV method and 30% of nominal values by using LC/MS/MS method.

Bioanalytical method development and sample analysis

LC-MS/MS method development:

1. A LC-MS/MS method for the quantitative determination of test compound in biological matrix will be developed under non-GLP compliance.
2. A calibration curve with at least 7 non-zero calibration standards will be applied for the method including LLOQ.
3. A set of QC samples consisting of low, middle, and high concentration will be applied for the method.
4. N in 1 cassette LC-MS/MS method can be developed for samples coming from different studies as long as these studies belong to same sponsor and the interference among all cassette analytes will be evaluated during the method development.
5. Cassette administration assay could be performed if the mass difference (ΔMass) among different analytes is more than 4 Da. In this case, interference evaluation is not necessary. If the ΔMass among different analytes is less than 4 Da, there is a potential risk that interference would occur during LC-MS/MS analysis. If such kind cassette assay is still requested by the study sponsor, interference between analytes will not be evaluated but the LC separation of those analytes by using a generic method will be tried. If these analytes could not be separated, notice to client will be conducted and documentation on experiment record are needed.
6. Biological sample in matrix other than plasma can be diluted with plasma first and then quantified against plasma calibration curve. And the corresponding dilution QCs to insure the dilution accuracy and matrix difference, will be inserted into analytical run.

Sample analysis:

1. If sample number within a batch is <12, at least one set of standard curve separated with two parts through begin and end of the sequence, should be included in the run and QCs are not required. The recommended injection order is C8, C6, C4, C2, study samples, C7, C5, C3, C1.
2. If sample number within a batch >12, one standard curve and two sets of QC samples with low, middle and high concentrations will be applied for bioanalysis, meanwhile, QC sample number should be more than 5% of study sample number.
3. Samples, coming from one client with same types of matrix though in different studies, are allowed to be quantified in one analysis run by using the developed N in 1 cassette LC-MS/MS method.
4. Biological samples in matrix other than plasma are recommended to be diluted with plasma and then quantified against plasma calibration curve. The corresponding dilution QCs to insure the dilution accuracy and matrix difference, will be inserted into analytical run. If sponsor requests specifically, biological samples are then to be quantified against calibration curves in their own corresponding matrices. Acceptance criteria:

1. Linearity: ≥75% STDs is back calculated to within ±20% of their nominal values in biofluid and within 25% of their nominal values in tissue and feces sample.
2. Accuracy: ≥67% all QC samples is back calculated to within ±20% of their nominal values for biofluid and within 25% of their nominal values for tissue and feces samples.
3. Specificity: The mean calculated concentration in the single blank matrix should be ≤50% LLOQ.
4. Sensitivity:
   4.1 If the biological samples in matrix other than plasma are diluted with plasma and quantified against plasma calibration curve, the LLOQ of plasma calibration curve will be tried to target <2 ng/mL, which LLOQ is equivalent to ≤4 ng/mL in biological matrix other than plasma (if dilution 2 folds is applied).
   4.2 If the biological samples are quantified against the calibration curves prepared by their corresponding matrix, the LLOQ will be tried to target ≤3 ng/mL. Any adjustment of LLOQ will inform sponsor in advance
5. Carryover: The mean calculated carry-over peak area in the blank matrix immediately after the highest standard injection should be less than that of LLOQ. If the carryover couldn't meet the criteria, he impact of the carryover on unknown samples should be evaluated according to the below procedure:

Carryover evaluation should be estimated according to absolute carryover. Carryover contribution is calculated by the area ratio of the blank with the highest carryover (Area max of carryover blank) to the ULOQ with the minimum calculated value (Area min of ULOQ); Carryover impact is calculated by the area ratio of one injection (Area of one injection) to the following injection (Area of the following injection); Absolute carryover is calculated by carryover contribution multiplies carryover impact, the value of absolute carryover should be below 20%.

Carryover contribution=Area max of carryover blank/Area min of ULOQ

Carryover impact=Area of one injection/Area of the following injection

Absolute carryover=Carryover contribution*Carryover impact 7.3 Pharmacokinetic Characterization of Compound A following Single or Repeated Oral Administrations to Male and Female Cynomolgus Monkeys

TABLE 7-3-1

STUDY DESIGN

| Group No. | No. of animals | Test Articles | Treatment Dose (mg/kg) | Dose Volume (mL/kg) | Target Dose Concentration (mg/mL) | Vehicle | Route | Comment |
|---|---|---|---|---|---|---|---|---|
| 1 | 1 male + 1 female | Compound A | 50 | 5 | 10 | 10% HP-b-CD | PO | Single dosing on day 1 |
| 2 | 1 male + 1 female | Compound A | 100 | 5 | 20 | 10% HP-b-CD | PO | Single dosing on day 1 |
| 3 | 1 male + 1 female | Compound A | 10 | 5 | 2 | 10% HP-b-CD | PO | Single dosing on day 1 and day 4 |
| 4 | 1 male + 1 female | Compound A | 25 | 5 | 5 | 10% HP-b-CD | PO | Single dosing on day 1 and day 4 |
| 5 | 1 male + 1 female | Compound A | 50 | 5 | 10 | 10% HP-b-CD | PO | Single dosing on day 1 and day 4 |
| 6 | 1 male + 1 female | Compound A | 25 | 5 | 5 | 10% HP-b-CD | PO | Single dosing on day 1 and day 2 |
| 7 | 1 male + 1 female | — | 0 | 5 | 0 | 10% HP-b-CD | PO | Control group, QD X 7 days |
| 8 | 1 male + 1 female | Compound A | 3 | 5 | 0.6 | 10% HP-b-CD | PO | QD X 7 days |

Note:
1. 10% HP-b-CD is 10% hydroxypropyl beta cyclodextrin.
2. QD X 7 days: Consecutive 7 days.
3. Groups 1, 2 : The animals will be fasted overnight before the first dosing day on day 1.
Groups 3, 4, 5: The animals will be fasted overnight before the first dosing day on day 1 and before te last dosing on Day 4, food will be returned at 4 hours post-dose.
Groups 6: The animals will be fasted overnight before the first dosing day on day 1 and before the last dosing on Day 2, food will be returned at 4 hours post-dose. Ensure the animals have 4 hours to get the food between day 1 and day 2.
Group 7 and 8: The animals will be fasted overnight before the first dosing day on day 1 and before the last dosing Day 7, food will be returned at 4 hours post-dose.

TABLE 7-3-2

SAMPLE COLLECTION

| Group | Dosage (mg/kg) | Animal No. | predose[a,b] | 2 | 4 | 8 | 12 | 24[a,b] (Day 2) | 48[b] (Day 3) | 72 (Day 4) | 96 (Day 5) | 120 (Day 6) | 168[a,b] (Day 8) | Day 14[b] |
|---|---|---|---|---|---|---|---|---|---|---|---|---|---|---|
| 1 | 50 | 1001, 1501 | PD, CP | PK | PK | PK | PK | PK, PD | PK, CP | PK | PK | PK | PK, PD, CP | CP |
| 2 | 100 | 2001, 2501 | PD, CP | PK | PK | PK | PK | PK, PD | PK, CP | PK | PK | PK | PK, PD, CP | CP |

[a]Extra blood at predose, 24 hr, Day 8 will be collected for while blood lysate preparation.
[b]Extra blood at predose, 48 hr, Day 8 and Day 14 will be collected for hematology, clinical chemistry tests.

| Group | Dosage (mg/kg) | Animal No. | Day 1- Predose[a,b] | Day 1- 2 h | Day 1- 4 h | Day 1- 8 h | Day 1- 12 h | Day 1- 24[a,b] | Day 1- 48 h | Day 4- predose[a,b] |
|---|---|---|---|---|---|---|---|---|---|---|
| 3 | 10 | 3001, 3501 | PD, CP | PK | PK | PK | PK | PK, PD | CP, PK | PK, PD, |
| 4 | 25 | 4001, 4501 | PD, CP | PK | PK | PK | PK | PK, PD | CP, PK | PK, PD, |
| 5 | 50 | 5001, 5501 | PD, CP | PK | PK | PK | PK | PK, PD | CP, PK | PK, PD, |

-continued

| | Sampling time point (hr) | | | | | | | | | |
|---|---|---|---|---|---|---|---|---|---|---|
| Group | Day 4-<br>2 h | Day 4-<br>4 h | Day 4-<br>8 h | Day 4-<br>12 h | Day 4-<br>24 h[a,b]<br>(Day 5) | Day 4-<br>48 h<br>(Day 6) | Day 4-<br>96 h<br>(Day 8) | Day 4-<br>120 h[a,b]<br>(Day 9) | Day4-<br>168 h[a,b]<br>(Day 11) | Day 14[b] |
| 3 | PK | PK | PK | PK | PK, PD | PK, CP | PK, PD, CP | PK | PK, PD | CP |
| 4 | PK | PK | PK | PK | PK, PD | PK, CP | PK, PD, CP | PK | PK, PD | CP |
| 5 | PK | PK | PK | PK | PK, PD | PK, CP | PK, PD, CP | PK | PK | CP |

[a]Extra blood at Day 1-predose, Day 1-24 h, Day 4-predose, Day 4-24 h and Day 8 will be collected for whole blood lystate preparation.
[b]Exra blood at Day 1-predose, Day 1-48 h, Day 4-predose, Day 4-48 h Day 8 and Day 14 will be collected for hematology, clinical chemistry tests.

| | | | | Sampling time point (hr) | | | | | |
|---|---|---|---|---|---|---|---|---|---|
| Group | Dosage<br>(mg/kg) | Animal<br>No. | Day 1-<br>predose[a,b] | Day 1-<br>2 h | Day 1-<br>4 h | Day 1-<br>8 h | Day 1-<br>12 h | Day 1-<br>24 h[a]<br>(Day 2) | Day 2-<br>2 h |
| 6 | 25 | 6001,<br>6501 | PD, CP | PK | PK | PK | PK | PK, PD | PK |

| | Sampling time point (hr) | | | | | | | | |
|---|---|---|---|---|---|---|---|---|---|
| Group | Day 2-<br>4 h | Day 2-<br>8 h | Day 2-<br>12 h | Day 2-<br>24 h[a]<br>(Day 3) | Day 2-<br>48 h[b]<br>(Day 4) | Day 2-<br>96 h<br>(Day 6) | Day 2-<br>120 h<br>(Day 7) | Day 2-<br>144 h[a,b]<br>(Day 8) | Day 2-<br>168 h[a,b]<br>(Day 9) | Day 14[b] |
| 6 | PK | PK | PK | PK, PD | PK, CP | PK | PK | PK, PD, CP | PK | CP |

[a]Extra blood at Day 1-predose, Day 1-24 h, Day 2-24 h and Day 8 will be collected for whole blood lyste preparation.
[b]Extra blood at Day 1-predose, Day 2-48 h, Day 8 and Day 14 will be collected for hematology, clinical chemistry tests.

| | | | | Sampling time point (hr) | | | | | |
|---|---|---|---|---|---|---|---|---|---|
| Group | Dosage<br>(mg/kg) | Animal<br>No. | Day 1-<br>predose[a,b] | Day 1-<br>2 h | Day 1-<br>4 h | Day 1-<br>8 h | Day 1-<br>12 h | Day 1-<br>24 h[a] | Day 3-<br>predose[a,b] |
| 7 | — | 7001,<br>7501 | PD, CP | — | — | — | — | PD, | PD, CP |
| 8 | 3 | 8001,<br>8501 | PD, CP | PK | PK | PK | PK | PK, PD, | PD, CP |

| | Sampling time point (hr) | | | | | | | | |
|---|---|---|---|---|---|---|---|---|---|
| Group | Day 7-<br>predose | Day 7-<br>2 h | Day 7-<br>4 h | Day 7-<br>8 h | Day 7-<br>12 h | Day 7-<br>24 h[a,b]<br>(Day 8) | Day 7-<br>48 h<br>(Day 9) | Day 7-<br>96 h<br>(Day 11) | Day 7-<br>168 h[a,b]<br>(Day 14) |
| 7 | — | — | — | — | — | PD, CP | — | — | PD, CP |
| 8 | PK | PK | PK | PK | PK | PK, PD CP | PK | PK | PK, PD, CP |

[a]Extra blood at Day 1-predose, Day 1-24 h, Day 3-predose, Day 7-24 h, Day 14 will be collected for while blood lysate preparation.
[b]Extra blood at Day 1-predose, Day 3-predose, Day 7-24 h and Day 14 will be collected for hematology, clinical chemistry tests.

Body weight measurement at pre-dose on Day 1, Day 4, Day 7, Day 14. Monitor clinical observation of the animal for 14 days post dose.

PK refers to plasma samples.

Procedure to prepare whole blood lysate for PD: Collect enough blood to have (2) aliquots. Each aliquot will be 200 uL.

1) Prepare BD lyse/Fix buffer 5×
    From BD product insert "dilute the required amount of BD Phosflow™ Lyse/Fix Buffer (5× concentrate) 1:5 with deionoized or distilled water (at room temperature) and then pre-warm the solution to 37° C. The 1× working solution should be made fresh for each experiment and any remaining solution at the end of the experiment should be discarded."

2) Fix cells by transferring the 200 uL of blood to 1.8 mL of BD Lyse/Fix Buffer (*1:10 dilution).

3) Incubate for 10 minutes at room temperature.

4) Spin cells down at 1400 rpm for 5 minutes. Aspirate and wash with 10 mM PBS/0.5% BSA (Add this buffer for final volume of 10 mL to spin down)

5) transfer cells to 1.5 mL centrifuge tubes with 1.0 mL of PBS/0.5% BSA buffer spin cells down at 1400 rpm for 5 minutes.

6) Aspirate and freeze down cell pellet. (pure cell pellet with no liquid) *If lysis appears incomplete can adjust to 1:20 dilution (200 uL of blood to 3.8 mL of BD/Lyse/Fix buffer Blood Collection for Hematology Whole blood (at least 1.0 mL) at 168 hours post dose will be collected from the experimental animals into commercially available tubes with Potassium (K2) EDTA at room temperature (RT). The blood samples will be sent to clinical pathology Lab in RT and tested for hematology parameters.

Hematology test items will be performed as below:

| Hematology | |
| --- | --- |
| Erythrocyte count (RBC) | Red cell distribution width (RDW) |
| Hematocrit (HCT) | Platelet count (PLT) |
| Hemoglobin (HGB) | Mean platelet volume (MPV) |
| Mean corpuscular volume (MCV) | Leukocyte counts (WBC) and Differential (absolute and percent) |
| Mean corpuscular hemoglobin (MCH) | Absolute reticulocyte count(Retic) |
| Mean corpuscular hemoglobin concentration (MCHC) | |

Serum Processing for Clinical Chemistry

Whole blood samples (approximately 1.0 mL) without anticoagulant at 168 hours post dose will be collected and held at RT and up-right for at least 30 minutes and sent to clinical pathology Lab for analysis.

Clinical chemistry test items will be performed as below:

| Clinical Chemistry | |
| --- | --- |
| Alkaline Phosphatase (ALP) | Total Protein (TP) |
| Alanine Aminotransferase (ALT) | Albumin (ALB) |
| Aspartate Aminotransferase (AST) | g-glutamyltransferase (GGT) |
| Bilirubin, total (TBIL) | Globulin (GLB) |
| Phosphorus (P) | Albumin/Globulin Ratio |
| Creatinine (CRE) | Sodium (Na) |
| Glucose (GLU) | Chloride (Cl) |
| Calcium (Ca) | Triglycerides (TG) |
| Total Cholesterol (TCHO) | Urea (UREA) |
| Potassium (K) | |

Study Objective

The objective of this study is to determine the pharmacokinetics of Compound A following single or repeated oral administrations of Compound A in male and female cynomolgus monkeys. The test article will be measured in plasma at selected time points for up to 14 days post dosing.

Test Article and Vehicle Information

Test Article

| Name: | Physical State | Chemical Formula | MW/FW (g/mol) | Purity (%) | C.F. |
| --- | --- | --- | --- | --- | --- |
| Compound A | Powder | C45H48F3N7O6S | 871/871 | 98.9 | 1.0111 |

| Storage Conditions: | Desiccate at room temperature, protect from light |
| --- | --- |
| Handling Instructions: | Standard laboratory precautions |

| Dose Preparation: | Doses will be prepared according to instructions provided by the sponsor. A copy of the instructions, as well as details of preparation will be maintained in the study records. |
| --- | --- |
| Dose Solution Analysis Samples: | After each dose preparation, remove at least 20 μL from the formulations, transfer the aliquots into polypropylene micro-centrifuge tubes and stored at −60° C. or lower until assayed in duplicate for dose validation. |
| Disposition of Remaining Test Article Formulation: | Remaining formulations will be stored room temperature. |
| Disposition of Remaining Test Article (dry powder or solid): | Remaining test article will be stored at room temperature desiccated, and protected from light and will be shipped back to sponsor or discarded 6 months after the final report is signed or at approval of sponsor. |

Vehicle and formulation preparation

Formulation: 10% HP-β-CD in water at pH 3.5 (w/v) in water at pH 3.5 (w/v)

Prepare the 10% HP-β-CD vehicle on a (w/v) basis

Add compound with stirring.

Heat to ~50 C for 10 minutes. Can also sonicate.

Adjust pH to 3.5.

Heat for another 10-20 minutes at ~50 C.

Check and adjust the pH as needed.

Expect solution as the measured solubility was 10 mg/mL at 25 C.

Test System Identification

Animal Specifications

| Species | Cynomolgus monkeys |
| --- | --- |
| Justification for Species Selection | This is an acceptable species to support PK studies for compounds intended to use in humans. |
| History of Dosing | Non-naïve animals |
| Body Weight Range | ≥2.5 kg |
| Age | ≥2 years old |
| Sex | Male and Female |
| Number of Animals for Acclimation | 11 males and 11 females |
| Number of Animals for Dosing | 8 males and 8 females |
| Justification for number of Animals | The number of animals in each group is the minimum number of animals necessary for assessment of inter-animal variability. |
| Selection of Animals | 11 males and 11 females will be selected from available stock animals. Animals will have undergone a physical examination for general health. 8 males and 8 females, confirmed as being healthy, will be assigned to study. |
| Acclimation Period | Selected animals will be acclimated prior to the study. |

Animal Care

Environmental Conditions

The room(s) will be controlled and monitored for relative humidity (targeted mean range 40% to 70%, and any excursion from this range for more than 3 hours will be documented as a deviation) and temperature (targeted mean range 18° to 26° C., and any excursion from this range will be documented as a deviation) with 10 to 20 air changes/hour. The room will be on a 12-hour light/dark cycle except when interruptions are necessitated by study activities.

Housing

Animals will be individually housed in stainless-steel mesh cages during in-life Diet and Feeding Animals will be fed twice daily. Stock monkeys will be fed approximately 120 grams of Certified Monkey Diet daily. These amounts can be adjusted as necessary based on food consumption of the group or an individual body weight changes of the group or an individual and/or changes in the certified diet. In addition, animals will receive fruit daily as nutritional enrichment.

Feeding design refer to Table 7-3-1.

Drinking Water

RO (reverses osmosis) water will be available to all animals, ad libitum.

Feed and Water Analyses

RO water was analyzed every three months and every batch of feed will be analyzed before using. Feed and water analyses will be maintained in the facility records.

Environmental Enrichment

Enrichment toys will be provided. Fresh fruits purchased from human food suppliers will be supplied daily, except during periods of fasting.

Administration of Dose Formulation

| | |
|---|---|
| Administration Route: | Orally via nasogastric gavage. |
| Justification for the Dose Level: | Dose levels chosen to characterize the pharmacokinetics of test article in monkeys over adose and plasma concentration range that approximate expected efficacious exposures, with moderate exposure multiples assuming exposure increases with dose. These doses and resultant exposures are not expected to cause any morbidity or toxicity in the NHP based on responses in rodents across similar dose ranges. |
| Justification for the Administration Route: | This administration route is consistent with the proposed initial route of human administration or is needed to meet the study objective. |
| Dose Administration: | The dose formulation will be administered per facility SOPs. ORAL: The nasogastric doses will be flushed using 3 mL of vehicle (approximately 3 times volume of nasogastric tube). All tubes should be equal size and not variable between animals and cut to equal length so that the flush volume is comparable. |

Observations and Examinations

Clinical Observations

Twice daily (approximately 9:30 a.m. and 4:00 p.m.), Cage-side observations for general health and appearance will be done. Animals will be given physical examination prior to study initial to confirm animals' health. Day of dosing: before and after dosing, and before and after each PK sample time point through 24 hour PK sample. Twice daily thereafter. General condition, behavior, activity, excretion, respiration or other unusual observations noted throughout the study will be recorded in the raw data. When necessary, additional clinical observations will be performed and recorded.

Body Weight

All animals will be weighed on the dosing day prior to dosing to determine the dose volume to be administered, and again weekly after.

Blood and Urine Samples Collection

Blood: All blood samples will be collected from a peripheral vessel from restrained, non-sedated animals.

Animals: All available, all groups

Blank Plasma: Whole blood will be collected from available stock animal into commercially available tubes containing Potassium (K2) EDTA on wet ice and processed for plasma. The plasma will be pooled to serve as blank plasma.

Pre-Dose and Post-Dose

Blood volume: Approximately, 0.5 mL, for each time point

Anticoagulant: Potassium ($K_2$) EDTA

Frequency: Refer to Table 7-3-2. Actual sample collection times will be recorded in the study records. For samples collected within the first hour of dosing, a ±1 minute is acceptable. For the remaining time points, samples that are taken within 5% of the scheduled time are acceptable and will not be considered as protocol deviation.

Sample Processing for plasma: 12.5 μL 20% Tween 20 will be added into a commercial tube containing Potassium (K2) EDTA (0.85-1.15 mg) on wet ice, 0.4~0.5 ml blood will be collected into these tubes and processed for plasma. Samples will be centrifuged (3,000×g for 10 minutes at 2 to 8° C.) within one hour of collection. The plasma samples (0.2 mL/Sample) will be transferred into labeled polypropylene micro-centrifuge tubes, respectively, and stored frozen in a freezer set to maintain −60° C. or lower.

Sample Assay and Storage

Dose formulation concentration verification

A LC/UV or LC/MS/MS method will be developed with a calibration curve consisting of 6 calibration standards.

The concentrations of the test compound in dose formulation samples will be determined by the LC/UV or LC/MS/MS method.

Acceptance criteria for an analytical run: at least of 5 of 6 calibration standards should be within 20% of nominal values by using LC/UV method and 30% of nominal values by using LC/MS/MS method.

Bioanalytical method development and sample analysis

LC-MS/MS method development:

1. A LC-MS/MS method for the quantitative determination of test compound in biological matrix will be developed under non-GLP compliance.
2. A calibration curve with at least 7 non-zero calibration standards will be applied for the method including LLOQ.
3. A set of QC samples consisting of low, middle, and high concentration will be applied for the method.
4. N in 1 cassette LC-MS/MS method can be developed for samples coming from different studies as long as these studies belong to same sponsor and the interference among all cassette analytes will be evaluated during the method development.
5. Cassette administration assay could be performed if the mass difference (ΔMass) among different analytes is more than 4 Da. In this case, interference evaluation is not necessary. If the ΔMass among different analytes is less than 4 Da, there is a potential risk that interference would occur during LC-MS/MS analysis. If such kind cassette assay is still requested by the study sponsor, interference between analytes will not be evaluated but the LC separation of those analytes by using a generic method will be tried. If these analytes could not be separated, notice to client will be conducted and documentation on experiment record are needed.
6. Biological sample in matrix other than plasma can be diluted with plasma first and then quantified against plasma calibration curve. And the corresponding dilution QCs to insure the dilution accuracy and matrix difference, will be inserted into analytical run.

Sample analysis:

1. If sample number within a batch is ≤12, at least one set of standard curve separated with two parts through begin and end of the sequence, should be included in the run and QCs are not required. The recommended injection order is C8, C6, C4, C2, study samples, C7, C5, C3, C1.

2. If sample number within a batch >12, one standard curve and two sets of QC samples with low, middle and high concentrations will be applied for bioanalysis, meanwhile, QC sample number should be more than 5% of study sample number.
3. Samples, coming from one client with same types of matrix though in different studies, are allowed to be quantified in one analysis run by using the developed N in 1 cassette LC-MS/MS method.
4. Biological samples in matrix other than plasma are recommended to be diluted with plasma and then quantified against plasma calibration curve. The corresponding dilution QCs to insure the dilution accuracy and matrix difference, will be inserted into analytical run. If sponsor requests specifically, biological samples are then to be quantified against calibration curves in their own corresponding matrices.

Acceptance criteria:
1. Linearity: ≥75% STDs is back calculated to within ±20% of their nominal values in biofluid and within 25% of their nominal values in tissue and feces sample.
2. Accuracy: ≥67% all QC samples is back calculated to within ±20% of their nominal values for biofluid and within 25% of their nominal values for tissue and feces samples.
3. Specificity: The mean calculated concentration in the single blank matrix should be ≤50% LLOQ.
4. Sensitivity:
   4.1 If the biological samples in matrix other than plasma are diluted with plasma and quantified against plasma calibration curve, the LLOQ of plasma calibration curve will be tried to target ≤2 ng/mL, which LLOQ is equivalent to ≤4 ng/mL in biological matrix other than plasma (if dilution 2 folds is applied).
   4.2 If the biological samples are quantified against the calibration curves prepared by their corresponding matrix, the LLOQ will be tried to target ≤3 ng/mL. Any adjustment of LLOQ will inform sponsor in advance
5. Carryover: The mean calculated carry-over peak area in the blank matrix immediately after the highest standard injection should be less than that of LLOQ. If the carryover couldn't meet the criteria, he impact of the carryover on unknown samples should be evaluated according to the below procedure:
   Carryover evaluation should be estimated according to absolute carryover. Carryover contribution is calculated by the area ratio of the blank with the highest carryover (Area max of carryover blank) to the ULOQ with the minimum calculated value (Area min of ULOQ); Carryover impact is calculated by the area ratio of one injection (Area of one injection) to the following injection (Area of the following injection); Absolute carryover is calculated by carryover contribution multiplies carryover impact, the value of absolute carryover should be below 20%.

Carryover contribution=Area max of carryover blank/Area min of ULOQ
   Carryover impact=Area of one injection/Area of the following injection
   Absolute carryover=Carryover contribution*Carryover impact 7.4 Results Table 11 and Table 12 show both IV and PO dosing regimens are supported.

Table 11. IV Dosing in NHP

TABLE 11

| IV Dosing in NHP | | | | |
|---|---|---|---|---|
| IV Dose (mg/kg) | Dosing Schedule | Target exposure Range (Ly10-DHL2) $AUC_{0-168}$ (uM*hr) | Projected Exposure Multiples (Ly10-DHL2) | Clinical Observations |
| 10 | D1 | 24-72 | 1.1-0.37 | None |
| 20 | | | 2.2-0.75 | None |
| 5 | D1, 2 | 12-36 | 1.7-0.6 | None |
| 10 | D1, 2 | | 4.4-1.5 | None |

Hematourea was observed in rats at ≥100 mpk (IV bolus) but not observed in NHP (slow IV push).

TABLE 12

| PO Dosing in NHP | | | | |
|---|---|---|---|---|
| PO Dose (mg/kg) | Dosing Schedule | Target exposure Range (Ly10-DHL2) $AUC_{0-168}$ (uM*hr) | Projected Exposure Multiples (Ly10-DHL2) | Clinical Observations |
| 50 | D1 | 18-54 | 1.2-0.4 | Diarrhea |
| 100 | | | 1.3-0.4 | Diarrhea, Emesis |
| 10 | D1, D4 | 7-18 | 1.9-0.7 | Diarrhea |
| 25 | | | 2.9-1.1 | Diarrhea, Emesis |
| 50 | | | 2.6-1.2 | Diarrhea, Emesis |
| 25 | D1, D2 | | 3-1.2 | Diarrhea, Emesis |

Diarrhea observed in all Compound A groups and emesis was observed at higher doses (100 QD and >25 BID).

Example 8

Lymphopenia Studies

Lymphopenia on intermittent dosing was found to be transient (recovery by D7-14), trends to dose/exposure-dependent (shallower nadir and faster recovery at lower doses, and was similar in both IV and PO dosing.

FIG. 5 shows that Compound A gives sustained tumor PD effect in OCI-Ly10, supporting target coverage from intermittent dosing.

Example 9

Clinical Dosing Schedules

Preclinical data supports several clinical dosing schedules with varying intensity and dosing holiday. Non-GLP toxicity study will assist in the selection of the preferred schedule and dosing holiday/cycle length.

Figure 6:
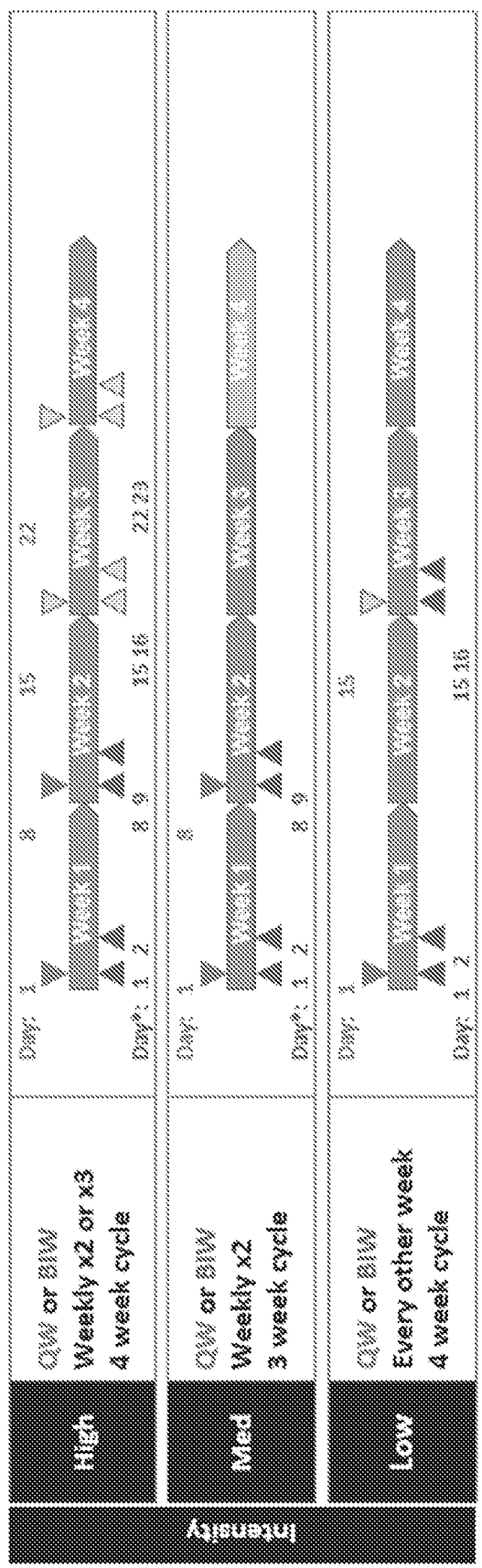
FIG. 6 shows several clinical dosing schedules supported by preclinical data.

FIG. 6 shows several clinical dosing schedules supported by preclinical data including schedules of high, medium, and low intensity. Schedules can support QW or BIW dosing for 2 or 3 successive weeks or every other week in a 3 or 4 week cycle.

Example 10

Dosing Finding Study Design

Figure 7:
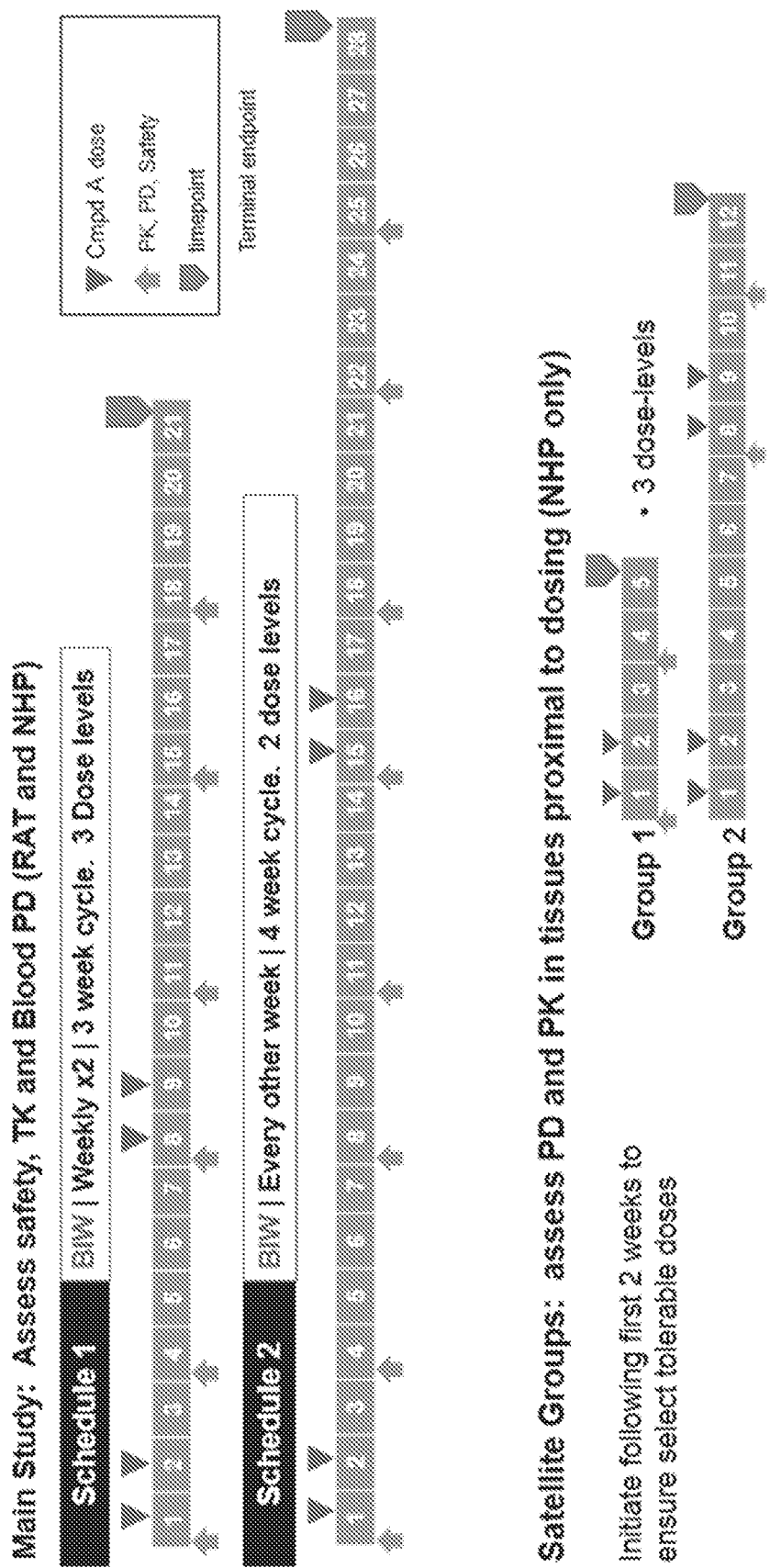
FIG. 7 shows a dosing finding study design.

FIG. 7. shows a dosing finding study design. The main study assess safety, toxicokinetics (TK), and blood PD in rat and NHP. The satellite groups assess PD and PK in tissues proximal to dosing in NHP.

Example 11

Human Dose Predictions

Human dose predictions from intermittent dosing supports dose targets for both IV and PO dosing. Table 13 shows human dose prediction by matching AUCs with the corresponding intermittent dosing regimen in mice models.

TABLE 13

Human Dose Prediction

| | | Mouse | | Human | |
|---|---|---|---|---|---|
| Model | ROA | Dose (mpk) | Schedule | Weekly AUC (μM · h) | Schedule | Projected human dose (mg per dose) |
| OCI-Ly10 | PO | 30 | QW | 18 | QW | 1600 |
| | IV | 12 | | 24 | | 400 |
| | PO | 10 | BIW | 7 | BIW | 300 |
| | IV | 3 | | 12 | | 100 |
| DHL2 | PO | 30 | BIW | 18 | BIW | 900 |
| | IV | ~10 (est.) | | 36 (est.) | | 300 |

IV formulation up to 300 mg/dose is feasible (exposure for efficacy is 100-300 mg/dose). Dosing to ≥400 mg likely possible (>80% POS based on initial formulation assessment). Projected PO upper dose of 900 mg/day is feasible. May be divided into BID dosing to achieve exposure. High pill burden or unusual formulation strategy (e.g., mix and drink) may be needed. PO versus IV dosing in compared in Table 14.

TABLE 14

PO Versus IV Dosing

| | IV | PO |
|---|---|---|
| Efficacy | Efficacy is equivalent between both ROA | |
| Safety | No observed GI events at exposures up to 4.4X MED | GI events (e.g., diarrhea and emesis) likely tolerable, observed in all TA PO dose groups |
| | Lymphocyte declines are transient Nadir appears to be rapid (by D4) with recovery to normal range typically by D8 | Lymphocyte declines are transient Nadir appears to be rapid (By D4) with recovery to normal range typically by D8 |
| | Weekly dosing schedules may be permissible | Weekly dosing schedules may be permissible |
| | Signs of hematuria in rat dosing at higher doses in IV push (at exposures above MED) | |
| | Not observed in NHP: slower infusion likely to manage | |
| Convenience | Less convenient: will require 1 or 2 infusion visits on ongoing basis (4-6 total visits per cycle) | Oral dosing is more convenient. Oral dosing will be more convenient for combinations Oral will enable maintenance dose schedules in early lines |
| Feasibility | IV formulation up to 300 mg/dose (MED is at 100 mg dose) Dosing up to 400 mg may be possible (>80% POS) | Projected upper dose of 900 mg/day High pill burden or unusual formulation strategy (e.g. mix and drink) may be needed |

MED (median effective dose); POS (probability of success).

Example 12

Combination Xenograph Studies

Study Purpose: The objective was to evaluate the efficacy of Compound A combinations in the OCI-LY10 human diffuse large B-cell lymphoma model in female CB-17 SCID mice.

Cell Culture: The OCI-LY10 tumor cells were maintained as a suspension in RPMI1640 medium supplemented with 10% fetal bovine serum and 100 μg/mL penicillin/100 μg/mL streptomycin (study 1) or 1% Antibiotic-Antimycotic (study 2) at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

Animals: CB-17 SCID, female, 6-8 weeks, weighing approximately 18-22 g. In total of 56 animals (study 1) and 66 animals (study 2) were used in the study.

Tumor Inoculation: Each mouse was inoculated subcutaneously at the right flank with OCI-LY10 tumor cells ($10 \times 10^6$) in 0.2 mL of PBS with matrigel for tumor development. The treatments were started when the tumor sizes reach 100 $mm^3$ for the study. The test article administration/formulations and the animal numbers in each group are shown in the following tables.

TABLE 15

Study 1 Formulations

| Compounds | Package | Preparation | Conc mg/mL | Storage |
|---|---|---|---|---|
| IV Vehicle | - | 10% HPβCD:5% TPGS in pH 5-6 water | — | 4° C. |
| PO Vehicle | | 0.5% methylcellulose | — | 4° C. |
| Compound A | Correction factor = 1.02 150.03 mg/vial | Weigh 2.0196 mg Compound A directly in an amber vial, dissolve it with 0.33 mL TPGS, vortex and soncate. Then add 6.27 mL 10% HPβCD, vortex and sonicate to obtain a homogenous suspension. Adjust pH to 1~2 with 6N HCl, then adjust pH back to 5~6 with 5N NaOH, obtain a clear solution with at 0.3 mg/mL. | 0.3 | 4° C. |
| | 0.3 mg/mL | Precisely pipet 1.2 mL of the 0.3 mg/mL solution into a clear brown bottle, and add 2.4 ml Vehicle to formulate a homogenous solution by turning the bottle up and down gently. | 0.1 | 4° C. |
| Ibrutinib | | Weigh 26.25 mg Ibrutinib directly in an amber vial. Dissolve it with 21 mL 0.5% methylcellulose to make a homogeneous suspension. | 1.25 | 4° C. |
| Rituxan | 100 mg: 10 mL/vial | Precisely pipet 0.180 mL of the 10 mg/mL Rituxan solution into a clear brown bottle, and add 0.720 ml 0.9% saline to formulate a homogenous solution by turning the bottle up and down gently. | 2 | 4° C. |
| Rituxan | 100 mg: 10 mL/vial | Precisely pipet 0.360 mL of the 10 mg/mL Rituxan solution into a clear brown bottle, and add 3.240 ml 0.9% saline to formulate a homogenous solution by turning the bottle up and down gently. | 1 | 4° C. |
| Doxorubicin | 10 mg/vial | Dissolve 10 mg Doxorubicin in original bottle with 4 mL 0.9% saline to obtain a 2.5 mg/mL solution. | 2.5 | 4° C. |
| Doxorubicin | 2.5 mg/mL | Precisely pipet 0.240 mL of the 2.5 mg/mL Doxorubicin solution into a clear brown bottle, and add 0.760 ml 0.9% saline to formulate a homogenous solution by turning the bottle up and down gently. | 0.6 | 4° C. |
| Vincristine | 1 mg/vial 0.2 mg/mL | Precisely pipet 0.750 mL of the 0.2 mg/mL Vincristine solution into a clear brown bottle, and add 2.250 ml 0.9% saline to formulate a homogenous solution by turning the bottle up and down gently. | 0.05 | 4° C. |
| Cyclophosphamide | 200 mg/vial 20 mg/mL | Precisely pipet 0.600 mL of the 20 mg/mL Cyclophosphamide solution into a clear brown bottle, and add 2.400 ml 0.9% saline to formulate a homogenous solution by turning the bottle up and down gently. | 4 | 4° C. |
| Prednisone | 25 mg/vial | Weigh 2.00 mg Prednisone directly in an amber vial. Dissolve it with 20 mL 0.9% saline to make a homogeneous suspension. | 0.1 | 4° C. |

TABLE 16

Study 1 Administration Schedules

| Group | n | Treatment | Dose (mg/kg) | Dosing Volume | Dosing Route | Schedule |
|---|---|---|---|---|---|---|
| 1 | 6 | PO Vehicle | — | 10 μl/g | PO | QDx21 |
| | | IV Vehicle | — | 10 μl/g | IV | QW |
| 2 | 6 | Ibrutinib | 12.5 | 10 μl/g | PO | QDx21 |
| 3 | 6 | Compound A | 1 | 10 μl/g | IV | D1, 2, 8, 9, 15, 16, 22, 23 |
| 4 | 6 | Compound A | 3 | 10 μl/g | IV | D1, 2, 8, 9, 15, 16, 22, 23 |
| 5 | 6 | Ibrutinib | 12.5 | 10 μl/g | PO | QDx21 |
| | | Compound A | 1 | 10 μl/g | IV | D1, 2, 8, 9, 15, 16, 22, 23 |
| 6 | 6 | Ibrutinib | 12.5 | 10 μl/g | PO | QDx21 |
| | | Compound A | 3 | 10 μl/g | IV | D1, 2, 8, 9, 15, 16, 22, 23 |
| 7 | 6 | Rituxan | 10 | 10 μl/g | IP | BIW |
| 8 | 6 | Rituxan | 10 | 10 μl/g | IP | BIW |
| | | Compound A | 3 | 10 μl/g | IV | D1, 2, 8, 9, 15, 16, 22, 23 |
| 9 | 6 | R-CHOP (SoC ref) * | | 5 μl/g | | | n = animal number; Dosing volume = adjust dosing volume based on body weight.

R-CHOP:

| Agent | Dose (mg/kg) | Dosing Volume | Route | Schedule |
|---|---|---|---|---|
| Rituxan | 10 | 5 μl/g | IP | D1 |
| Doxorubicin | 3 | 5 μl/g | IV | D1 |
| Vincristine | 0.25 | 5 μl/g | IV | D1 |
| Cyclophosphamide | 20 | 5 μl/g | IV | D1 |
| Prednisone | 0.5 | 5 μl/g | PO | D1, 2, 3, 4, 5 |

3 days prior to treatment initiation, augment diet gel/supplement to all study animals. Compound are diluted to required dosing volume with 0.9% saline R-CHOP Dosing Sequence: Rituxan, IP; Doxorubicin, IV 15 min post Rituxan; Vincristine, IV 15 min post Doxorubicin; Cyclophosphamide, IV 15 min post Vincristine; Prednisone, PO 15 min post Cyclophosphamide.

TABLE 17

Study 2 Formuations

| Compounds | Package | Preparation | Conc mg/mL | Storage |
|---|---|---|---|---|
| Ibrutinib (0.5% methylcellulose) | 5 g/vial Correction factor: 1.00 | Weigh 26.25 mg Ibrutinib directly in an amber vial. Dissolve it with 21 mL 0.5% methylcellulose to make a homogeneous suspension. | 1.25 | 4° C. |
| CA-4948 (50 parts of 1% tween 20 in water and 50 parts of 0.5% hydroxyethyl cellulose) | 2 g/vial Correction factor: 1.00 | Weigh 157.5 mg CA-4948 directly in an amber vial. dissolve it with 5.250 mL 1% tween 20 in water, vortex and sonicate. Then add 5.250 mL 0.5% hydroxy ethyl cellulose in water, vortex and sonicate to make 15.0 mg/mL suspension. | 15 | 4° C. |
| Rituxan (0.9% saline) | 100 mg: 10 mL/vial | Precisely pipet 0.50 mL of the 10 mg/mL Rituxan solution into a clear brown bottle, and add 4.500 ml 0.9% saline to formulate a homogenous solution by turning the bottle up and down gently. | 1 | 4° C. |
| Venetoclax (5% DMSO + 50% PEG 300 + 5% Tween 80 + ddH$_2$O) | 1 g/vial Correction factor: 1.00 | Weigh 105 mg Venetoclax directly in an amber vial. Dissolve it with 1.05 mL DMSO thoroughly, then add 10.5 mL PEG 300 and 1.05 mL Tween 80, mix well. Then dilute the solution with 8.4 mL water to make 21 mL of 5 mg/mL solution. | 5 | 4° C. |
| Compound A (10% HPβCD:5% TPGS in pH 5-6 water) | 100.06 mg/vial Correction factor = 1.02 | Weigh 2.5704 mg IRW-O-2019-018N directly in an amber vial, dissolve it with 0.420 mL TPGS, vortex and soncate. Then add 7.980 mL 10% HPβCD, vortex and sonicate to obtain a homogenous suspension. Adjust pH to 1~2 with 6N HCl, then adjust pH back to 5~6 with 5N NaOH, obtain a clear solution with at 0.3 mg/mL. | 0.3 | 4° C. |
|  | 0.3 mg/mL | Precisely pipet 1.200 ml of the 0.3 mg/mL solution into a clear brown bottle, and add 2.400 ml IV Vehicle to formulate a clear solution by turning the bottle up and down gently. | 0.1 | 4° C. |

TABLE 18

Study 2 Adminstration Schedules

| Group | n | Treatment | Dose (mg/kg) | Dosing Volume | Dosing Route | Schedule |
|---|---|---|---|---|---|---|
| 1 | 6 | PO Vehicle (50 parts of 1% tween 20 in water and 50 parts of 0.5% hydroxyethyl cellulose) | — | 10 μl/g | PO | QDx21 |
| 2 | 6 | Ibrutinib | 12.5 | 10 μl/g | PO | QDx21 |
| 3 | 6 | CA-4948 | 150 | 10 μl/g | PO | QDx21 |
| 4 | 6 | Rituxan | 10 | 10 μl/g | IV | BIW |
| 5 | 6 | Venetoclax | 50 | 10 μl/g | PO | QDx21 |
| 6 | 6 | Compound A | 1 | 10 μl/g | IV | D1, 2, 15, 16 |
| 7 | 6 | Compound A | 3 | 10 μl/g | IV | D1, 2, 15, 16 |
| 8 | 6 | Rituxan | 10 | 10 μl/g | IV | BIW |
|   |   | Compound A | 1 | 10 μl/g | IV | D1, 2, 15, 16 |
| 9 | 6 | Rituxan | 10 | 10 μl/g | IV | BIW |
|   |   | Compound A | 3 | 10 μl/g | IV | D1, 2, 15, 16 |
| 10 | 6 | Ibrutinib | 12.5 | 10 μl/g | PO | QDx21 |
|   |   | Compound A | 3 | 10 μl/g | IV | D1, 2, 15, 16 |
| 11 | 6 | Venetoclax | 50 | 10 μl/g | PO | QDx21 |
|   |   | Compound A | 3 | 10 μl/g | IV | D1, 2, 15, 16 | n = animal number; Dosing volume = adjust dosing volume based on body weight.

Assignment to Groups: Before commencement of treatment, all animals were weighed and the tumor volumes measured. Since the tumor volume can affect the compound efficacy, mice were assigned into groups using an Excel-based randomization procedure performing stratified randomization based upon their tumor volumes.

Animal Housing: An acclimation period of approximately one week was allowed between animal receipt and tumor inoculation in order to accustom the animals to the laboratory environment. The mice were maintained in a special pathogen-free environment and in individual ventilation cages (3 mice per cage). All cages, bedding, and water were sterilized before use. When working in the mouse room, the investigators wore lab coat and latex or vinyl gloves. Each cage was clearly labeled with a cage card indicating number of animals, sex, strain, date received, treatment, study number, group number, and the starting date of the treatment. The cages with food and water were changed twice a week. The targeted conditions for animal room environment and photoperiod were as follows: Temperature 20~26° C.; Humidity 40~70%; Light cycle 12 hours light and 12 hours dark.

Dietary Materials: All animals had free access to a standard certified commercial laboratory diet. Maximum allowable concentrations of contaminants in the diet were controlled and routinely analyzed by the manufacturers. Autoclaved municipal tap water, suitable for human consumption was available to the animals ad libitum.

Figure 10:
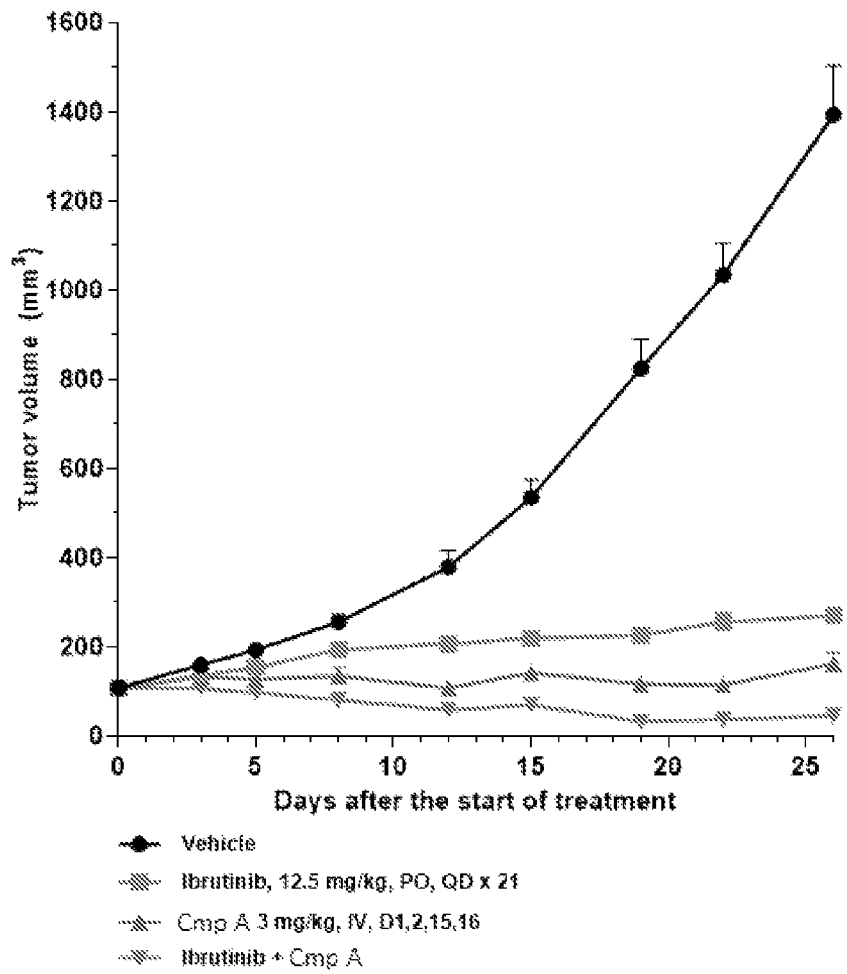
FIG. 10 shows that Compound A is additive in combination with ibrutinib in mutant MYD88 OCI-Ly10 xenographs.
Figure 11:
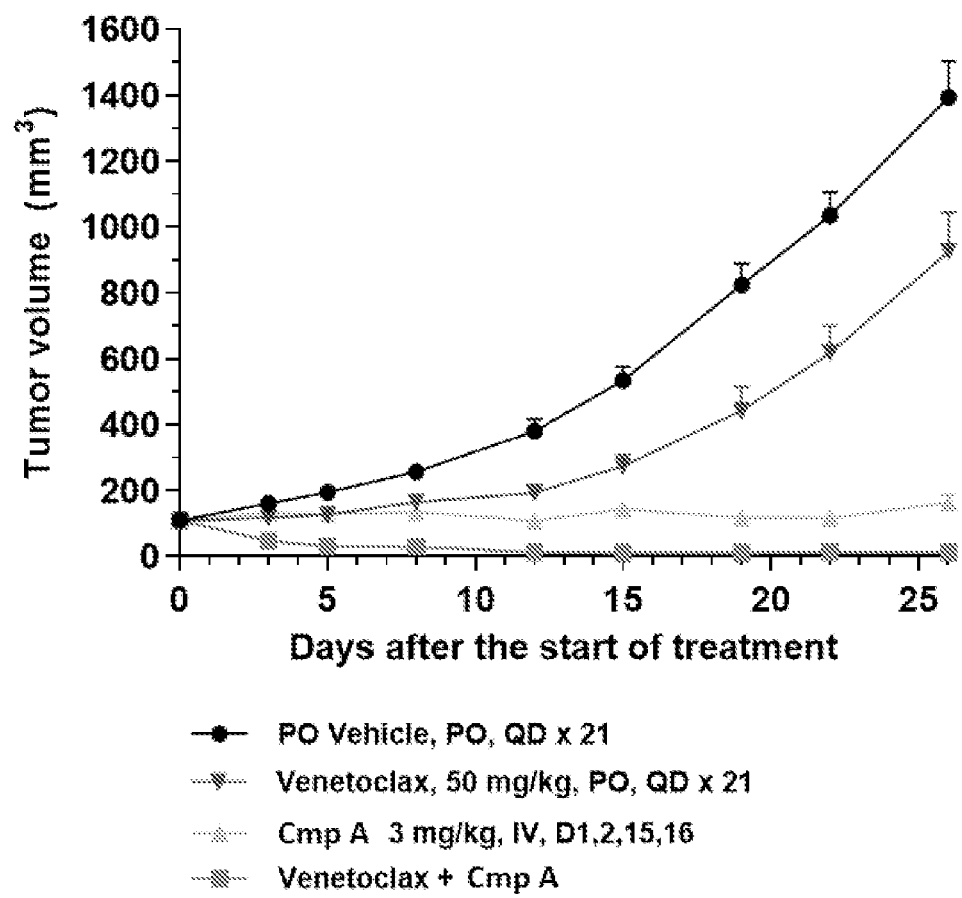
FIG. 11 shows that Compound A is supra-additive in combination with venetoclax in mutant MYD88 OCI-Ly10 xenographs.
Figure 12:
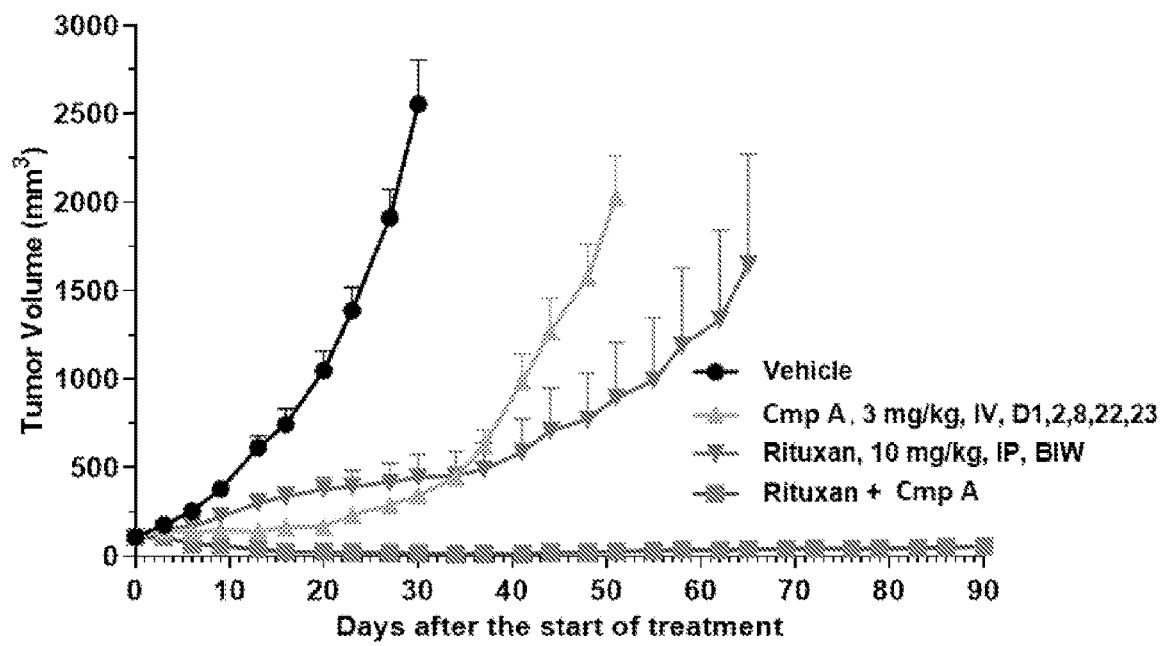
FIG. 12 shows that Compound A is supra-additive in combination with rituximab in mutant MYD88 OCI-Ly10 xenographs (upper graph) including in tumors that relapsed following initial R-CHOP treatment (lower graph).
Figure 12:
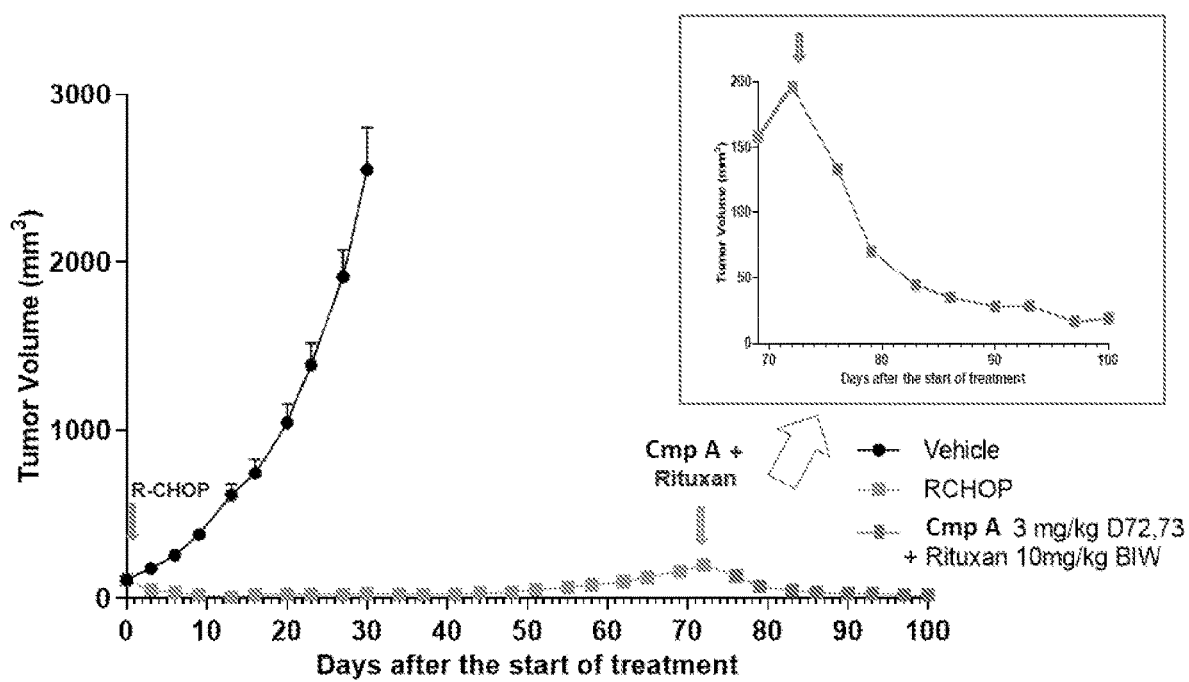

Results: FIGS. 10-12 show results of the combination studies.

FIG. 10 shows that Compound A is additive in combination with ibrutinib in mutant MYD88 OCI-Ly10 xenographs. The data shows that Compound A administered on intermittent schedules demonstrated additive activity with strong regressions in combination with BTK inhibitors (e.g., ibrutinib).

FIG. 11 shows that Compound A is supra-additive (determined by Bliss independent method) in combination with venetoclax in mutant MYD88 OCI-Ly10 xenographs. The data shows that Compound A administered on intermittent schedules demonstrated supra-additive activity with deep and durable regressions in combination with BCL-2 inhibitors (e.g., venetoclax).

FIG. 12 shows that Compound A is supra-additive (determined by Bliss independent method) in combination with rituximab in mutant MYD88 OCI-Ly10 xenographs (upper graph) including in tumors that relapsed following initial R-CHOP treatment (lower graph). The data shows that Compound A administered on intermittent schedules demonstrated deep and durable regressions in combination with an anti-CD20 antibody (e.g., rituximab) and the combination also showed strong tumor regressions in tumors that relapsed following initial R-CHOP treatment.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:

1. A method of treating a MYD88-mutant B-cell lymphoma in a patient in need thereof, comprising administering a therapeutically effective amount of Compound A or a pharmaceutically acceptable salt thereof to the patient; wherein Compound A is N-(2-((1r,4r)-4-((6-(2-((2-(2,6-dioxopiperidin-3-yl)-1,3-dioxoisoindolin-4-yl) amino) ethyl)-2-azaspiro[3.3]heptan-2-yl)methyl)cyclohexyl)-5-(2-hydroxypropan-2-yl)benzo[d]thiazol-6-yl)-6-(trifluoromethyl)picolinamide. wherein Compound A or a pharmaceutically acceptable salt thereof is administered at a dose of up to 1600 mg to the patient.

2. The method of claim 1, wherein Compound A or a pharmaceutically acceptable salt thereof is administered at a dose of up to 900 mg to the patient.

3. The method of claim 1, wherein Compound A or a pharmaceutically acceptable salt thereof is administered at a dose of up to 400 mg to the patient.

4. The method of claim 1, wherein Compound A or a pharmaceutically acceptable salt thereof is administered at a dose of up to 300 mg to the patient.

5. The method of claim 1, wherein Compound A or a pharmaceutically acceptable salt thereof is administered at a dose of from about 300 mg to about 900 mg.

6. The method of claim 1, wherein Compound A or a pharmaceutically acceptable salt thereof is administered at a dose of from about 100 mg to about 300 mg.

7. The method of claim 1, wherein Compound A or a pharmaceutically acceptable salt thereof is administered at a dose of from about 30 mg/m$^2$ to about 90 mg/m$^2$.

8. The method of claim 1, wherein Compound A or a pharmaceutically acceptable salt thereof is administered at a dose of from about 10 mg/m$^2$ to about 40 mg/m$^2$.

9. The method of claim 1, wherein Compound A or a pharmaceutically acceptable salt thereof is administered orally to the patient.

10. The method of claim 9, wherein the oral administration of Compound A to the patient comprises solutions, suspensions, emulsions, tablets, pills, capsules, powders, or sustained-release formulations.

11. The method of claim 1, wherein Compound A or a pharmaceutically acceptable salt thereof is administered intravenously to the patient.

12. The method of claim 11, wherein the intravenous administration of Compound A to the patient comprises sterile injectable solutions.

13. The method of claim 1, wherein Compound A or a pharmaceutically acceptable salt thereof is administered to the patient once weekly.

14. The method of claim 1, wherein Compound A or a pharmaceutically acceptable salt thereof is administered to the patient twice weekly.

15. The method of claim 14, wherein the administration of Compound A or a pharmaceutically acceptable salt thereof is on day 1 and day 2 of the week.

16. The method of claim 14, wherein the administration of Compound A or a pharmaceutically acceptable salt thereof is on day 1 and day 4 of the week.

17. The method of claim 1, wherein Compound A or a pharmaceutically acceptable salt thereof is administered to the patient once weekly in week 1 and week 2 in a 3 week administration cycle.

18. The method of claim 1, wherein Compound A or a pharmaceutically acceptable salt thereof is administered to the patient twice weekly in week 1 and week 2 in a 3 week administration cycle.

19. The method of claim 1, wherein Compound A or a pharmaceutically acceptable salt thereof is administered to the patient once weekly in week 1 and week 2 in a 4 week administration cycle.

20. The method of claim 1, wherein Compound A or a pharmaceutically acceptable salt thereof is administered to the patient twice weekly in week 1 and week 2 in a 4 week administration cycle.

21. The method of claim 1, wherein Compound A or a pharmaceutically acceptable salt thereof is administered to the patient once weekly in week 1 and week 3 in a 4 week administration cycle.

22. The method of claim 1, wherein Compound A or a pharmaceutically acceptable salt thereof is administered to the patient twice weekly in week 1 and week 3 in a 4 week administration cycle.

23. The method of claim 1, wherein Compound A or a pharmaceutically acceptable salt thereof is administered to the patient once weekly in weeks 1-3 in a 4 week administration cycle.

24. The method of claim 1, wherein Compound A or a pharmaceutically acceptable salt thereof is administered to the patient twice weekly in weeks 1-3 in a 4 week administration cycle.

25. The method of claim 1, wherein Compound A or a pharmaceutically acceptable salt thereof is administered as a pharmaceutical composition comprising one or more pharmaceutically acceptable excipient or carrier.

26. The method of claim 25, wherein the one or more pharmaceutically acceptable excipient or carrier comprises one or more diluents, preservatives, binders, lubricants, disintegrators, swelling agents, fillers, or stabilizers.

27. The method of claim 25, wherein the one or more pharmaceutically acceptable excipient or carrier comprises one or more buffers, surfactants, dispersants, emulsifiers, or viscosity modifying agents.

28. The method of claim 1, wherein the MYD88-mutant B-cell lymphoma is selected from ABC DLBCL, primary CNS lymphomas, primary extranodal lymphomas, Waldenstrom macroglobulinemia, Hodgkin's lymphoma, primary cutaneous T-cell lymphoma and chronic lymphocytic leukemia.

29. The method of claim 1, wherein the patient has received at least one prior therapy.

30. The method of claim 1, wherein the patient is a human.

* * * * *